United States Patent
Kuerten et al.

(10) Patent No.: US 11,340,224 B2
(45) Date of Patent: *May 24, 2022

(54) WHOLE BRAIN LYSATE ANTIGEN-SPECIFIC MEMORY B CELL AND ANTIBODY ASSAYS IN MULTIPLE SCLEROSIS

(75) Inventors: Stefanie Kuerten, Dormagen (DE); Paul Lehmann, Moreland Hills, OH (US)

(73) Assignee: CELLULAR TECHNOLOGY LIMITED, Shaker Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/113,740

(22) PCT Filed: May 3, 2012

(86) PCT No.: PCT/US2012/000232
§ 371 (c)(1),
(2), (4) Date: Dec. 9, 2013

(87) PCT Pub. No.: WO2012/154215
PCT Pub. Date: Nov. 15, 2012

(65) Prior Publication Data
US 2014/0255346 A1    Sep. 11, 2014

Related U.S. Application Data

(60) Provisional application No. 61/482,365, filed on May 4, 2011.

(51) Int. Cl.
| | | |
|---|---|---|
| G01N 33/564 | (2006.01) | |
| G01N 33/569 | (2006.01) | |
| G01N 33/68 | (2006.01) | |
| A61P 37/00 | (2006.01) | |
| G01N 33/50 | (2006.01) | |

(52) U.S. Cl.
CPC ........ *G01N 33/56966* (2013.01); *A61P 37/00* (2018.01); *G01N 33/5058* (2013.01); *G01N 33/564* (2013.01); *G01N 33/56972* (2013.01); *G01N 33/6893* (2013.01); *G01N 2333/54* (2013.01); *G01N 2333/55* (2013.01); *G01N 2333/57* (2013.01); *G01N 2800/285* (2013.01); *G01N 2800/50* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| | | | | |
|---|---|---|---|---|
| 8,673,293 B2* | 3/2014 | Martin | ............... | A61K 39/0008 424/184.1 |
| 2004/0043431 A1 | 3/2004 | Vojdani | | |
| 2010/0233121 A1 | 9/2010 | Frohna | | |

FOREIGN PATENT DOCUMENTS

WO   PCT/US2012/000232    5/2012

OTHER PUBLICATIONS

Mond, J.J. and Brunswick, M. Curr. Prot. Immunol. 2000. Unit 11.13, pp. 11.13.1-11.13.17.*
Pinna, D., et al. Eur. J. Immunol. 2009;39:1260-1270.*
Lisak, R.P., et al. Clin. Exp. Immunol. 1975;22:30-34. (Year: 1975).*
Hellings, Niels, T-Cell Reactivity to Multiple Myelin Antigens in Multiple Sclerosis Patients and Healthy Controls, Hournal of Neuroscience Research 63:290-302 (2001), Wiley-Liss, Inc.
Jansson, A., Elispt assay detection of cytokine secretion in multiple sclerosis patients treated with interferonbla or glatiramer acetate compared with untreated patients, Multi Sclerosis 2003: 9:440-445, Arnold 2003.
Kuerten, Stefanie, Identification of a B cell-dependent subpopulation of multiple sclerosis by measurements of brain-reactive B cells in the blood, Clinical Immunology (2014) 152, 20-24, Elsevier.
Ngono, Annie Elong, Frequency of circulating autoreactive T cells commited to myelin determinants in relapsing-remitting multiple sclerosis patients, Clinical Immunology (2012) 144, 117-126, Elsevier.
Oissen, Tomas, Autoreative T Lymphocytes in Multiple Sclerosis Determined by Antigen induced Secretion of Interferon-y, J. Clin. Invest, vol. 86, Aug. 1990, 981-985, The American Society for Clinical Investigation, Inc.
Pinna D et al., Clonal dissection of the human memory B-cell repertoire following infection and vaccination. Eur J Immunol (2009) 39, 1260-1270.
Sandberg et al., B Cell Activation in Multiple Sclerosis. Acta Neurol Scand (1986)74: 417-424.
Fraussen et al., B Cell Characterization and Reactivity Analysis in Multiple Sclerosis. Autoimmunity Reviews (2009) 654-658.
Weinstock-Guttman et al., Interferon-β Treatment for Relapsing Multiple Sclerosis. Expert Opinion on Biological Therapy, (2008) 8:9 1435-1447.
Kuenz et al., Cerebrospinal fluid B cells correlate with early brain inflammation in multiple sclerosis. PLoS One 2008; 3: e2559.
Serafini et al., Detection of ectopic B-cell follicles with germinal centers in the meninges of patients with secondary progresive multiple sclerosis, Brain Pathol, 2004 14:164-174.
Kuerten et al., Differential patterns of spinal cord pathology induced by mp4, mog peptide 35-55, and pip peptide 178-191 in c57bl/6 mice. APMIS. 2011; 119(6):336-46.

* cited by examiner

*Primary Examiner* — G. R. Ewoldt
(74) *Attorney, Agent, or Firm* — D. Benjamin Borson; Borson Law Group PC

(57) ABSTRACT

Embodiments of this invention include methods for detecting in vitro the presence of Memory B cells in peripheral blood mononuclear cells (PBMCs) that produce antibodies reactive to CNS antigens associated with Multiple Sclerosis (MS). Stimulating PBMCs from patients with MS by a polyclonal stimulating agent promotes the ability of B-lymphocytes, when exposed to a CNS antigen, to produce antibodies specific for the CNS antigen. In contrast, stimulating PBMCs from subjects without MS do not produce such responses.

6 Claims, 39 Drawing Sheets
(16 of 39 Drawing Sheet(s) Filed in Color)
Specification includes a Sequence Listing.

medium control

MP4

MS patients medium control

MP4 healthy controls

IFN-γ medium control     MP4

MS patients healthy controls

IL-17 medium control          MP4

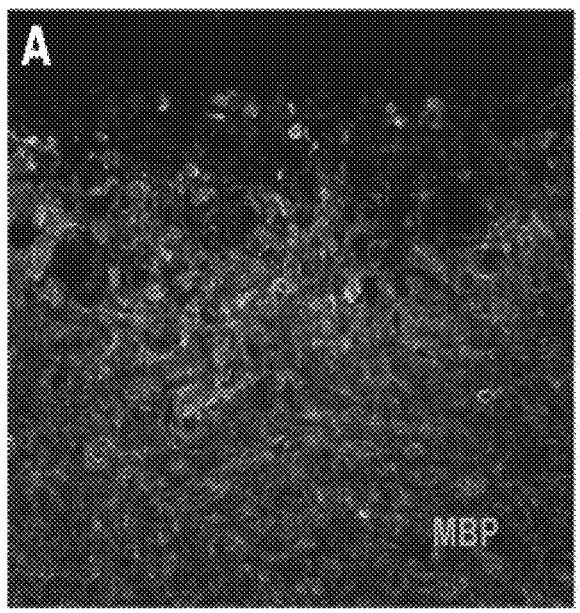
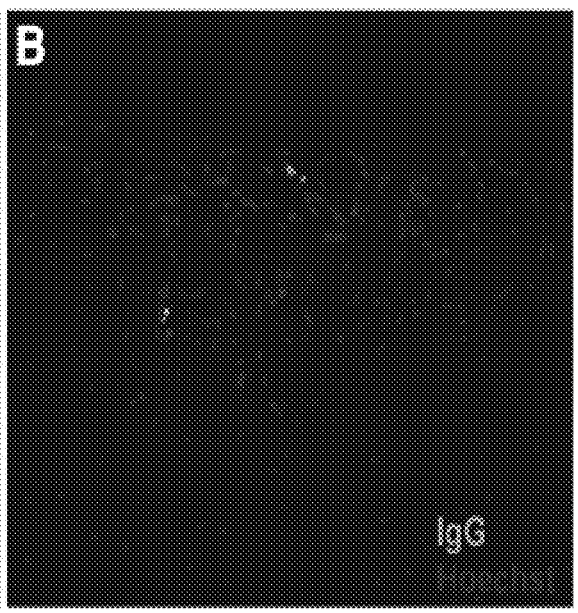
FIG. 13A  FIG. 13B
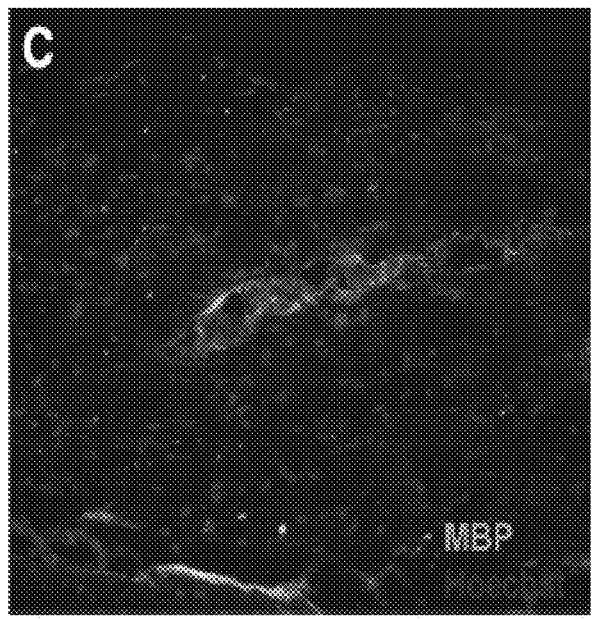
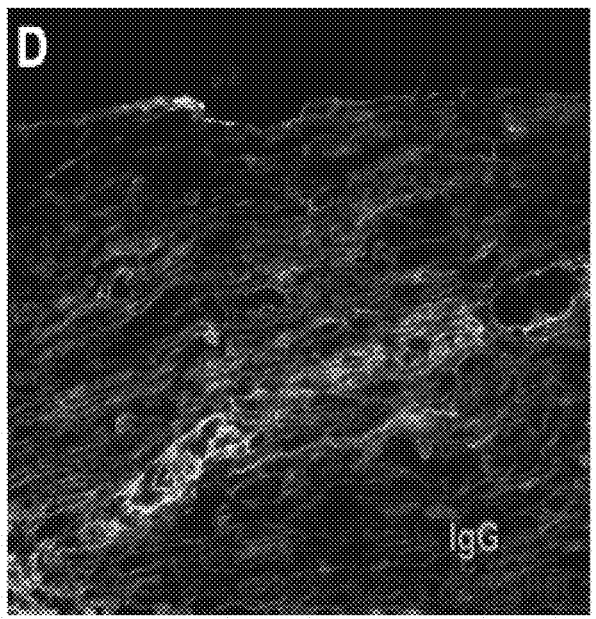
FIG. 13C  FIG. 13D

| Healthy control ID | Disease stage | Disease Activity | Serum antibodies | T$_H$1 | T$_H$17 | Direct B cell test | Indirect B cell test |
|---|---|---|---|---|---|---|---|
| 20060109I | n.a. | n.a. | n.d. | 1.50 ± 1.50 | 0.00 ± 2.00 | - | - |
| 20060220C | n.a. | n.a. | n.d. | 0.00 ± 0.50 | 4.00 ± 0.50 | - | - |
| 200604061 | n.a. | n.a. | n.d. | 0.50 ± 0.50 | 0.00 ± 3.00 | - | - |
| 20060720 | n.a. | n.a. | n.d. | 0.00 ± 0.00 | 0.50 ± 0.00 | - | - |
| 20060213E | n.a. | n.a. | n.d. | 0.00 ± 0.00 | 0.50 ± 0.50 | - | - |
| 20060227J | n.a. | n.a. | n.d. | 0.00 ± 0.00 | 0.50 ± 0.50 | - | - |
| 20060427L | n.a. | n.a. | n.d. | 1.00 ± 1.00 | 3.00 ± 0.50 | - | - |
| 20060803 | n.a. | n.a. | n.d. | 2.00 ± 1.00 | 0.00 ± 1.00 | - | - |
| 20060803J | n.a. | n.a. | n.d. | 5.00 ± 6.50 | 0.50 ± 0.50 | - | - |
| 20060824 | n.a. | n.a. | n.d. | 0.00 ± 0.50 | 0.00 ± 3.50 | - | - |
| 20060913 | n.a. | n.a. | n.d. | 10.50 ± 1.50 | 0.00 ± 2.50 | - | - |
| 20060831 | n.a. | n.a. | n.d. | 9.50 ± 3.50 | 0.50 ± 0.00 | - | - |
| 20060503G | n.a. | n.a. | n.d. | 0.50 ± 0.50 | 6.00 ± 4.00 | - | - |
| 20060906 | n.a. | n.a. | n.d. | 8.50 ± 1.00 | 1.00 ± 0.50 | - | - |
| 20060608M | n.a. | n.a. | n.d. | 5.00 ± 0.00 | 0.00 ± 0.50 | - | - |
| 200620920 | n.a. | n.a. | n.d. | 0.00 ± 0.50 | 2.50 ± 3.00 | - | - |
| 20060412F | n.a. | n.a. | n.d. | 3.00 ± 1.00 | 1.00 ± 1.50 | - | - |
| 20061005 | n.a. | n.a. | n.d. | 4.00 ± 0.00 | 0.00 ± 0.00 | - | - |
| 20060417K | n.a. | n.a. | n.d. | 3.50 ± 2.00 | 0.50 ± 1.50 | - | - |
| 20061012A | n.a. | n.a. | n.d. | 8.00 ± 1.00 | 0.50 ± 1.00 | - | - |
| 20061116 | n.a. | n.a. | n.d. | 5.50 ± 0.00 | 4.50 ± 0.00 | - | - |
| 20061130 | n.a. | n.a. | n.d. | 1.50 ± 0.50 | 2.00 ± 0.00 | - | - |
| 20061207 | n.a. | n.a. | n.d. | 12.00 ± 3.50 | 0.00 ± 1.50 | - | - |
| 20060504H | n.a. | n.a. | n.d. | 10.50 ± 0.00 | 0.00 ± 0.00 | - | - |
| 20060518M | n.a. | n.a. | n.d. | 5.00 ± 2.00 | 1.00 ± 0.00 | - | - |
| 20061214B | n.a. | n.a. | n.d. | 15.50 ± 6.00 | 0.00 ± 2.00 | - | - |
| 20060524J | n.a. | n.a. | n.d. | 0.50 ± 1.00 | 1.00 ± 2.00 | - | - |
| 20061221 | n.a. | n.a. | n.d. | 9.50 ± 1.50 | 1.50 ± 1.00 | - | - |
| 20080206 | n.a. | n.a. | n.d. | 6.00 ± 0.50 | 0.00 ± 1.00 | - | - |
| 20060615K | n.a. | n.a. | n.d. | 1.50 ± 5.50 | 2.00 ± 7.00 | - | - |
| 20080213 | n.a. | n.a. | n.d. | 11.0 ± 5.00 | 2.50 ± 4.50 | - | - |
| 200606221 | n.a. | n.a. | n.d. | 0.00 ± 0.00 | 1.00 ± 1.00 | - | - |
| 20080305 | n.a. | n.a. | n.d. | 0.00 ± 2.50 | 0.00 ± 0.50 | - | - |
| 20060627N | n.a. | n.a. | n.d. | 0.00 ± 0.00 | 1.50 ± 0.50 | - | - |
| 20080312 | n.a. | n.a. | n.d. | 13.00 ± 5.50 | 0.00 ± 3.50 | - | - |
| 20060629P | n.a. | n.a. | n.d. | 0.00 ± 0.00 | 0.50 ± 0.50 | - | - |
| 20080317 | n.a. | n.a. | n.d. | 0.00 ± 4.00 | 0.00 ± 2.00 | - | - |
| 20060713 | n.a. | n.a. | n.d. | 4.00 ± 2.50 | 1.00 ± 4.50 | - | - |
| HC1 | n.a. | n.a. | 0.89 ± 0.07 | 0.00 ± 0.00 | 0.00 ± 7.00 | - | - |
| HC2 | n.a. | n.a. | 0.74 ± 0.05 | 6.50 ± 5.00 | 1.50 ± 0.50 | - | - |
| HC3 | n.a. | n.a. | 0.54 ± 0.11 | 0.00 ± 0.50 | 0.00 ± 3.50 | - | - |
| HC4 | n.a. | n.a. | 0.67 ± 0.07 | 0.00 ± 1.00 | 1.50 ± 4.00 | - | - |
| HCRP | n.a. | n.a. | 0.10 ± 0.07 | 2.00 ± 4.50 | 0.00 ± 3.50 | - | - |
| HCIK | n.a. | n.a. | 0.24 ± 0.01 | 0.00 ± 0.50 | 4.50 ± 0.50 | - | - |
| HCCED | n.a. | n.a. | 0.00 ± 0.06 | 0.00 ± 1.50 | 0.00 ± 2.50 | - | - |
| HCGP | n.a. | n.a. | n.d. | 0.50 ± 1.00 | 0.50 ± 0.50 | - | - |

FIG. 20A

| Healthy control ID | Disease stage | Disease Activity | Serum antibodies | T$_H$1 | T$_H$17 | Direct B cell test | Indirect B cell test |
|---|---|---|---|---|---|---|---|
| HCBEI | n.a. | n.a. | n.d. | 0.00 ± 1.50 | 0.00 ± 1.50 | - | - |
| HCCHH | n.a. | n.a. | 0.63 ± 0.06 | 0.00 ± 1.00 | 0.00 ± 1.50 | - | - |
| HCJR | n.a. | n.a. | 0.52 ± 0.12 | 0.00 ± 0.50 | 0.00 ± 1.50 | - | - |
| HCPH | n.a. | n.a. | n.d. | 0.00 ± 0.50 | 0.00 ± 0.50 | - | - |
| HCMR | n.a. | n.a. | 0.47 ± 0.32 | 8.00 ± 2.50 | 0.00 ± 4.50 | - | - |
| HCGD | n.a. | n.a. | 0.48 ± 0.00 | 1.50 ± 1.50 | 0.50 ± 2.50 | - | - |
| HCTLG | n.a. | n.a. | 0.53 ± 0.38 | 0.00 ± 1.00 | 0.00 ± 0.00 | - | - |
| HCNAM | n.a. | n.a. | 0.48 ± 0.02 | n.d. | n.d. | n.d. | n.d. |
| HCMM | n.a. | n.a. | 0.03 ± 0.02 | n.d. | n.d. | n.d. | n.d. |
| HCIE | n.a. | n.a. | 0.46 ± 0.02 | n.d. | n.d. | n.d. | n.d. |
| HCMABO | n.a. | n.a. | 0.04 ± 0.02 | n.d. | n.d. | n.d. | n.d. |
| HCNSCH | n.a. | n.a. | 0.19 ± 0.02 | n.d. | n.d. | n.d. | n.d. |
| HCSMÜ | n.a. | n.a. | 0.09 ± 0.01 | n.d. | n.d. | n.d. | n.d. |
| HCAA | n.a. | n.a. | 0.49 ± 0.06 | n.d. | n.d. | n.d. | n.d. |
| HCKZ | n.a. | n.a. | 0.35 ± 0.06 | n.d. | n.d. | n.d. | n.d. |
| HCCST | n.a. | n.a. | 0.21 ± 0.02 | n.d. | n.d. | n.d. | n.d. |
| HCLL | n.a. | n.a. | 0.52 ± 0.09 | n.d. | n.d. | n.d. | n.d. |
| HCTH | n.a. | n.a. | 0.75 ± 0.07 | n.d. | n.d. | n.d. | n.d. |
| HCVG | n.a. | n.a. | 0.28 ± 0.01 | n.d. | n.d. | n.d. | n.d. |
| HCIK | n.a. | n.a. | 0.39 ± 0.06 | n.d. | n.d. | n.d. | n.d. |
| HCAZ | n.a. | n.a. | 0.62 ± 0.03 | n.d. | n.d. | n.d. | n.d. |
| HCSE | n.a. | n.a. | 0.61 ± 0.04 | n.d. | n.d. | n.d. | n.d. |
| HCCKE | n.a. | n.a. | 0.03 ± 0.06 | n.d. | n.d. | n.d. | n.d. |
| HCDN | n.a. | n.a. | 0.15 ± 0.00 | n.d. | n.d. | n.d. | n.d. |
| HCFOH | n.a. | n.a. | 0.48 ± 0.00 | n.d. | n.d. | n.d. | - |
| HCFT | n.a. | n.a. | 0.99 ± 0.29 | n.d. | n.d. | n.d. | - |
| Mean | n.a. | n.a. | 0.42 ± 0.26 | 3.33 ± 4.22 | 0.91 ± 1.35 | 0/53 positive response | 0/55 positive response |
| Cut-off | n.a. | n.a. | 0.94 | 11.77 | 3.60 | | |

FIG. 20B

| Patient ID | Disease stage | Disease activity | Serum antibodies | $T_H1$ | $T_H17$ | Direct B cell test | Indirect B cell test |
|---|---|---|---|---|---|---|---|
| WII150911 | CIS | non-active | 0.75 ± 0.15 | 0.00 ± 0.00 | 0.00 ± 0.00 | - | + |
| KII150911 | CIS | non-active | 1.28 ± 0.41 | 0.00 ± 0.00 | 0.00 ± 1.10 | - | - |
| BAII071011 | CIS | non-active | 1.69 ± 0.26 | 3.5 ± 0.5 | 0.00 ± 0.00 | - | - |
| JII071011 | CIS | non-active | 0.00 ± 0.07 | 0.00 ± 0.00 | 23.5 ± 2.48 | - | + |
| BBII071011 | CIS | non-active | 1.84 ± 0.17 | 1.00 ± 0.75 | 3.00 ± 2.50 | - | - |
| EII071011 | CIS | non-active | 0.70 ± 0.18 | 2.00 ± 0.13 | 0.00 ± 0.00 | - | + |
| SII071011 | CIS | non-active | 1.07 ± 0.26 | 0.00 ± 0.00 | 19.00 ± 11.30 | - | - |
| CII261011 | CIS | non-active | 1.84 ± 0.17 | 0.00 ± 0.00 | 0.00 ± 0.00 | - | - |
| BII261011 | CIS | non-active | 1.76 ± 0.05 | 0.00 ± 0.00 | 10.00 ± 2.04 | - | + |
| BII121111 | CIS | non-active | 0.14 ± 0.10 | 0.00 ± 0.00 | 1.25 ± 1.25 | - | - |
| SII250212 | CIS | non-active | 0.39 ± 0.04 | 0.00 ± 0.05 | 0.00 ± 0.00 | - | - |
| BBII100312 | CIS | active | 0.50 ± 0.17 | 0.00 ± 2.00 | 0.00 ± 1.00 | + | - |

FIG. 21

| Patient ID | Disease stage | Disease activity | Serum antibodies | $T_H1$ | $T_H17$ | Direct B cell test | Indirect B cell test |
|---|---|---|---|---|---|---|---|
| MIII200911 | RRMS | active | n.d. | 0.00 ± 0.00 | 0.00 ± 0.00 | positive | negative |
| RIII071011 | RRMS | non-active | 2.22 ± 0.40 | 0.00 ± 0.46 | 0.00 ± 0.00 | negative | positive |
| AIII121111 | RRMS | non-active | 0.16 ± 0.47 | 0.00 ± 0.00 | 2.00 ± 1.22 | negative | positive |
| GIII211012 | RRMS | non-active | 2.31 ± 0.10 | 22.50 ± 7.50 | 33.5 ± 0.50 | negative | positive |
| BUIII250212 | RRMS | non-active | 0.34 ± 0.06 | 0.00 ± 0.00 | 0.00 ± 0.25 | negative | positive |
| BAIII100312 | RRMS | non-active | 1.07 ± 0.30 | 0.00 ± 0.00 | 0.00 ± 0.00 | negative | positive |
| RIII100312 | RRMS | non-active | 0.62 ± 0.01 | 0.00 ± 0.00 | 0.00 ± 0.00 | negative | positive |
| WIII100312 | RRMS | non-active | 0.90 ± 0.04 | 0.00 ± 0.00 | 0.00 ± 0.00 | negative | positive |
| BIII200312 | RRMS | non-active | n.d. | n.d. | n.d. | negative | positive |
| SIII200312 | RRMS | non-active | n.d. | n.d. | n.d. | negative | positive |
| PIII200312 | RRMS | non-active | n.d. | n.d. | n.d. | negative | positive |

FIG. 22

| Patient ID | Disease stage | Disease activity | Serum antibodies | $T_H1$ | $T_H17$ | Direct B cell test | Indirect B cell test |
|---|---|---|---|---|---|---|---|
| KIV121111 | chronic | non-active | 0.97 ± 0.28 | 1.50 ± 0.50 | 0.00 ± 0.00 | - | - |
| JIV121111 | chronic | non-active | 2.29 ± 0.21 | 0.00 ± 0.00 | 0.00 ± 0.50 | - | - |
| RIV121111 | chronic | non-active | 0.07 ± 0.22 | 0.00 ± 0.00 | 0.00 ± 0.00 | - | - |
| BBIV210112 | chronic | non-active | 0.33 ± 0.08 | 0.00 ± 0.00 | 0.00 ± 0.00 | - | - |
| TIV211012 | chronic | non-active | 0.83 ± 0.19 | 1.50 ± 2.00 | 0.00 ± 0.00 | - | - |
| KIV211012 | chronic | non-active | 0.20 ± 0.08 | 9.00 ± 10.75 | 0.00 ± 0.00 | - | - |
| BAJV211012 | chronic | non-active | 0.42 ± 0.08 | 21.00 ± 2.50 | 0.00 ± 0.00 | - | + |
| PIV040212 | chronic | non-active | 0.75 ± 0.04 | 0.00 ± 0.00 | 0.00 ± 0.00 | - | + |
| BIV090212 | chronic | non-active | 0.24 ± 0.03 | 0.00 ± 0.00 | 2.50 ± 1.25 | - | + |
| PIV090212 | chronic | non-active | 0.65 ± 0.04 | 0.00 ± 0.00 | 0.00 ± 0.00 | - | + |
| FIV250212 | chronic | non-active | 0.00 ± 0.02 | 0.00 ± 0.00 | 0.00 ± 0.00 | - | + |
| EIV250212 | chronic | non-active | 0.28 ± 0.05 | 0.00 ± 0.00 | 0.00 ± 0.00 | - | - |

FIG. 23

WHOLE BRAIN LYSATE ANTIGEN-SPECIFIC MEMORY B CELL AND ANTIBODY ASSAYS IN MULTIPLE SCLEROSIS

CLAIM OF PRIORITY

This application is a United States National Phase application filed under 35 U.S.C. 371 of PCT International Application No. PCT/US2012/000232, filed 3 May 2012, which claims priority under 35 U.S.C. 119 to U.S. Provisional Application No. 61/482,365 filed May 4, 2011, entitled "CNS Antigen and Myelin-Specific B Cell, T Cell and Antibody Responses are Diagnostic, Prognostic, and Therapeutic Biomarkers of Multiple Sclerosis," Inventors Paul V. Lehmann and Stefanie Kuerten. Both of these applications are incorporated herein fully by reference.

SEQUENCE LISTING

This application contains a sequence listing. The ASCII .txt file (SEQUENCE LISTING ST25.txt), was originally filed Dec. 9, 2013 with the priority PCT application, and contained 3,305 bytes based on use of single letter nomenclature for the amino acid sequences. The Sequence Listing was amended on Mar. 28, 2014 and contained 11,626 bytes, reflecting the use of three-letter nomenclature for the amino acid sequences. The Sequence Listing (SEQUENCE_LISTING_ST25_26_Ocbober_2021.txt) was amended to be 11,808 bytes in size, because the title was lengthened and use of a second line to finish the title. The amino acid sequence information in the ASCII text file copy submitted via EFS-Web is identical to that filed with the original application as required by 37 C.F.R. 1.821-1.825, and 37 C.F.R. 1.821(c) and 1.821(f). The Sequence Listing complies with 37 C.F.R. 1.824(a)(2)-(6) and (b). The text file will serve as both the "Sequence Listing" required by 37 C.F.R. 1.821(c) and the CRF required by 37 C.F.R. 1.821(e), and the statement of identity under the "Legal Framework" is not required. The sequence listing is incorporated herein fully by reference into the application as required by 37 C.F.R. 1.121(b)(3) and 1.125. As required by 37 C.F.R. 1.825(a), no new matter is being introduced by virtue of the amended sequence listing.

FIELD OF THE INVENTION

This invention relates generally to assays for central nervous antigens, and their uses in diagnosis, prognosis and treatment of multiple sclerosis (MS). Particularly, this invention relates to methods and assays for immune cells and antibodies as diagnostic, prognostic or therapeutic biomarkers of MS. More particularly, this invention relates to detection in the blood of B lymphocytes, antibodies and T-lymphocytes that are sensitive to central nervous system (CNS) antigens.

BACKGROUND

Multiple sclerosis (MS) is considered to be an autoimmune disease of the central nervous system. The disease is characterized by remarkable intra- and inter-individual heterogeneity and has remained highly unpredictable. While in a majority of patients autoreactive T-cells and B-cells/autoantibodies are detectable in CNS demyelinative lesions, there are also subpopulations of patients, in which a primary oligodendrogliopathy is evident. It is known that the responsiveness to immune modulatory treatment can differ remarkably between patients.

SUMMARY

To date, there is no possibility of predicting whether a patient presenting with clinically-isolated syndrome (CIS) or radiologically-isolated syndrome (RIS) will develop definite MS. There is also no possibility of predicting the course of disease in MS patients, and in particular whether and when a patient in clinical remission will develop a relapse. In addition, it is assumed that several subpopulations of MS exist, and the contribution of CNS antigen, and in particular myelin-reactive B and T cells differ in these subpopulations. While in a majority of patients autoreactive T-cells and B-cell/autoantibodies are detectable in CNS demyelinative lesions, there are also subpopulations of patients, in which a primary oligodendrogliopathy is evident. This difference in response is likely to result from the aforementioned differences in immune pathogenesis underlying the disease. So far, there are also no methods available that permit the prediction of treatment responsiveness in MS patients.

In certain embodiments, measurements of CNS antigen/myelin-specific T-cells B-cells/antibodies in the blood after in vitro stimulation of these T-cells and B-cells with CNS/myelin antigen in the presence or absence of mitogen can permit the prediction of: (a) whether a patient with CIS or RIS is likely to transit into definite MS, (b) whether a patient with MS is likely to show disease relapse in the near future, and/or (c) whether a patient with CIS, RIS or MS is likely to respond to/benefit from immune modulatory treatment. Thus, embodiments of this invention include methods wherein immune reactivity to CNS/myelin antigens can be detected in the blood and/or serum/plasma of subjects with multiple sclerosis (MS) or subjects at risk to develop the disease, in particular patients with clinically-isolated syndrome (CIS) or radiologically-isolated syndrome (RIS). The detection of such immune responses has diagnostic and/or prognostic value.

BRIEF DESCRIPTION OF THE FIGURES

The patent or application file contains at least one drawing executed in color. Copies of this patent or patent application publication with color drawing(s) will be provided by the Office upon request and payment of the necessary fee.

This invention is described with respect to specific embodiments thereof. Other features of this invention can be appreciated and understood with reference to the Figures, in which:

FIG. 1A shows lack of MP4 staining in a medium control. FIG. 1B shows the presence of MP4 staining in a patient with MS. FIG. 1C depicts another control and FIG. 1D depicts lack of staining for MP4 in a healthy control subject. Incubation of peripheral blood mononuclear cells (PBMCs) isolated from the blood and stimulated with CNS antigen leads to antibody production by CNS antigen-specific B-cells and immune precipitation in the well in MS patients, but not in healthy controls. This reaction is antigen-specific and does not occur in the absence of antigen.

FIGS. 2E-2H depict photographs of assays in which medium controls (FIGS. 2E and 2G) show no reactivity for MP4. In contrast, FIG. 2F shows immunoreactivity for MP4 in patients with MS, but not in healthy control subjects (FIG. 2H).

FIG. 3A depicts lack of immunoreactivity for IL-17 in medium controls. In contrast, SJL and B6 mice were either immunized with PBS (n=8 mice per group) or the respective CNS antigen (n=16 SJL mice immunized with PLPp, n=14 B6 mice immunized with MOGp) in complete Freund's adjuvant (CFA). 200 ng of pertussis toxin was given on the day of immunization and 48 h later. On day 10 after immunization, blood was obtained from the tail vein, then PBMCs were isolated and tested for their respective CNS antigen-specific for IL-17 (FIG. 3A; black circles) response in double-color ELISPOT assays. Circles refer to the results obtained from individual mice, while bars denote the mean value±SD for each group. Whereas in PBS/CFA-immunized SJL and B6 mice a CNS antigen-specific response was absent (spot numbers were typically <3 spots per $10^6$ cells tested), clear-cut responses were evident in PLPp- and MOGp-immunized mice for both IFN-γ and IL-17. All results are medium-subtracted and normalized to $10^6$ cells.

FIG. 3B depicts representative results of two independent experiments. (B-G) Representative well images of single- and double-color IFN-γ/IL-17 ELISPOT assays performed with PBMCs isolated from the blood of PLPp-immunized SJL mice 10 days after immunization. PBMCs were tested in the absence (medium) and presence of antigen (PLPp). In the presence of medium alone (top row; panels B, C, and D), no spots were observed, whereas in the presence of PLPp, IFN-γ (panel E), IL-17 (panel F) or both IFN-γ and IL-17 together (panel G), easily observable spots were detected.

FIGS. 4A and 4B) or 10, 25 and 40 (B6 mice; FIGS. 4C and 4D) after immunization, PBMCs were obtained from blood, spleen and drLNs, then tested for their antigen-specific IFN-γ (FIGS. 4A and 4C) and IL-17 (FIGS. 4B and 4D) production in single- and double-color ELISPOT assays. The number of spots obtained in the single-color assay was highly correlated to the results in the double-color assay for each cell sample. A total of n=30 SJL mice and n=17 B6 mice were tested in four and three independent experiments, respectively. All results are medium-subtracted and normalized to $10^6$ cells.

FIG. 5A also shows the antigen-specific IFN-γ and IL-17 response measured on day 10 after immunization and the subsequent maximal disease severity.

FIG. 5C depicts the correlation between the magnitude of the MOGp-specific IFN-γ (white circles) and IL-17 (black circles) responses (vertical axis) and the maximal onset severity in B6 mice (horizontal axis). Each circle refers to an individual mouse. Results are representative of two independent experiments performed. All results are medium-subtracted and normalized to $10^6$ cells.

The magnitudes of the PLPp-specific IFN-γ and IL-17 responses were assessed in each individual mouse (FIGS. 6A-6L) on both time points in double-color ELISPOT assays. Open circles refer to IFN-γ and black circles to IL-17 (right vertical axis). The shaded areas denote the clinical score course (left vertical axis) over time after PLPp-induced EAE (horizontal axis). Results are medium-subtracted, normalized to $10^6$ cells, and representative of two independent experiments. In 10 of the animals, there was an initial high level of spots detected using the double-color assay of this invention. This initial high level of spots correlated with the onset of EAE. As the course of the EAE progressed, and the clinical score decreased (with remission of the symptoms), the number of spots decreased. Thus, there was a direct and substantial correlation between T-Cell responses and clinical disease activity.

FIGS. 7A-7L depict graphs of PLPp-specific T-Cell responses over time (right vertical axis), compared to the clinical relapse (shaded area; left vertical axis) in SJL mice with time after immunization with PLPp-induced EAE (horizontal axis). Open circles refer to IFN-γ and black circles to IL-17 (right vertical axis). Disease relapse is accompanied by a re-increase of PLPp-specific T-cell frequencies in PLPp-induced EAE of SJL mice. The legend for FIG. 6 above applies except that the n=12 individual mice (FIGS. 5A-5L) were tested on days 20 and 30 after immunization, corresponding to clinical remission and relapse, respectively. In 10 of these animals, there was a direct correlation between IFN-γ producing T-Cells, IL-17 producing T-Cells and clinical disease activity.

FIGS. 8A-8J depict graphs of IFN-γ and IL-17 producing T-Cells (right vertical axis) and the chronic disease course (shaded areas; left vertical axis) versus time after immunization of 10 individual B6 mice inoculated with MOGp. MOGp-induced EAE is paralleled by stable frequencies of MOGp-specific T-cells. N=10 individual B6 mice (FIGS.

8A-8J) were immunized with MOGp. PBMCs were isolated on days 10, 25 and 40 after immunization, reflecting the pre-onset, peak and chronic stage of the disease, respectively.

The magnitudes of the MOGp-specific IFN-γ and IL-17 responses were assessed in each individual mouse (FIGS. 8A-8J) on all time points in double-color ELISPOT assays. White circles refer to IFN-γ and black circles to IL-17. The shaded areas denote the clinical disease course over time. Results are medium-subtracted, normalized to $10^6$ cells, and representative of three independent experiments.

Figures 9A, 9C, 9E:
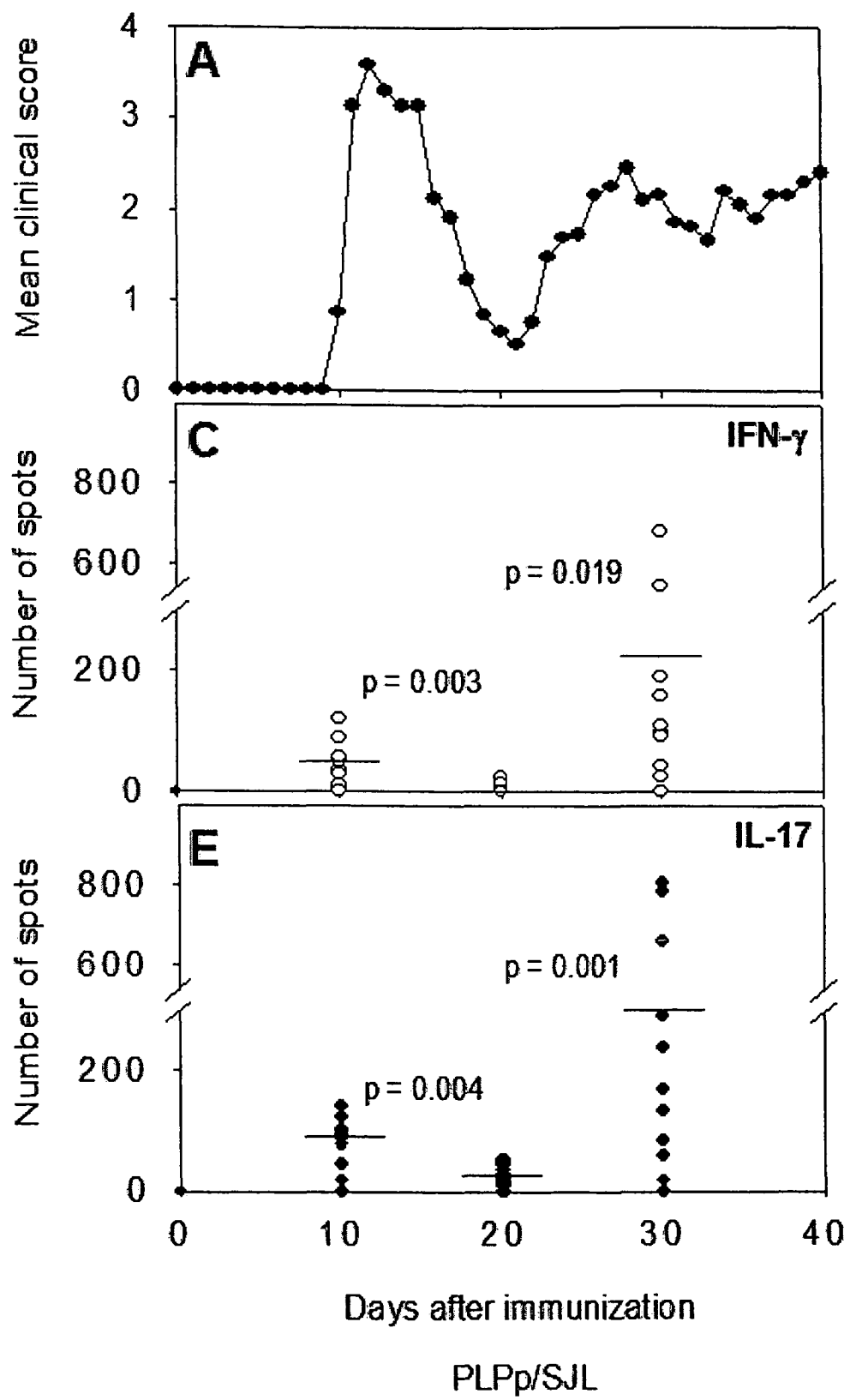
Figures 9B, 9D, 9F:
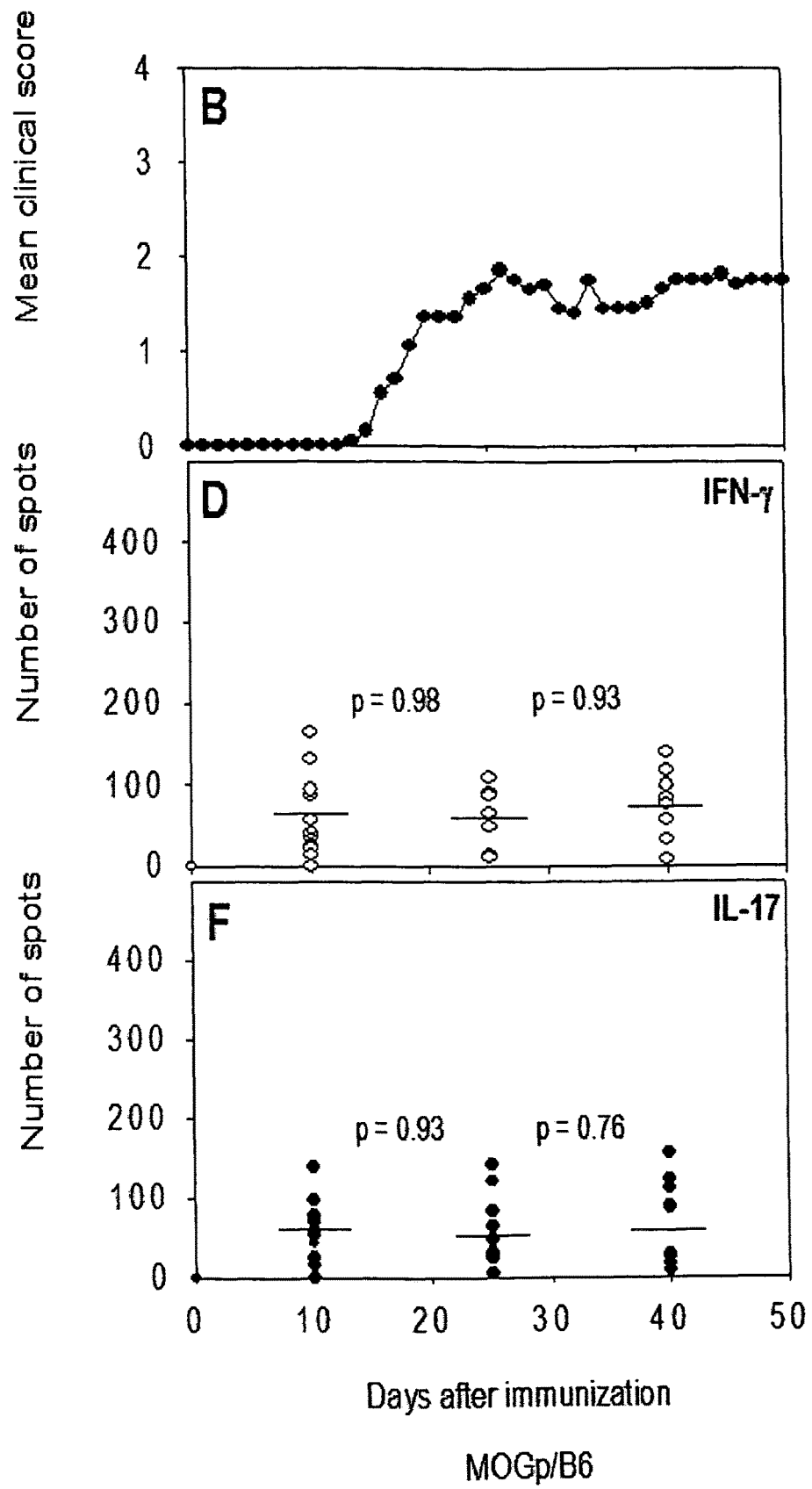

FIGS. 9A-9F depicts graphs of antigen-specific IFN-γ and IL-17 response versus time after immunization in the blood of PLPp- and MOGp-immunized SJL/J (FIGS. 9A, 9C and 9E) and B6 (FIGS. 9B, 9D, and 9F) mice, respectively. In FIGS. 9A, 9C and 9E, SJL/J mice were immunized with PLPp. EAE scores were assessed daily (FIG. 9A). On days 10, 20 and 30 150 μl of blood was obtained from the tail vein, PBMCs were isolated and tested for their PLPp-specific IFN-γ (FIG. 9C) and IL-17 (FIG. 9E) responses in double-color ELISPOT assays. In FIG. 9B, B6 mice were immunized with MOGp. EAE scores were assessed daily. On days 10, 25 and 40 150 μl of blood was obtained from the tail vein, PBMC isolated and tested for their MOGp-specific IFN-γ (FIG. 9D) and IL-17 (FIG. 9F) response as above.

These results indicate that PLPp appears to produce larger IFN-γ and IL-17 responses than does MOGp.

Figure 10A:
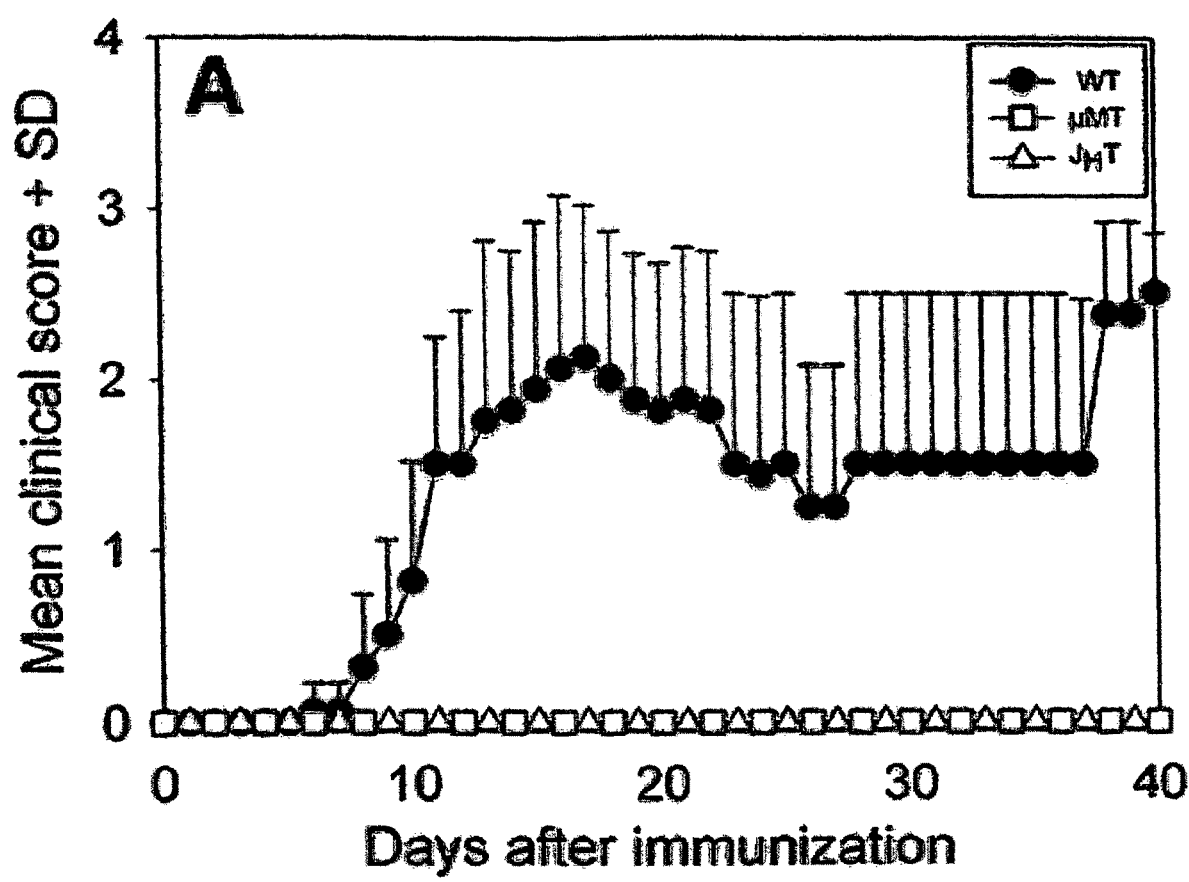

FIGS. 10A-10E depict results observed in B-cell-deficient mice after exposure to MP4-induced EAE. FIG. 10A depicts wild-type mice (WT (n=11; filled circles), μMT (n=8; open squares) and $J_HT$ (n=5; open triangles) mice were immunized with 150 μg MP4 in CFA, pertussis toxin (PTX) was given on days 0 and 2. Clinical scores were assessed daily according to the standard scale. Results are displayed as mean+SD and were reproduced in two additional independent experiments. Wild-type mice showed induction of EAE beginning at about day 8 after exposure. In contrast, μMT and $J_HT$ exposed mice did not develop EAE.

Figures 10B, 10C, 10D, 10E:
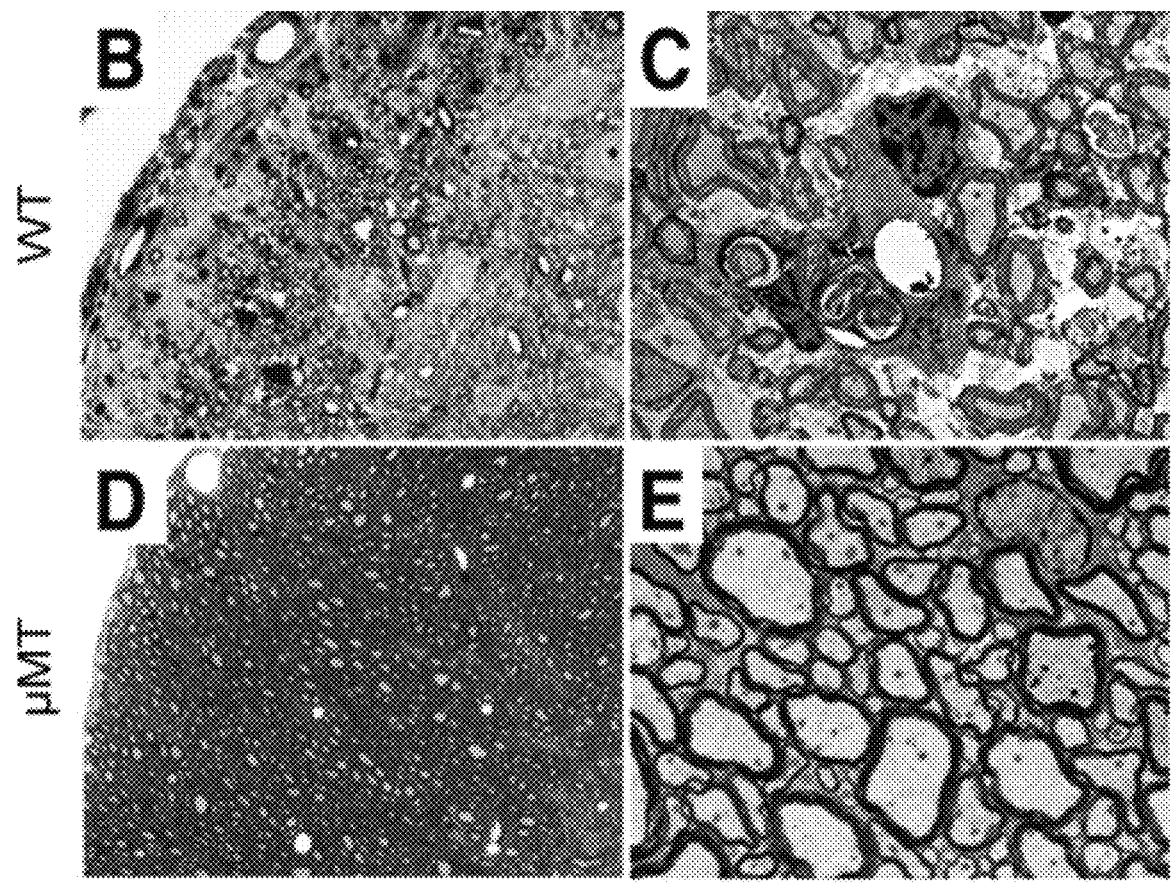

FIGS. 10B-10E depict representative histological images on day 40 after immunization for WT (FIGS. 10B and 10C) and B cell-deficient μMT mice (FIGS. 10D and 10E). FIGS. 10B and 10D depict methylene-blue stained sections at 200× magnification. FIGS. 10C and 10E depict electron microscopic images at 3000× magnification.

Figure 11A:
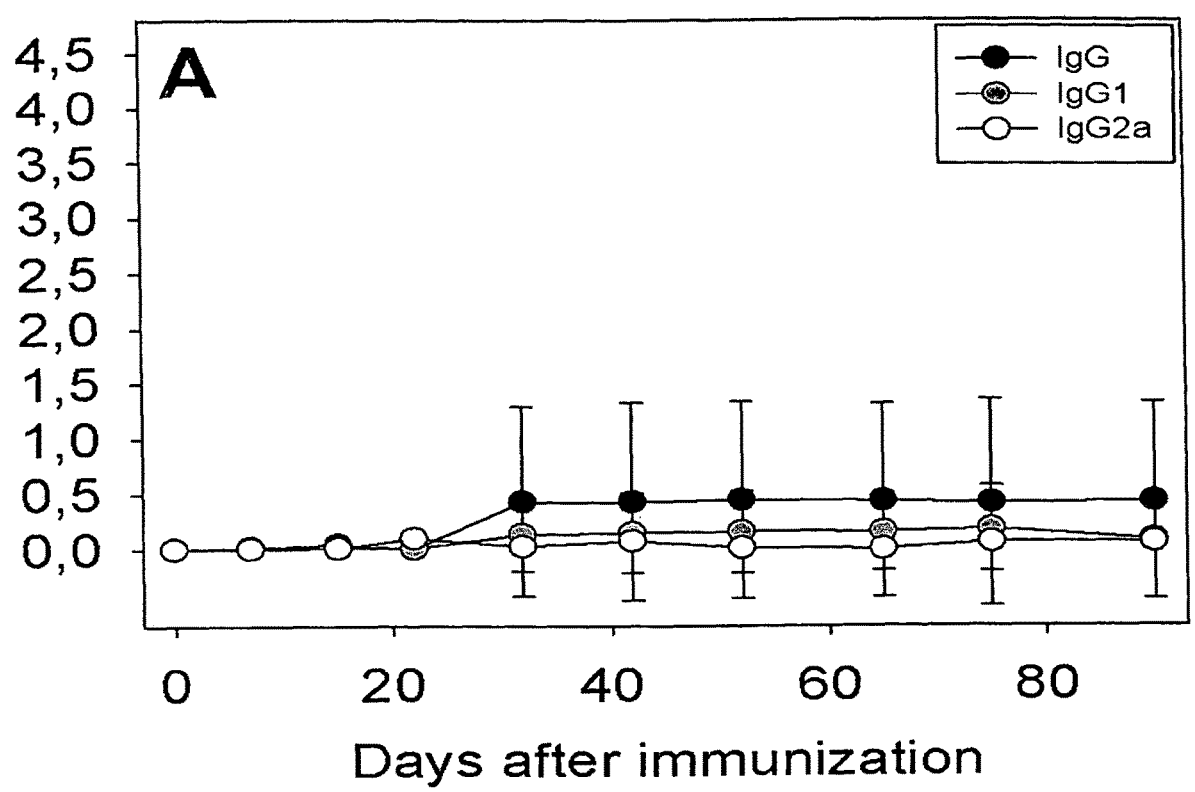
Figure 11B:
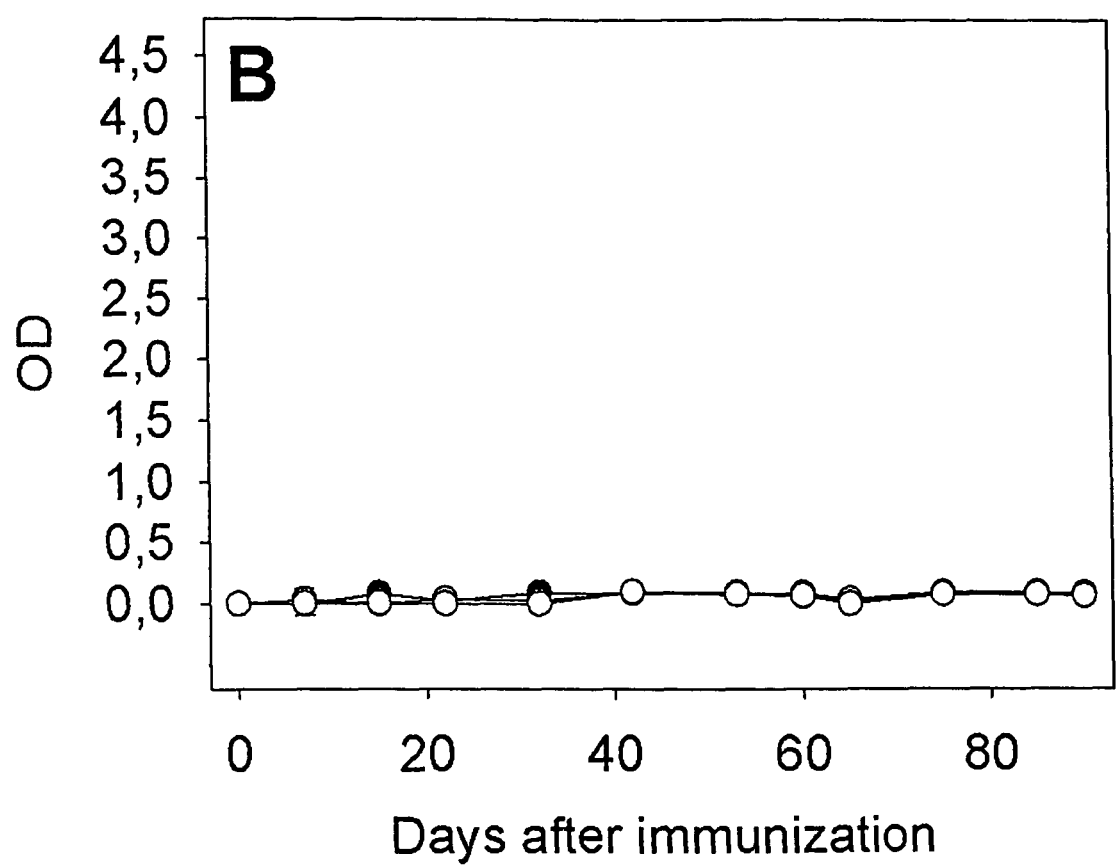
Figure 11C:
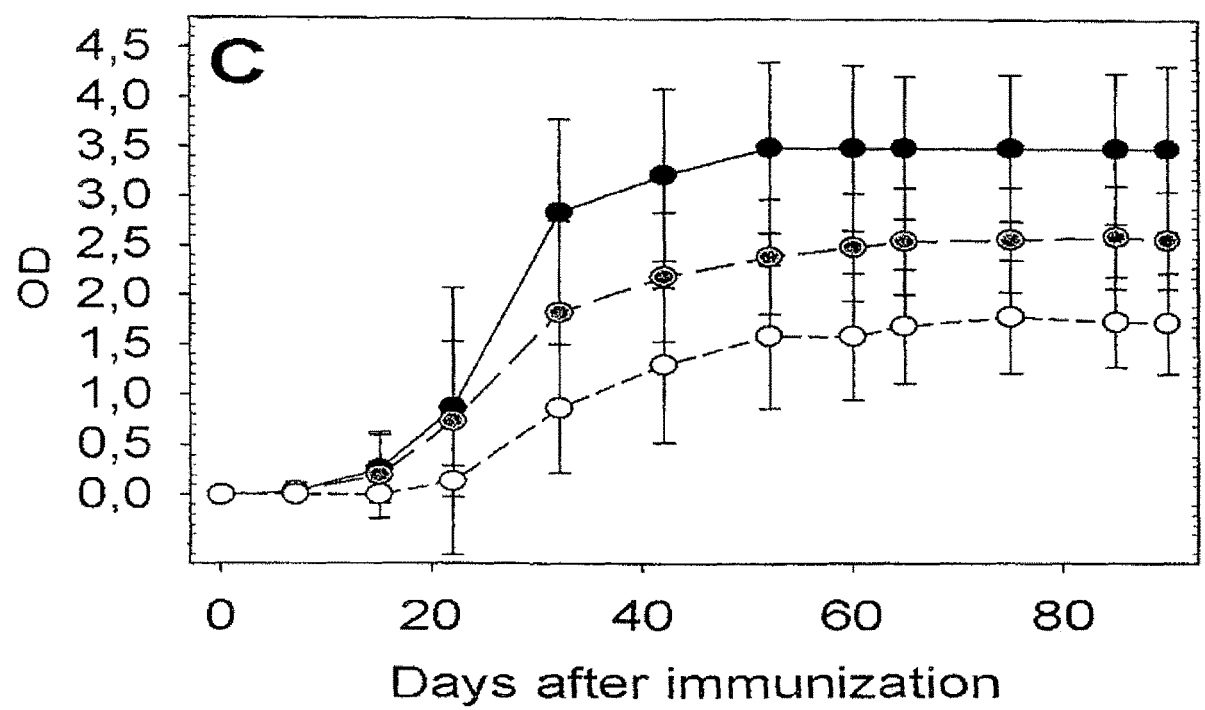

FIGS. 11A-11C depict graphs of optical density (vertical axis) of ELISA assays of immunoglobulins IgG (filled circles), IgG1 (hatched circles) and IgG2a (open circles) versus days after immunization (horizontal axis). FIG. 11A depicts results for WT B6 mice immunized with MOG peptide 35-55. FIG. 11B depicts results for μMT-treated mice immunized with MOGp 35-55. FIG. 11C depicts results in WT B6 mice immunized with 150 μg MP4 in CFA. PTX was given on days 0 and 2. Results are representative for a total of n=8 mice per group. Mean values±SD are shown.

Figure 12A:
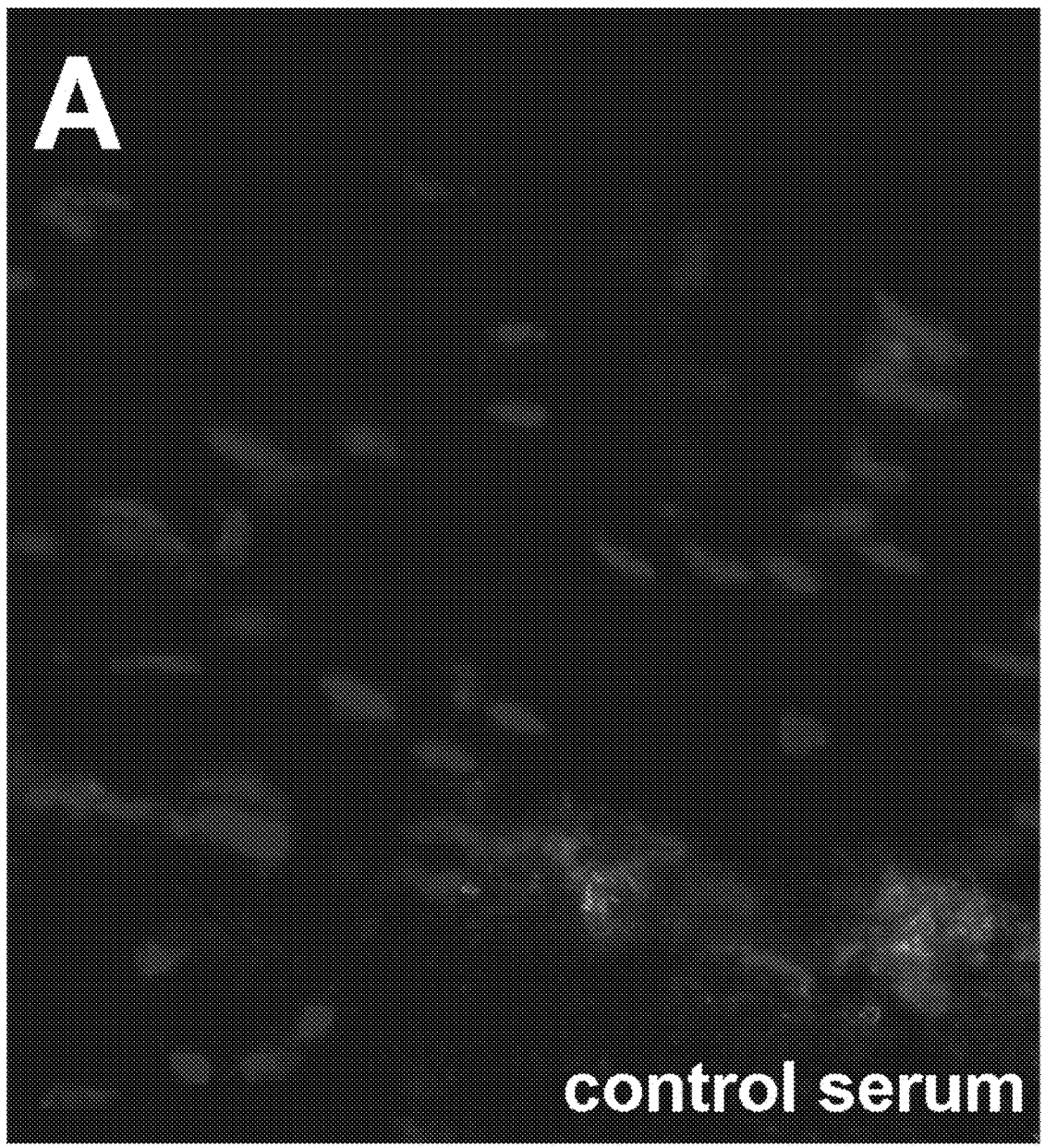
Figure 12B:
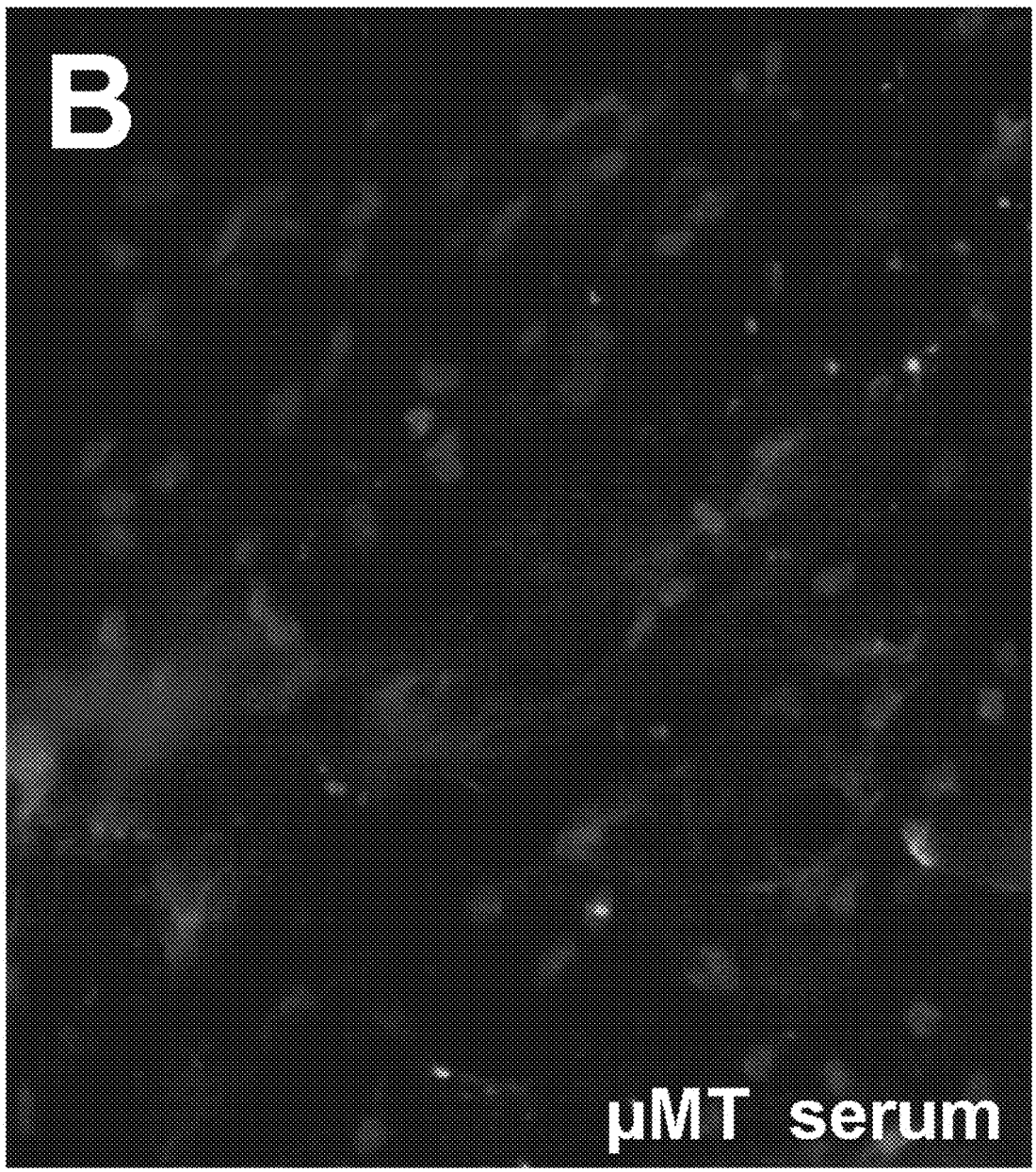
Figure 12C:
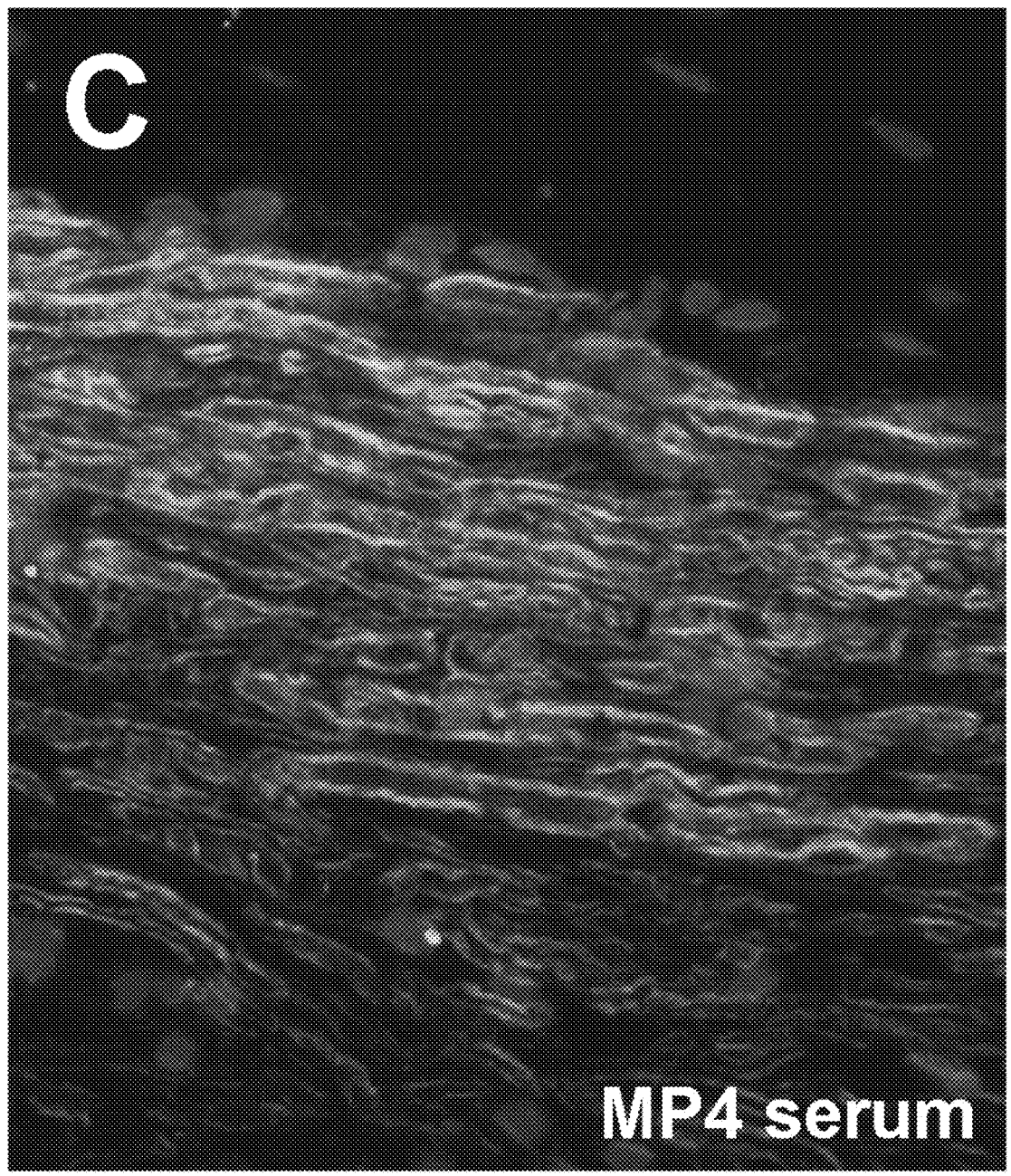

FIGS. 12A-12C depict photomicrographs of 7 μm thick longitudinal sections of spinal cords from mice. FIG. 12A depicts a photomicrograph of spinal cord from a naive, control wild-type B6 mouse treated with serum from a MOGp 35-55 immunized B6 mouse. FIG. 12B depicts a section of spinal cord from an animal treated with serum from an MP4-immunized μMT-treated animal. FIG. 12C depicts a section of spinal cord from a B6 wild-type mouse treated with serum from a wild-type B6 mouse immunized with MP4. In FIG. 12C, bands of myelin are shown, being labeled with antibodies from serum of MP4-immunized mice. The sera had been obtained on day 40 after immunization. All images are at 200× magnification. We conclude that MP4-specific antibodies are myelin-reactive.

FIGS. 13A-13D depict photomicrographs of spinal cords from WT B6 mice immunized with MOG peptide 35-55 (FIGS. 13A and 13B) or MP4 (FIGS. 13C and 13D) showing antibody staining colocalized with demyelinated plaques. WT B6 mice were immunized with MOG:35-55/CFA or MP4/CFA, and PTX was given on days 0 and 2. On day 40 after immunization myelin was stained with anti-MBP antibody (FIGS. 13A and 13C), and the presence of antibody binding was detected by anti-IgG staining (FIGS. 13B and 13D). Results are shown for MOG:35-55- (FIGS. 13A and 13B) and MP4-immunized WT B6 mice (FIGS. 13C and 13D). All images are at 200× magnification and representative for a total of six MOG:35-55- and MP4-immunized mice, respectively. The images refer to MOG:35-55- and MP4-immunized mice having an average clinical EAE score of 2.5.

Figure 14A:
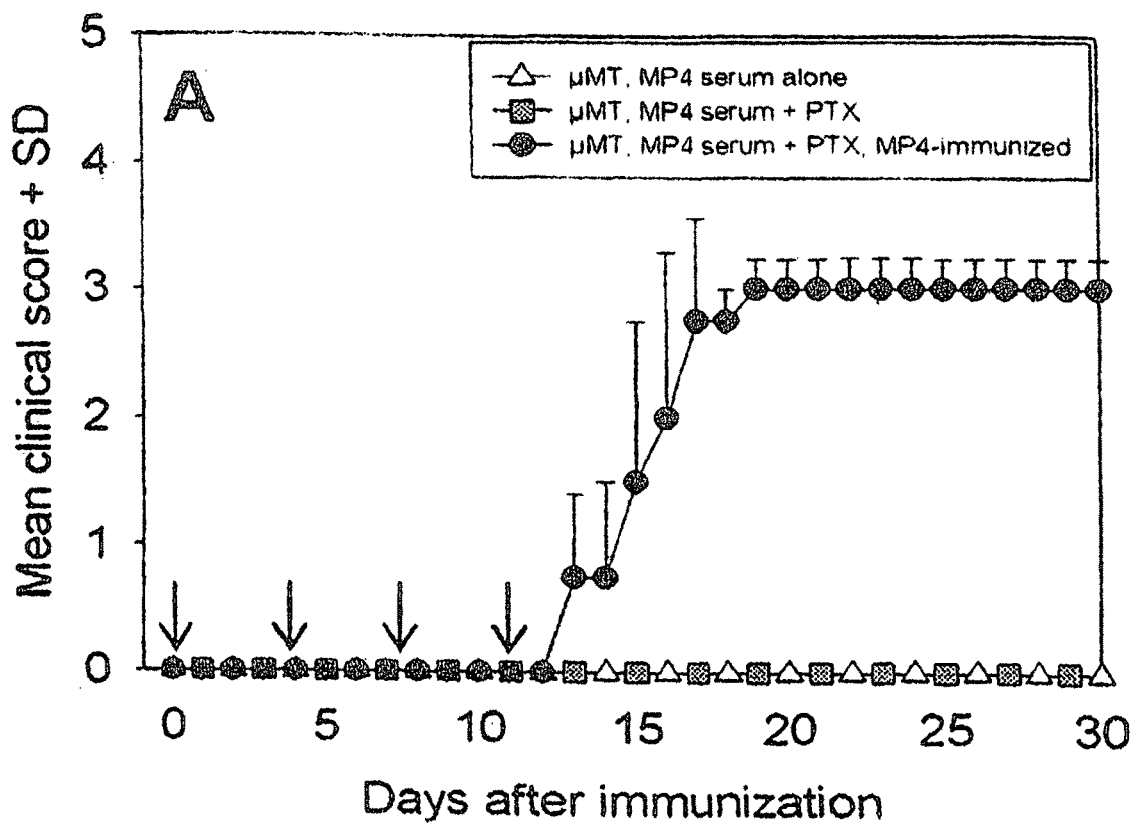
Figure 14B:
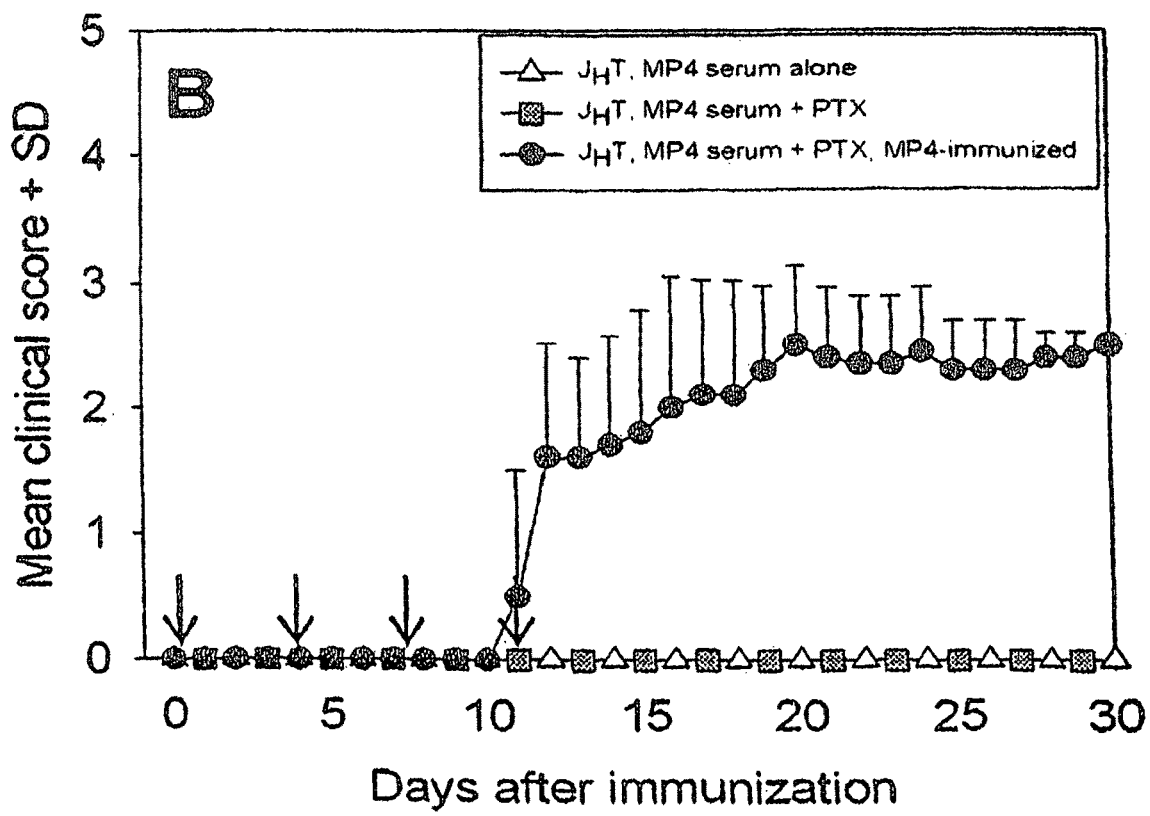
Figures 14C, 14D, 14E, 14F, 14G, 14H, 14I, 14J, 14K:
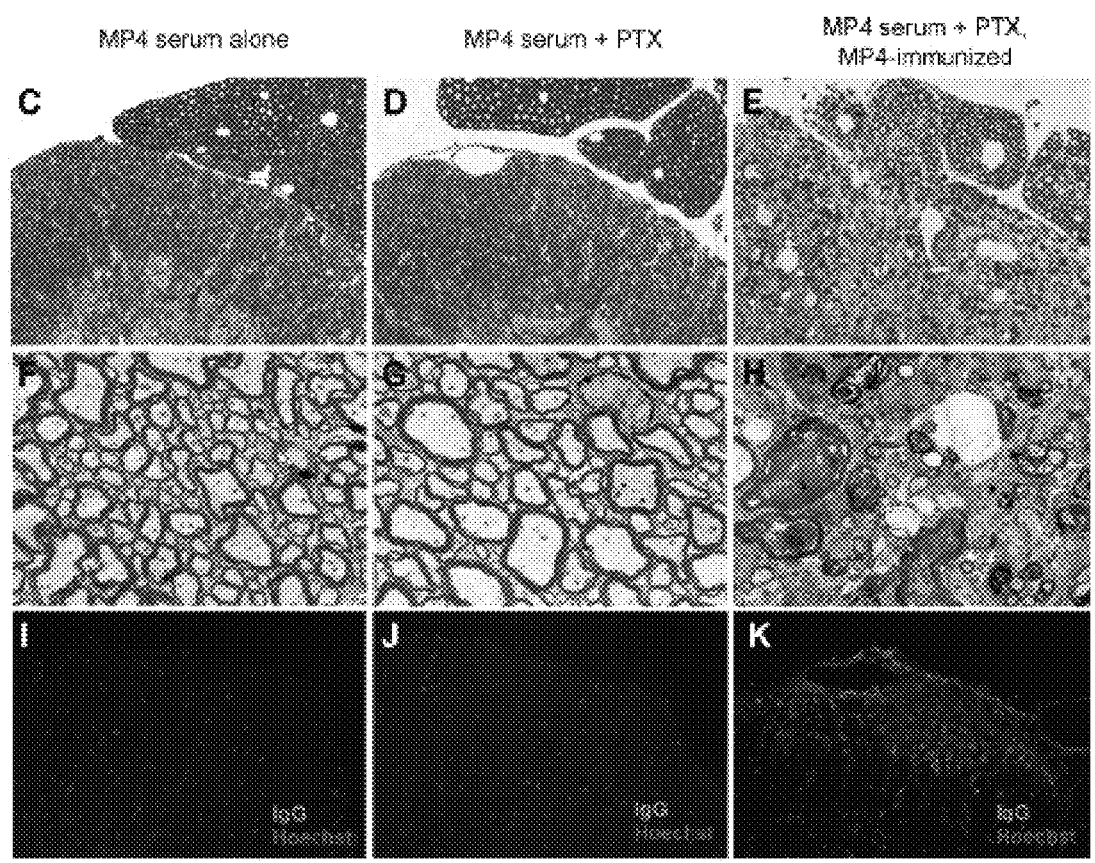

FIGS. 14A-14K depict results of studies that show that transfer of MP4-reactive serum restores disease susceptibility in B-cell-deficient MP4-immunized mice. B-cell-deficient μMT (FIG. 14A) or $J_HT$ (FIG. 14B) mice received 150 μl MP4-specific serum four times within 12 days. Mice either received serum alone (FIGS. 14A-14C, 14F, 14I) or combined with two injections of PTX on the first day of transfer and 48 h later (FIGS. 14A, 14B, 14D, 14G, 14J). A third group of mice was immunized with MP4 in CFA and received both PTX on days 0 and 2 and MP4-specific serum as indicated (FIGS. 14A, 14B, 14E, 14H, and 14K). Clinical scores were assessed daily (FIGS. 14A and 14B). Means+SD are shown. Spinal cord histopathology was assessed on day 30 after transfer. Representative methylene blue-stained sections (200× magnification) (FIGS. 14C-14E) and corresponding electron micrographs (3000× magnification) (FIGS. 14F-14H) are displayed. In addition, spinal cord sections were stained for the presence of IgG depositions (FIGS. 14I-14K).

Figure 15A:
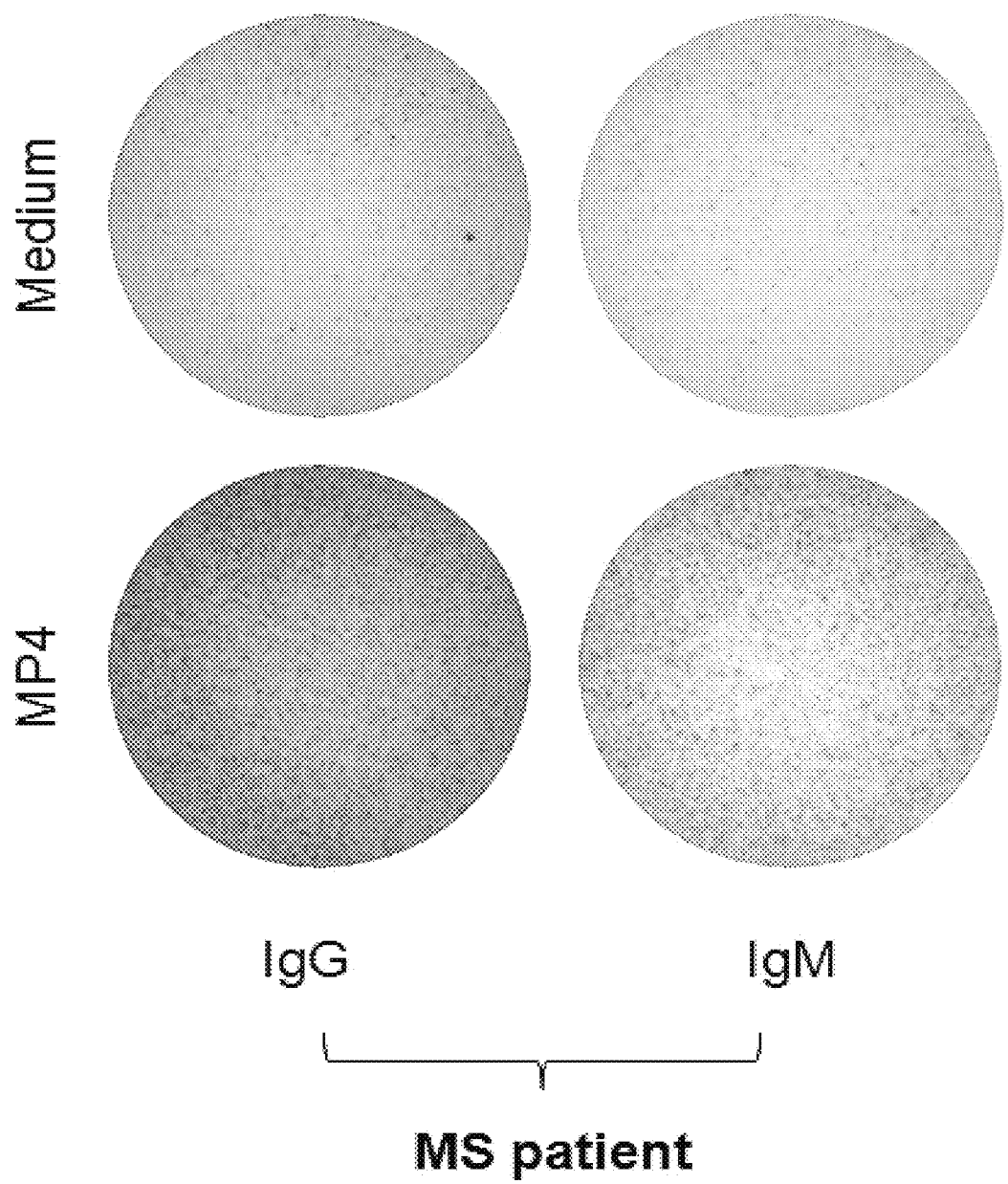
Figure 15B:
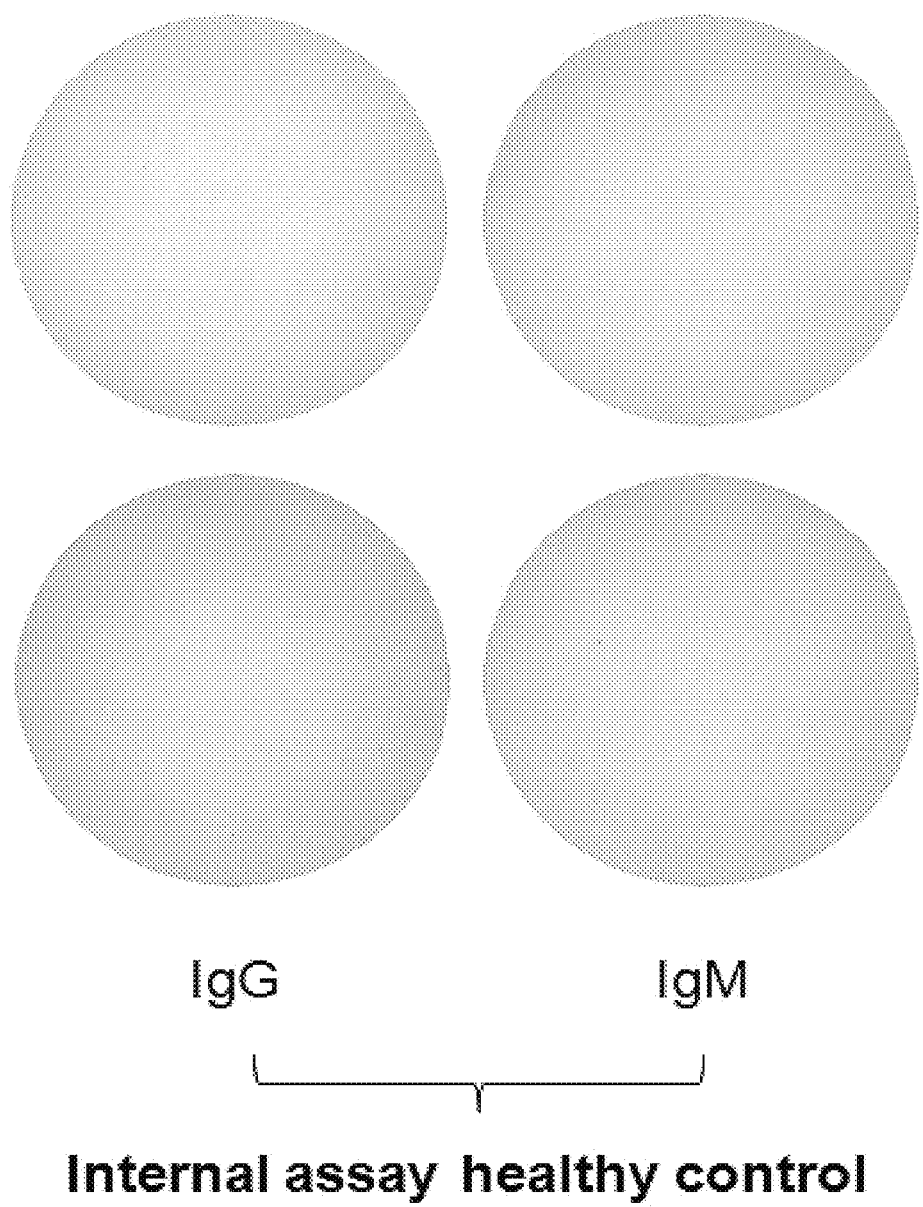

FIGS. 15A and 15B depict photographs of cell culture wells with cells from a patient with MS. Myelin-specific B-cells in MS patients with active disease using a Direct B-Cell assay. FIG. 15A shows that PBMCs isolated from the blood showed myelin-specific antibody secretion in response to MP4 ex vivo. Myelin-specific B-cell responses were observed for both IgG (lower left photograph) and for IgM (lower right photograph). The reaction was antigen-specific, because no responses were observed in response to medium alone (top left and top right photographs.

In contrast, no MP4 responses were observed in PBMCs from healthy controls (FIG. 15B). This reaction is antigen-specific and does not occur in the absence of antigen (medium controls).

Figure 16:
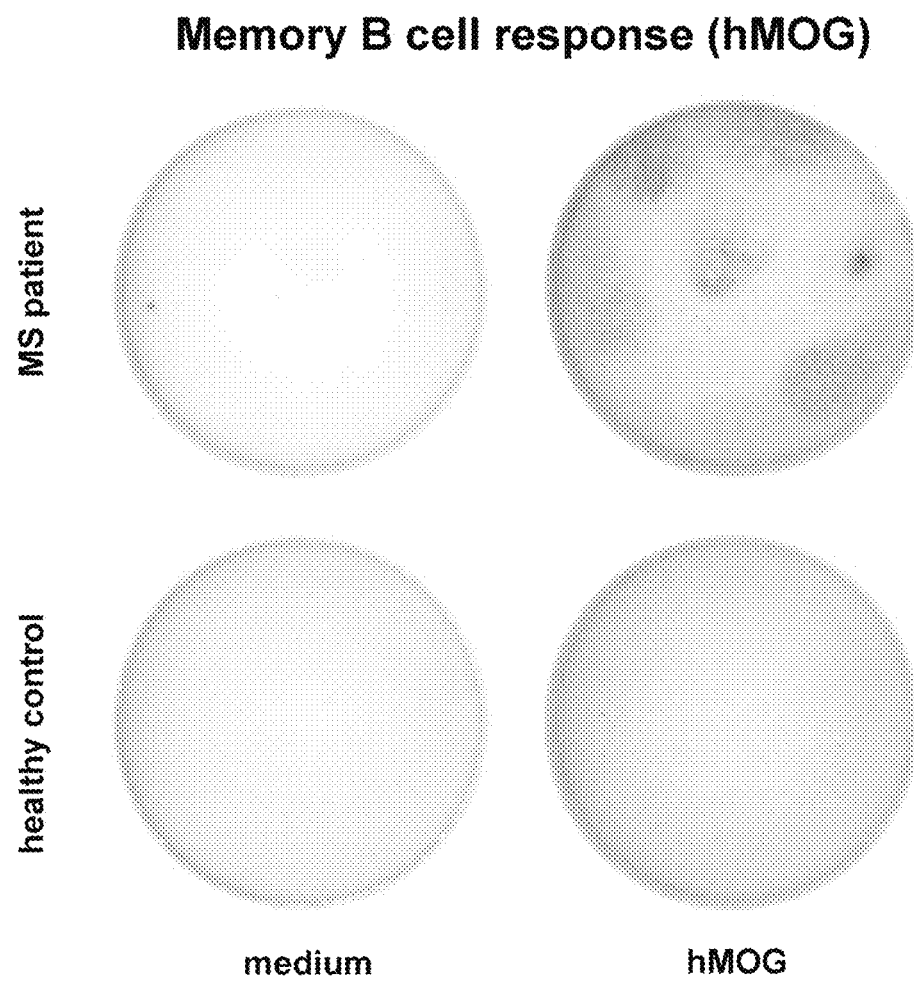

FIG. 16 depicts photographs of cell culture wells with cells therein to show myelin (hMOG)-specific B-cells in MS patients (top two images) and control subjects (bottom images) using an Indirect B-Cell assay of this invention. Polyclonal activation of PBMCs isolated from the blood induced hMOG-specific antibody secretion in the polyclonally stimulated B-cells contained in the PBMC. hMOG-specific B-cells were present in MS patients (top right image), but not in healthy controls (bottom right image). This reaction is antigen-specific and does not occur in the absence of antigen (medium controls; left images).

Figure 17:
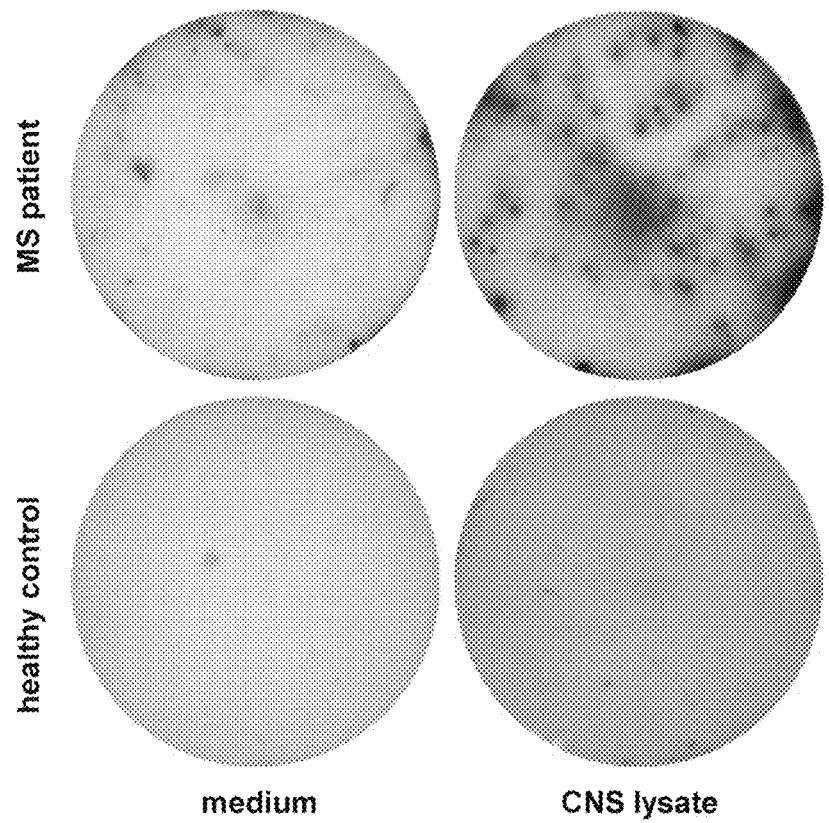

FIG. 17 depicts detection of whole human brain lysate-specific B-cells in MS patients using an indirect B-Cell assay of this invention. Polyclonal activation of PBMCs isolated from the blood induced CNS-specific antibody secretion in the polyclonally stimulated B-cells contained in the PBMC. CNS lysate-specific B-cells were present in a patient having MS (top right image), but not in a healthy control subject (bottom right image). This reaction is antigen-specific and does not occur in the absence of antigen (medium controls; left images).

Figure 18A:
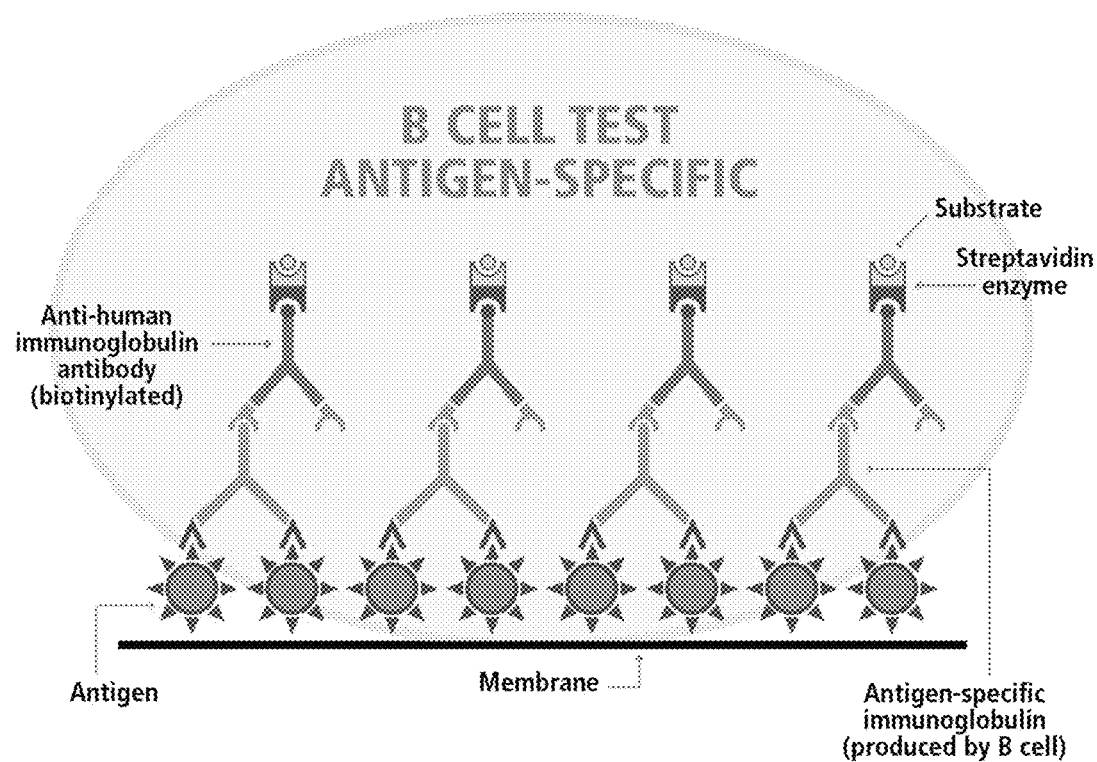
Figure 18B:
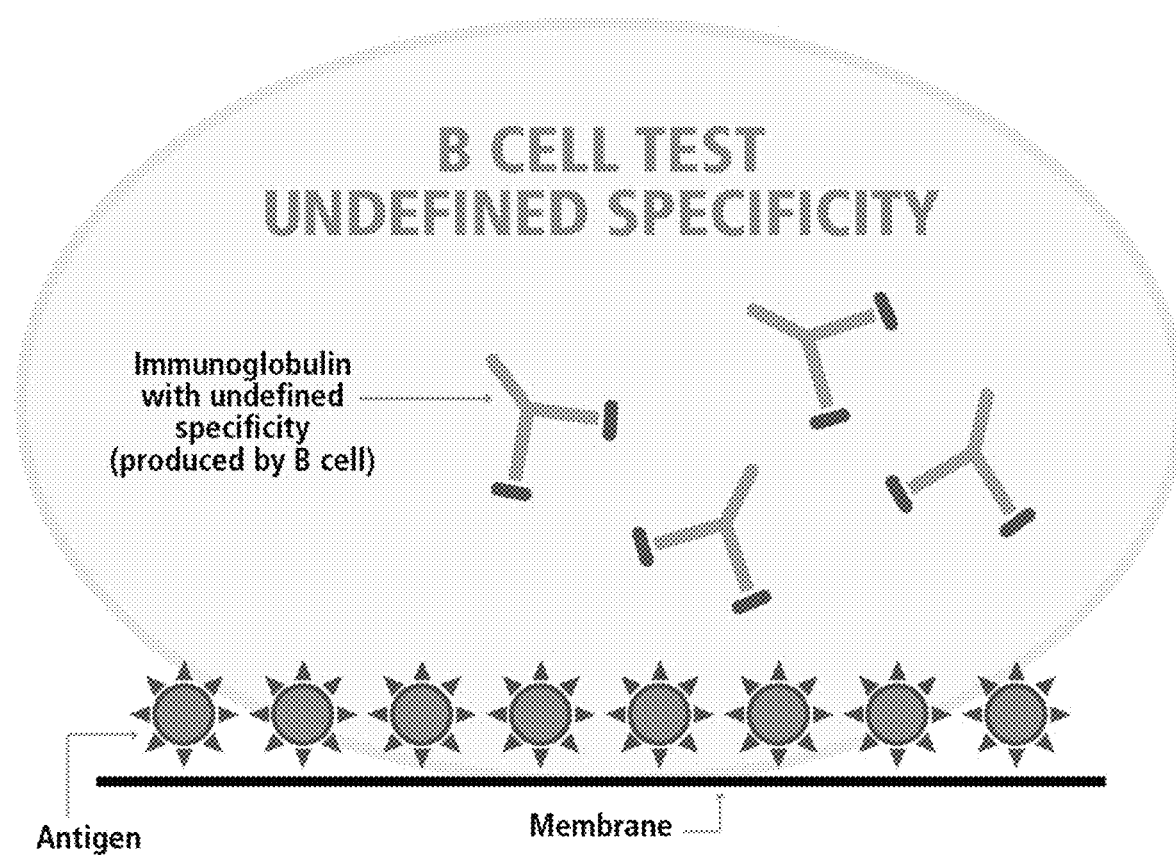

FIGS. 18A and 18B depict methodology of an Indirect B-Cell assay of this invention. FIG. 18A depicts an embodiment 1800 of a B-cell specific embodiment of this invention, having a cell culture well having Membrane 1804 with antigens 1808 attached thereto. Antigen-specific immunoglobulins produced by B-Cells 1812 are shown binding specifically to antigens 1808. Biotinylated anti-human immunoglobulin antibodies 1816 are show attached to antigen-specific immunoglobulins 1812, and streptavidin-enzyme 1820 are shown attached to the biotinylated anti-human immunoglobulin 1816. Substrate 1824 is shown attached to streptavidin-enzyme 1820. Substrate 1824 is acted upon by enzyme to produce a colored reaction product, which can be detected visually.

FIG. 18B depicts an alternative embodiment 1802 of this invention for B-cell tests of undefined specificity. Membrane 1804 and antigen 1808 are shown as in FIG. 18A. Immunoglobulins with undefined specificity produced by B-Cells 1828 are depicted not being attached to antigen 1808. Non-specific antibodies do not bind to the coating antigen and are washed off.

Figure 19A:
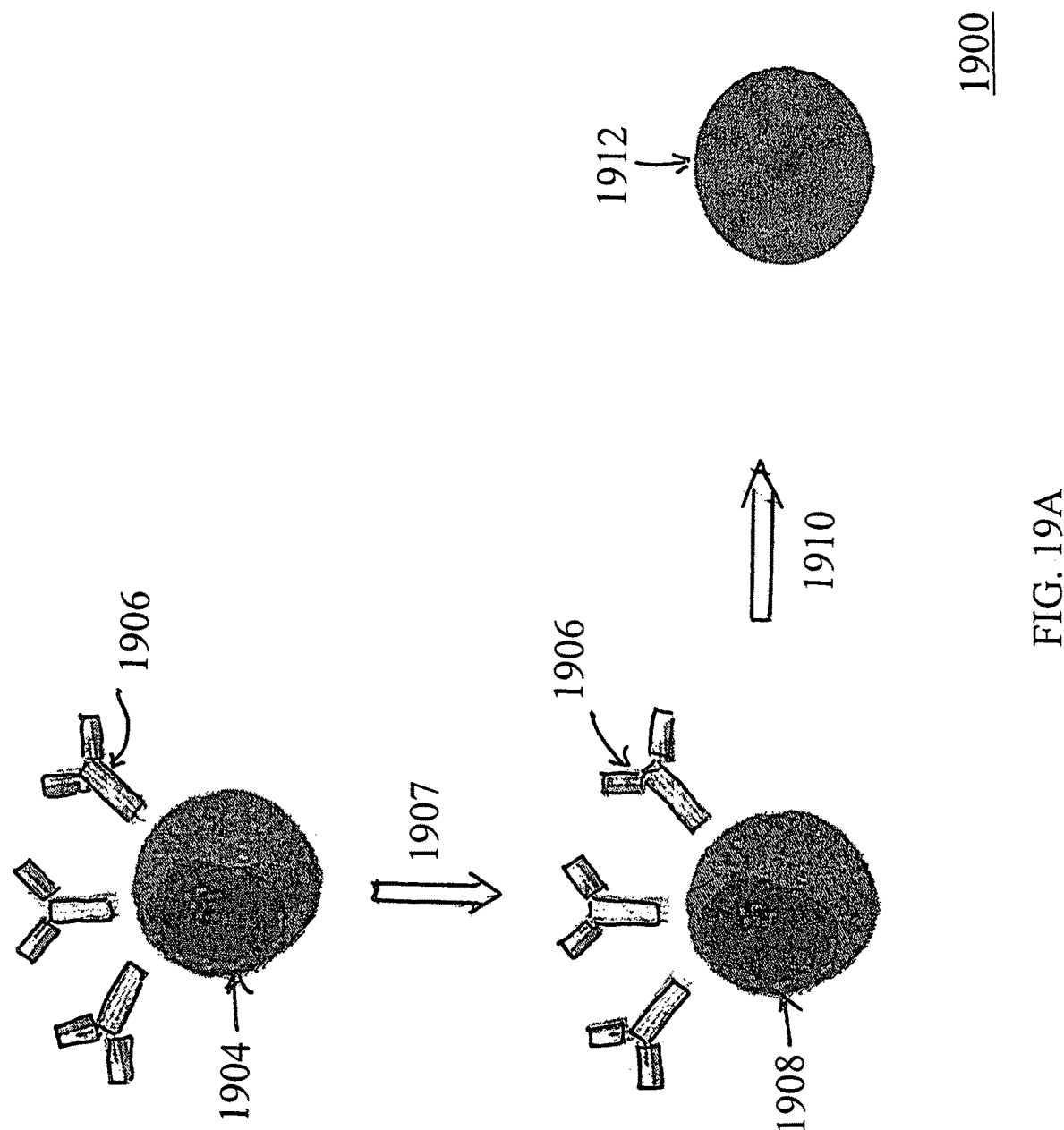
Figure 19B:
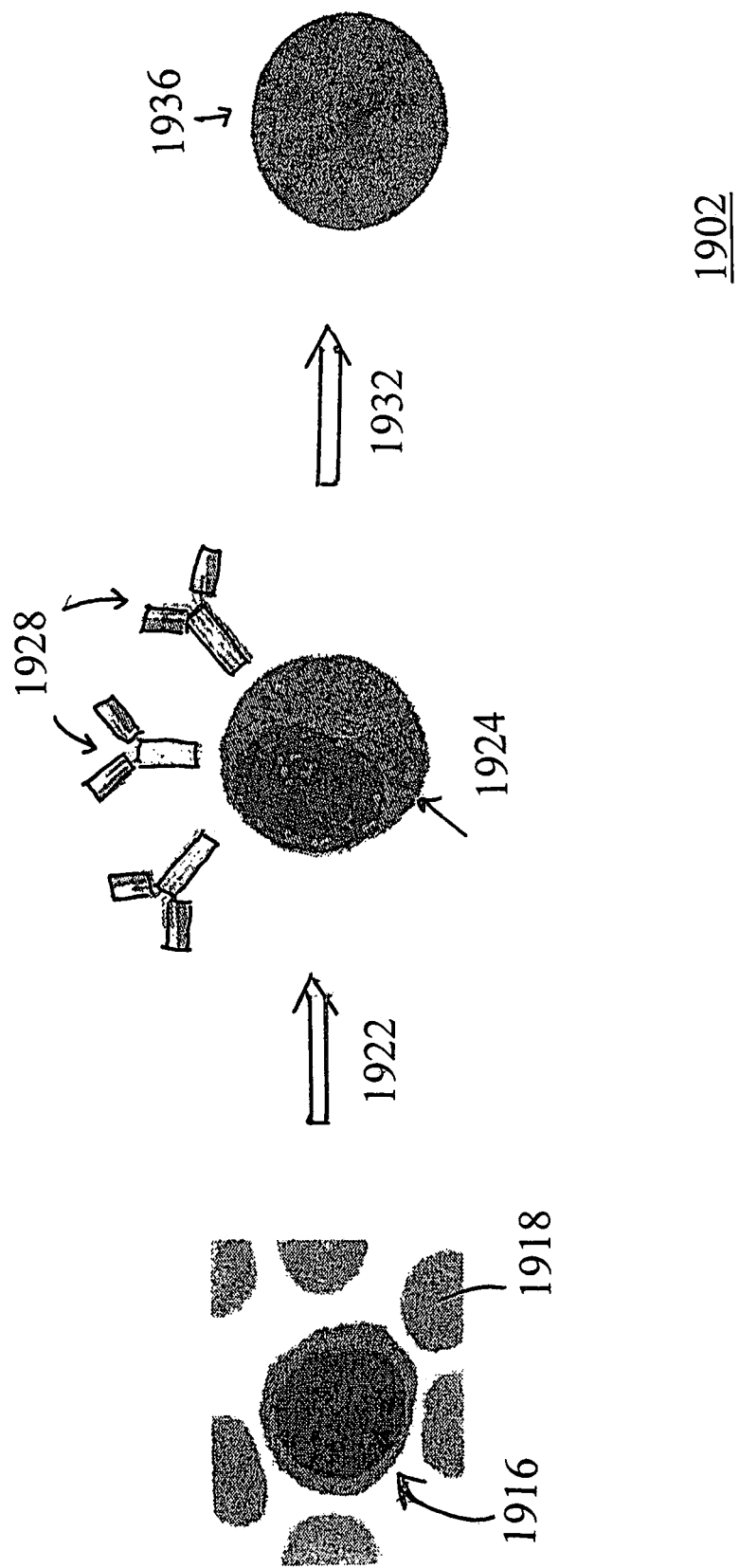

FIGS. 19A and 19B depict summaries of Direct B-Cell (FIG. 19A) assays and Indirect B-Cell assays (FIG. 19B) of this invention. FIG. 19A depicts a "Direct B-Cell assay" 1900 of this invention showing a CNS Plasma Cell 1904 that produces CNS-antigen specific antibodies 1906. CNS Plasma Cell 1904 moves into the bloodstream (at arrow 1907), and is identified as Plasma Cell 1908, which is depicted producing CNS-antigen specific antibodies 1906. Plasma Cell 1908 is then obtained from a sample of peripheral blood mononuclear cells (PBMCs) and placed in a culture well (at arrow 1910). CNS-antigen specific antibodies 1906 are then detected using ELISPOT or similar methods, and show image 1912 having spots indicative of cells that produce CNS-antigen specific antibodies.

FIG. 19B depicts an "Indirect B-Cell assay" 1902 of this invention. Memory B-Cell 1916 is depicted within stroma 1918, and is depicted not producing antibodies. Memory B-Cell 1916 was once in the CNS, where it was responsive to a CNS-specific antigen (not shown; see FIG. 19A). However, Memory B-Cell 1916 migrated into the bloodstream, and became lodged in a B-cell repository in the spleen, lymph node or other site in the immune system. Memory B-Cell 1916 is then released into the bloodstream at arrow 1922. Memory B-Cell 1916 is then drawn along with a sample of PBMCs, which are placed in a culture well. Then, polyclonal stimulation of Memory B-Cell 1916 is accomplished by exposure of the cells to IL-2, R-848, and 2-mercaptoethanol (2-ME or β-ME). Memory B-Cell 1916 is thus stimulated and becomes plasma cell 1924, which produces antibodies 1928. CNS-antigen specific antibodies 1928 are then detected using ELISPOT or similar methods, and show image 1936 having spots indicative of cells that produce CNS-antigen specific antibodies 1928.

FIGS. 20A and 20B depict a table of data obtained from a series of normal subjects without MS.

FIG. 21 depicts a table of data obtained from a series of patients with clinically isolated syndrome (CIS).

FIG. 22 depicts a table of data obtained from a series of patients with relapsing, remitting MS (RRMS).

FIG. 23 depicts a table of data obtained from a series of patients with chronic MS (SP-MS).

Figure 24:
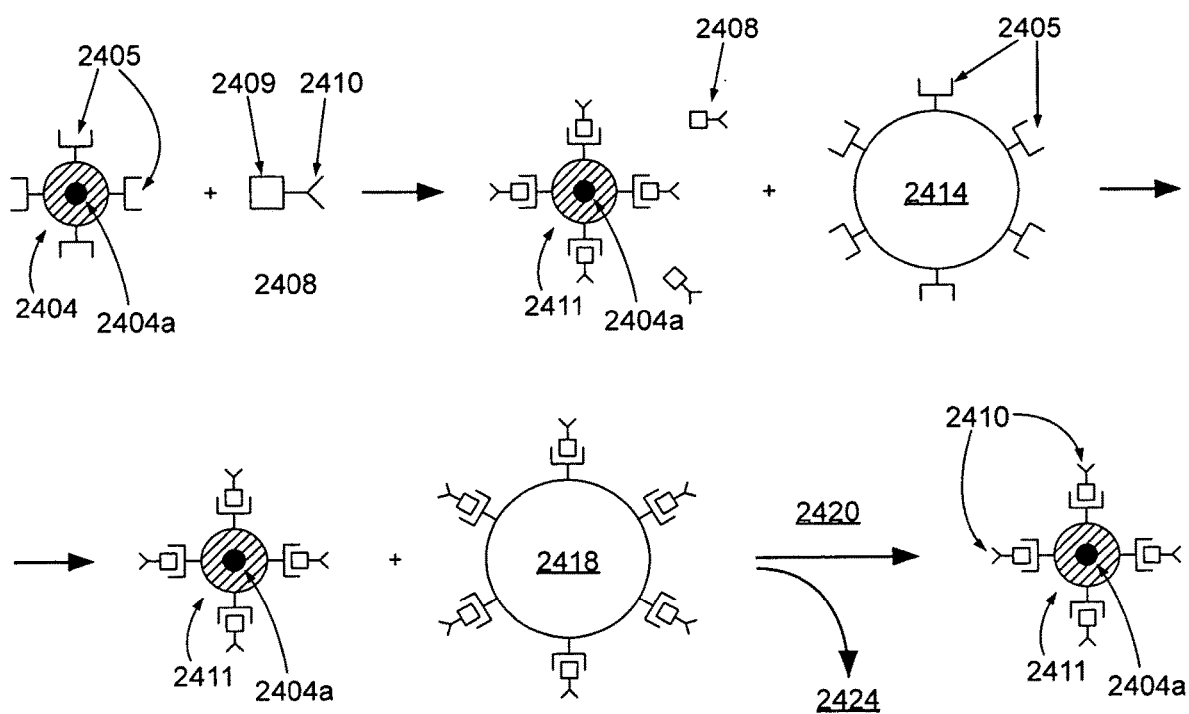

FIG. 24 depicts a diagram of a labeled detection particle useful with methods of this invention.

Figure 25:
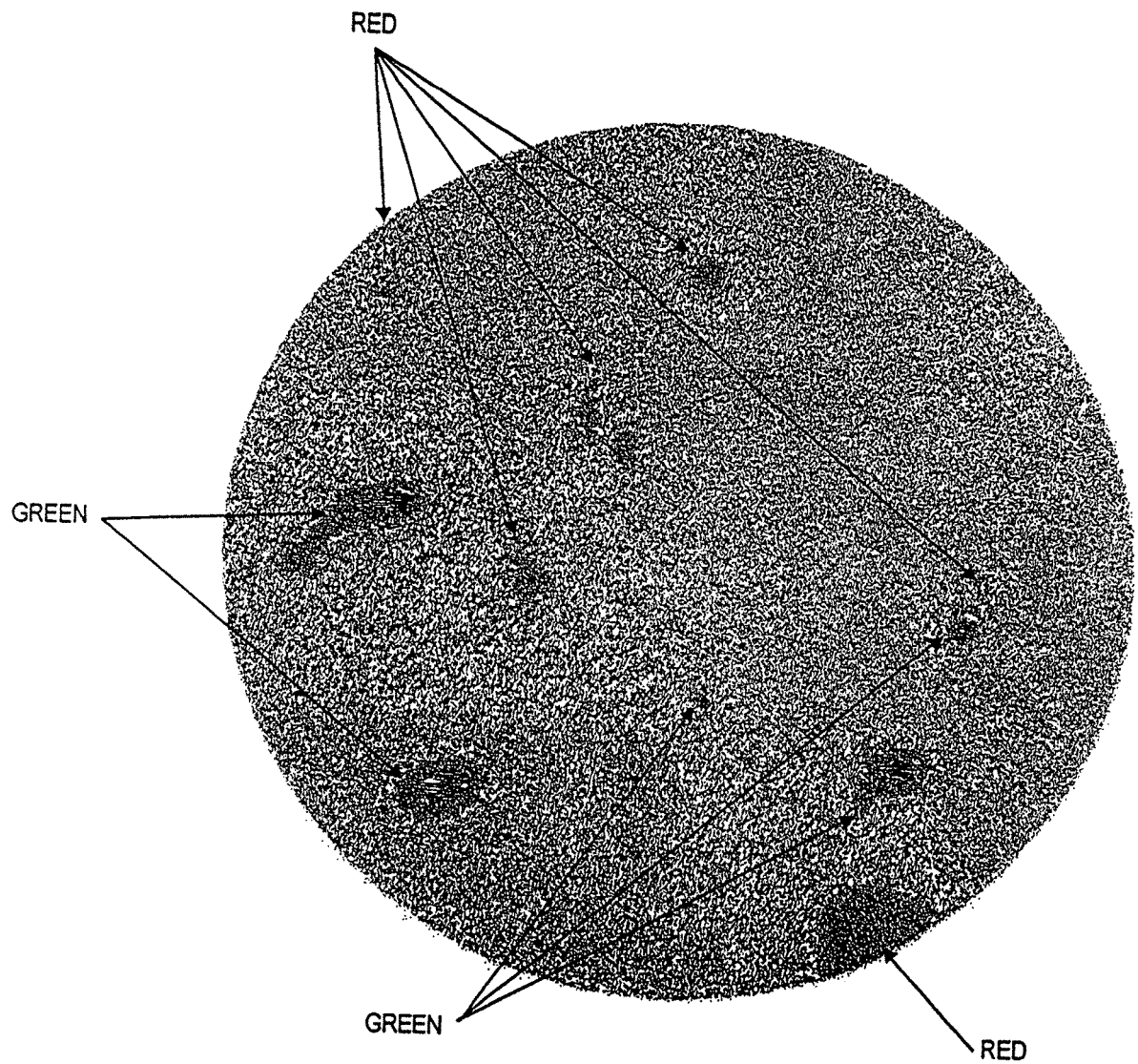

FIG. 25 depicts a photograph of a two-color bead array based assay useful with methods of this invention.

DETAILED DESCRIPTION

Definitions

The following definitions are included for convenience. The meanings of the following terms are to be defined immediately below, unless such term(s) are defined specifically in the sections that follow.

"AP" means alkaline phosphatase.

"APC" or "APCs" means antigen presenting cells.

"BBB" means blood brain barrier.

"B-cells" means B-lymphocytes, including plasmablasts, plasma cells, effector B-cells and memory B-cells.

"β-mercaptoethanol", "2-mercaptoethanol", "2-ME" and "β-ME" means the chemical compound with the formula $HOCH_2CH_2SH$. It can be used for the polyclonal stimulation of B lymphocytes.

"B6" means the murine strain C57BL/6.

"Blood antibodies" means antibodies present in blood/serum, including antibodies against CNS antigen-/myelin-specific responses of white blood cells, in particular B lymphocytes.

"CNS" means central nervous system.

"CNS antigen" means proteins of the central nervous system (CNS), in particular myelin antigens such as proteolipid protein (PLP), myelin basic protein (MBP) or myelin oligodendrocyte glycoprotein (MOG), but also neuronal antigens and additionally, fusion proteins, recombinant proteins or analogues of these proteins, the analogues being defined by their cross-reactivity with the respective antigen-specific antibodies. CNS antigens also include peptides that contain sequences of the protein CNS antigens.

"CNS lysate" means a solution produced when the CNS tissue is disrupted in a process known as lysis. This releases the contents of the tissue. After a crude lysate has been generated, the different components can be separated such as organelles, membrane lipids, proteins and nucleic acids. In this application "CNS lysate" includes proteins derived from CNS tissue. CNS lysate is commercially available or can be prepared following the standard procedures. An example of such a protocol would be to remove the CNS tissue, freeze it in liquid nitrogen and keep it at −70° C. or below until further use. Ice-cold lysis buffer containing Tris, EDTA, Triton X-100 and protease inhibitors is added to the frozen tissue, which is then homogenized on ice. Subsequently, the homogenate is ultracentrifuged and the supernatant isolated. The protein concentration can be determined e.g. by Bradford assay. The supernatant is then stored at −70° C. or below until further use.

"CSF" means cerebrospinal fluid.

"C57BL/6" means a common inbred strain of laboratory mice.

"CD" means cluster of differentiation and refers to cell surface molecules on a cell classifying this cell.

"CFA" means complete Freund's adjuvant and is a mixture of IFA and *M. tuberculosis* strain H37RA.

"CIS" means clinically-isolated syndrome.

"DNA" means deoxyribonucleic acid.

"drLNs" means draining lymph nodes.

"EAE" means experimental autoimmune encephalomyelitis

"ELISA" means enzyme-linked immunosorbent assay.

"ELISPOT" means enzyme-linked immunosorbent spot technique.

"FBS" means fetal bovine serum.

"FITC" means fluoresceinisothiocyanate.

"HL-1" means a chemically defined culture medium containing less than 30 µg protein per ml.

"HRP" means horseradish peroxidase.

"IFA" means incomplete Freund's adjuvant and is a mixture of mannide monooleate and paraffin oil.

"Ig" means immunoglobulin=antibody.

"IL" means interleukin.

"$J_HT$" means a B cell-deficient strain of laboratory mice.

"KO" means genetic knock-out.

"MBP" means myelin basic protein.

"MHC" means major histocompatibility antigens

"MOG" means myelin oligodendrocyte glycoprotein.

"MOGp" means MOB peptide 35-55.

"MP4" means MBP-PLP fusion protein.

"MRI" means magnetic resonance imaging.

"MS" means multiple sclerosis.

"µMT" means a B cell-deficient strain of laboratory mice.

"NMO" means neuromyelitis optica.

"PBMC" means peripheral blood mononuclear cells.

"PBL" means peripheral blood lymphocytes.

"PLP" means proteolipid protein.

"PLPp" means PLP peptide 139-151.

"PPMS" means primary progressive multiple sclerosis. PPMS is characterized by a gradual progression of the disease from its onset with no superimposed relapses and remissions. There may be periods of a leveling off of disease activity. PPMS differs from RRMS and SPMS in that the onset is typically in the late thirties or early forties, men are as likely women to develop it and initial disease activity is often in the spinal cord and not in the brain. Primary Progressive MS often migrates into the brain, but is less likely to damage brain areas compared to RRMS and SPMS—for example, people with PPMS are less likely to develop cognitive deficits. PPMS is the subtype of MS that is least likely to show inflammatory (gadolinium enhancing) lesions on MRI scans. The primary progressive form of the disease affects between 10 and 15% of all people with multiple sclerosis.

"PTx" means pertussis toxin.

"R848" means an imidazoquinoline compound with potent anti-viral activity. This low molecular weight synthetic molecule activates immune cells via the TLR7/TLR8 MyD88-dependent signaling pathway. Recently, R848 was shown to trigger NF-κB activation in cells expressing murine TLR8 when combined with poly(dT). It is used for the polyclonal stimulation of B lymphocytes.

"RPMI-1640" means a cell culture medium for leukocytes and other cell types, RPMI stands for Roswell Park Memorial Institute, where RPMI was developed.

"RIS" means radiologically-isolated syndrome.

"SJL" means Swiss James Lambert and is a common inbred strain of laboratory mice.

"T-cells" means all T effector cell lineages including Th1 and/or Th2- and/or Th9- and/or Th17- and/or Th22-lymphocytes.

"TCR" means T cell receptor.

"$T_H$" means T helper and refers to different types of T-cells.

"TMB" means 3,3',5,5'-Tetramethylbenzidine.

"WT" means wild type.

Multiple Sclerosis

Currently, diagnosis of MS is based on a combination of clinical findings, symptoms, and imaging methods such as magnetic resonance imaging (MRI) Polman et al., *Multiple sclerosis diagnostic criteria: three year later*, Multiple Sclerosis 11:5-12 (2005). Although presence of immunoglobulins in the cerebrospinal fluid (CSF) may be relevant, "MRI has become perhaps the single most informative procedure to contribute to an MS diagnosis." Polman, Id. at 5. A positive MRI test is often probative alone, but the finding of CSF oligoclonal IgG bands) can decrease the stringency of MRI requirements and still fulfill diagnostic criteria. Id. at 6.

Unfortunately, MRI and obtaining CSF are associated with complications. MRI equipment is expensive and is limited to secondary or tertiary care centers, and the tests are costly, time consuming and require patients to come to hospital. Further, interpretation of MRI results requires a high degree of training and sophistication among health care professionals and remain somewhat uncertain, due to interpretation of locations and time-course of development of lesions. CSF analysis requires painful intervention into a patient's CSF compartment, typically via a spinal needle. Additionally, the accuracy of the current "McDonald criteria" is not ideal. False negative results are particularly difficult to address. A false negative result reflects a failure of the diagnostic method to accurately identify MS, and is reflected in a low sensitivity (sensitivity (in %)=[1−false negative rate]×100) One major focus in the art is upon reducing false positive diagnoses to increase selectivity (selectivity (in %)=[1−false positive rate]×100). In general, the lower the threshold for making a diagnosis (increase sensitivity) may lower selectivity. Thus, there is a trade-off between selectivity and sensitivity.

Therefore, we sought to produce simple, cost-effective, safe procedures for diagnosing MS with high selectivity and high sensitivity, especially of those forms of MS that are amenable to treatment (e.g., early in the disease progression), and differentiating between patients for whom immunological and other therapies are likely to be successful from those patients for whom such interventions are less likely to be successful.

We have unexpectedly found that tests of blood, plasma and/or serum for the presence of CNS-specific antibodies, T-lymphocytes, B-lymphocytes and memory B-cells can be effective in diagnosing different forms of MS, predicting progression of MS, and providing guidance for therapeutic intervention.

Immunological Findings in MS

Myelin antigen-reactive antibodies are commonly detected in MS patients (P. Dharmasaroja, J. Neurol. Sci. 206 (2003) 7-16; Y. Qin and P. Duquette, Int. MS J. 10 (2003) 110-120; T. Ziemssen and F. Ziemssen, Autoimmun. Rev. 4 (2005) 460-467; P. Martin Mdel and N. L. Monson, Front. Biosci. 12 (2007) 2735-2749; K. A. McLaughlin and K. W. Wucherpfennig, Adv. Immunol. 98 (2008) 121-149; S. Kuerten et al., Fortschr. Neurol. Psychiatr. 79 (2011) 83-91). The deposition of antibodies in lesions has been found to occur alongside with fixed components of the complement system suggesting that these antibodies have activated complement in situ contributing to inflammation and phagocyte activation (I. I. Ivanov et al., Cell 126 (2006) 1121-33; C. M. Pelfrey et al., J. Immunol. 165 (2000) 1641-1651; R. Hohlfeld and H. Wekerle, Proc. Natl. Acad. Sci. USA 101 (2004) 14599-14606; P. V. Lehmann et al., Nature 358 (1992) 155-157). So-called pattern II lesions that are characterized by the presence of antibodies and complement are the most abundant ones in MS and also found in NMO, a strongly antibody-dependent variant of the disease. Accordingly, plasma exchange showed therapeutic benefit both in type II MS and NMO patients (C. Lucchinetti et al., Ann. Neurol. 47 (2000) 707-717; B. G. Weinshenker et al., Ann. Neurol. 46 (1999) 878-886; M. Munemoto et al., J. Clin. Neurosci. (2011), epub.

Much of our current perception of the pathomechanisms involved in MS has been deduced from studies of EAE. In most EAE models CD4$^+$ T-cells have been found to be required and sufficient to mediate the disease and in many models an involvement of antibodies has been ruled out. An apparent exception is MOG-induced EAE of the B6 mouse. Human MOG protein, but not MOG peptide and rat MOG protein have been shown to entail a pathogenic autoantibody response (A. R. Oliver et al., J. Immunol. 171 (2003) 462-468; C. B. Marta et al., Proc. Natl. Acad. Sci. USA 102 (2005) 13992-13997; J. A. Lyons et al., Eur. J. Immunol.32 (2002) 1905-1913; C. Bourquin et al., J. Immunol. 171 (2003) 455-461). Our data presented herein provide evidence that MOG:35-55-induced EAE can be independent of autoantibodies. In the light of the literature MBP- and PLP-induced EAE are also CD4$^+$ T-cell mediated without a pathogenic antibody contribution (N. T. Potter and T. S. Stephens, J. Neurosci. Res. 37 (1994) 15-22; B. L. McRae and S. D. Miller, Neurochem. Res. 19 (1994) 997-1004; S. S. Zamvil et al., Nature 324 (1986) 258-260; R. B. Fritz et al., J. Immunol. 130 (1983) 191-194). The data we present here, using the MP4 fusion protein that contains both MBP and PLP, does not support that idea.

Proteolipid protein ("PLP") has been shown to be encephalitogenic in several mouse strains (N. T. Potter and T. S., J. Neurosci. Res. 37 (1994) 15-22). However, few studies have been performed with the native PLP protein. Due to its extreme hydrophobicity that results from four transmembranous sequences, it is difficult to isolate and to experimentally work with (V. K. Tuohy, Neurochem. Res. 19 (1993) 935-944). Therefore and because of a relapsing-remitting disease course, PLP peptide 139-151-induced EAE in SJL mice has become the prevalent PLP model. However, because KO mice are not available on the SJL background, it is difficult to dissect the role of antibodies in this model. Also, the PLP peptide 139-151 is located in an intracellular domain of PLP and immunization with the peptide does not elicit antibodies that could bind to the surface of the intact myelin sheath (N. T. Potter and T. S. Stephens, J. Neurosci. Res. 37 (1994) 15-22; B. L. McRae and S. D. Miller, Neurochem. Res. 19 (1994) 997-1004). EAE induced by MBP protein (that is easy to purify and work with) has been studied extensively. Only little and conflicting evidence for a pathogenic role of MBP-specific antibodies has been found in the past (M. Morris-Downes et al., J. Neuroimmunol. 125 (2002) 114-124; Z. Jingwu et al., J. Neuroimmunol. 24 (1989) 87-94). The finding is perhaps not surprising since MBP is buried inside the myelin sheath and thus not accessible to autoantibodies.

In previous work we showed that immunization of µMT mice with MP4 results in a MP4-specific T cell response that is comparable in magnitude to WT mice, yet the µMT mice do not develop severe EAE (S. Kuerten et al., J. Neuroimmunol. 177 (2006) 99-111). Apparently, the MBP/PLP-specific T-cells could not establish inflammatory lesions without the additional involvement of either B-cells or antibodies. Here we show that in MP4-immunized B-cell-deficient mice MBP/PLP-specific antibodies are sufficient to induce EAE of similar course and severity as in the WT mice.

The mechanisms by which MBP/PLP-specific antibodies assert the EAE sensitizing effect in MP4-immunized mice are unclear. Whatever the mechanisms of the MBP/PLP-specific antibodies may be, to our knowledge this is the first demonstration that such antibodies can have a fundamental impact on the development of EAE. In the absence of such antibodies, MBP/PLP-induced EAE does not develop in B6 mice. These data also implicate a role of MBP and PLP as targets of autoantibody-mediated immune pathology in MS. Unlike for T-cells, for antibody-mediated pathology, the abundance of the antigen can be decisive. MBP and PLP are the most abundant myelin proteins. MBP- and PLP-specific antibodies are prevalent in MS and considering the results reported herein, we conclude that such antibodies play a pathogenic role in the human disease.

Multiple Sclerosis and Experimental Autoimmune Encephalomyelitis (EAE)

Multiple sclerosis (MS) is a human disease. It is characterized by progressively developing sensory, neurocognitive and autonomic deficits and weakness of skeletal muscle, with the attendant loss of motor function. It is widely believed that MS may be an autoimmune disorder, in which the body identifies one or more CNS proteins as foreign, and develops immune responses against the cells that express those proteins. Based on this understanding, an animal system has been widely used to study mechanisms and characteristics of the disease in animals, including mice. Such systems are generally termed "Experimental Autoimmune Encephalopathy" or "EAE."

EAE has been widely used to mimic MS. EAE can be produced by administering to mice MOG, MBP, PLP or combinations of these antigens. Additionally fusion proteins can be used to induce EAE. Although the ways in which EAE is induced may vary, they share the common features of human MS. These include progressive sensory and autonomic deficits, muscular weakness, with the resultant loss of motor coordination and function. Thus, studies in animals with induced EAE are predictive of humans with MS.

There are two primary options for immune monitoring in MS. One involves the testing of cerebrospinal fluid itself which, however, cannot easily be done repeatedly and longitudinally in patients. The other one is testing of peripheral blood that, due to its accessibility and the availability of considerable amounts of PBMCs, is the primary site of sampling. For this reason, most data on CNS antigen-reactive T cells in MS have been obtained using PBMCs from the peripheral blood (D. J. Mahad, J. et al., Mult. Scler. 9 (2003) 189-198; B. Bielekova and R. Martin, Brain 127 (2004) 1463-1478; L. Rinaldi and P. Gallo, Neurol. Sci. 26 (2005) S215-S217; M. Reindl et al., J. Neuroimmunol. 180 (2006) 50-62; A. Lutterotti et al., Curr. Med. Chem. 14 (2007) 1956-1965; R. J. Fox et al., Mult. Scler. 14 (2008) 1036-1043; J. Drulovic et al., J. Neuroimmunol. 215 (2009) 90-95; S. Sawai et al., J. Neuroimmunol. 218 (2010) 112-115).

While EAE is generally considered a model for MS, studies of murine blood have so far been limited by the low numbers of cells that can be obtained without jeopardizing the survival of the mice. In the blood of MS patients, it has been challenging to reliably measure CNS antigen-specific T-cells (C. M. Pelfrey et al., J. Immunol. 165 (2000) 1641-1651).

Figure 3A:
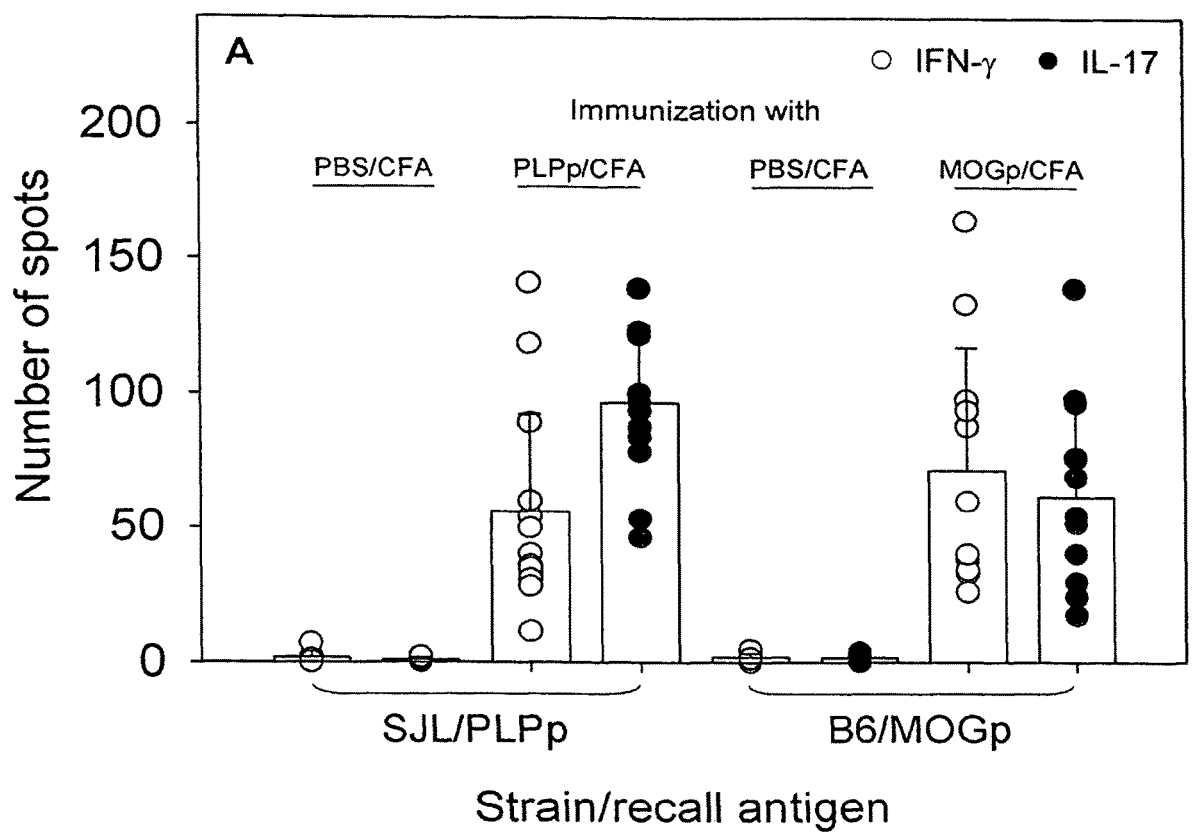
FIGS. 3A and 3B depicts summary data on immunoreactivity for IFN-γ (open circles) and IL-17 (filled circles) responses detected in the blood of immunized mice with and without EAE.

Therefore, we first set out to investigate whether such cells could be reliably detected in the blood of mice undergoing EAE. As shown in FIG. 3A, all immunized mice displayed a specific and clear-cut recall response to the immunizing antigen. Thus, at least in murine blood, there were no inherent limitations for detecting the antigen-specific T-cells. In these mice, however, the identity of the CNS antigen is well defined, being the injected peptide. Moreover, all measurements were done within 40 days after immunization. In contrast, in humans the nature of the primary antigen is not known, and the immunological onset of the disease/the events that triggered initial T-cell responses may have occurred months or years back (C. M. Pelfrey et al., J. Immunol. 165 (2000) 1641-1651, R. Hohlfeld and H. Wekerle, Proc. Natl. Acad. Sci. USA 101 (2004) 14599-14606). In mice, it is well-established that with time, the first wave of autoreactive T-cells induced by immunization exhausts and contracts in clonal sizes while determinant spreading engages and diversifies the autoreactive repertoire (P. V. Lehmann et al., Nature 358 (1992) 155-157; B. L. McRae et al., J. Exp. Med. 182 (1995) 75-85; C. L. Vanderlugt et al., Immunol. Rev. 164 (1998) 63-72; C. L. Vanderlugt et al., J. Immunol. 164 (2000) 670-678; V. K. Tuohy et al., Immunol. Rev. 164 (1998) 93-100). Both these mechanisms may also occur in humans, each complicating the detection of autoreactive T cells in the blood.

In the PLPp/SJL model, we did not find a correlation between the numbers of CNS antigen-specific IFN-γ or IL-17 secreting T-cells prior to EAE onset and the severity of the initial disease episode. This might be explained by the ease with which determinant spreading occurs in these mice: in contrast to MOGp-induced EAE, the PLPp model involves effector cells that are specific for determinants other than PLP:139-151 and that possibly need to be considered in future studies to delineate a correlation with the clinical severity (B. L. McRae et al., J. Exp. Med. 182 (1995) 75-85; C. L. Vanderlugt et al., Immunol. Rev. 164 (1998) 63-72; C. L. Vanderlugt K et al., J. Immunol. 164 (2000) 670-678).

Remarkably, however, the subsequent relapsing-remitting disease course was mirrored by dynamic frequencies of CNS antigen-specific T-cells in the blood. After the acute stage of the disease, the frequencies of the first wave autoreactive T-cells dropped in 10 out of 11 mice (one additional mouse died of EAE), paralleling the clinical recovery from EAE. Previous work has demonstrated that unlike during active primary disease or relapse, in such states of remission, few if any functional T-cells are found in the CNS (H. H. Hofstetter et al. J. Immunol. 174 (2005) 4598-4605; W. S. Begolka et al. J. Immunol. 161 (1998) 4437-4446). Therefore, one might postulate that the drop in T-cell numbers in the blood reflects an actual exhaustion of the first wave of effector cells in SJL mice rather than redistribution towards the CNS. Why this reduction in frequencies and the recovery itself occurs in SJL mice versus the B6 model is unclear. Nevertheless, these results are consistent with the primary effector cell hypothesis, provided this exhaustion of the majority of T-cells also affects those cells engaged by determinant spreading during the first episode of the disease.

It was striking that in parallel to the EAE relapse, massive renewed expansions of PLPp-specific T-cells were seen in 9 out of 10 mice (two additional mice died of EAE). The mechanisms that drive this renewed expansion are unclear, but this expansion could explain the occurrence of the clinical disease exacerbation well. CNS antigen expression in peripheral tissues has been observed (T. M. Pribyl et al., Proc. Natl. Acad. Sci. USA 90 (1993) 10695-10699; T. M. Pribyl et al., J. Neurosci. Res. 45 (1996) 812-819; R. B. Fritz and I. Kalvakolanu, J. Neuroimmunol. 57 (1995) 93-99; N. Kawakami et al., J. Exp. Med. 1999 (2004) 185-197) and could boost the autoreactive T-cells in addition to CNS antigen release from the injured target organ itself (P. V. Lehmann et al. Nature 358 (1992) 155-157; B. L. McRae et al., J. Exp. Med. 182 (1995) 75-85). The breakdown or dysfunction of immune regulatory mechanisms, including regulatory T-cells, may also be suggested (A. L. Astier et al., J. Clin. Invest. 116 (2006) 3252-3257; A. L. Zozulya and H. Wiendl, Nat. Clin. Pract. Neurol. 4 (2008) 384-398; A. Ma et al., Int. Immunopharmacol. 9 (2009) 599-608).

The studies described herein of MOGp-induced EAE provided results that are consistent with a simple pathological mechanism. In contrast to the PLPp/SJL model, we found that the frequencies of both IFN-γ and IL-17 producing T-cells prior to disease onset correlated with the subsequent maximal disease severity. These data correspond to the notion that the CNS antigen-specific T cells may be mediators of the disease. Accordingly, the higher the number of specific T-cells present, the higher the effector potential and the more severe the resulting disease. This type of direct relationship is also known for passive EAE, in which graded numbers of CNS antigen-specific T-cells are injected into naïve recipients (I. M. Stromnes and J. M. Goverman, Nat. Prot. 1 (2006) 1952-1960). In the MOGp model of EAE, the frequencies of the specific T-cells were stable over the observation period and so was the clinical course of the disease. These data might be interpreted to mean that even in chronic disease, the T-cells engaged by immunization (as opposed to those engaged by determinant spreading) continue to be the primary effector cells. This direct relationship does not exclude more complex mechanisms. However, while there is ample evidence for determinant spreading in the PLPp-induced SJL model (C. L. Vanderlugt et al., Immunol. Rev. 164 (1998) 63-72; C. L. Vanderlugt et al., J. Immunol. 164 (2000) 670-678; V. K. Tuohy et al., Immunol. Rev. 164 (1998) 93-100), our literature search did not provide evidence for spreading in the MOGp-induced EAE of B6 mice.

We found that the limited amount of blood available from mice does not prevent systematic studies of the effector cell pool, while offering the possibility of observing the clinical disease in parallel. Thereby, we fill an important gap that has previously hampered immune diagnostic/prognostic research in EAE. This study was not intended to provide detailed insights into the complex immune mechanisms that underlie CNS antigen-induced EAE, including comprehensive studies of cytokine signatures of the effector cells and secondary repertoire dynamics involved in spreading. However, the initial experiments presented here provide a striking observation, namely, that CNS antigen-specific T-cell frequencies in the blood are reflective of the clinical course of EAE. In addition, it has become increasingly clear that effector cell types are not stable, but tend to convert from $T_H17$ to $T_H1$ in vivo (G. Shi et al., J. Immunol. 181 (2008) 7205-7213). By offering the possibility of monitoring such dynamics, our assay can contribute to the identification of the dominant effector cell populations causing pathology in each particular disease stage. As more is learned about the CNS antigens that are actually targeted in MS, our approach should therefore also serve as valuable tool in the quest for more efficient diagnostic and prognostic options in patients where the blood is the primary material that is available for testing.

While attempts have been made to correlate disease activity and cytokine production in blood and cerebrospinal fluid (CSF) of MS patients, results were discouraging and controversy has remained. One of the problems resided in the fact that in most cases cytokine levels were measured, without considering the antigen-specificity of the response.

In addition, longitudinal measurements of antigen-specific T-cell and B-cell responses have not been performed in EAE and MS.

In addition to the involvement of CNS antigen-specific T-cells, about 75% of MS patients show antibody depositions within demyelinative CNS lesions ("pattern II" according to Lucchinetti et al). Accordingly, this patient population greatly benefits from plasma exchange, pointing to a significant pathogenic role of antibodies in the disease. B-cells and the secretion of antibodies by plasma cells have so far largely been neglected as a pathogenic entity of MS. Focus has rather been laid onto the T-cell component of the disease. One of the main reasons for that is that much of our current perception of the pathomechanisms involved in MS has been deduced from studies of EAE. In most EAE models $CD4^+$ T-cells have been found to be required and sufficient to mediate the disease and in many models an involvement of B-cells and antibodies has been ruled out. We have recently introduced the MBP-PLP fusion protein MP4-induced EAE as a novel animal model for MS in C57BL/6 mice (Kuerten et al., 2006). We have shown that MP4-induced EAE is B-cell-/antibody-dependent. B-cell-deficient mice (such as the μMT or $J_H$T strain) are resistant to EAE. However, reconstitution of these mice with MP4-reactive antibodies completely restored disease susceptibility to the level of the wild-type mice (Kuerten et al., 2011; see Example 16).

Cellular and Molecular Diagnosis of MS

CNS antigen-specific B-cells are present in the blood of MS patients in high numbers relative to healthy control subjects, but cannot be detected because they do not produce antibody when there is no acute immune activation and patients are in remission. There are still CNS antigen-specific antibody secreting B-cells in the CNS itself, but these B-cells are likely to remain in the CNS and antibodies secreted by these B-cells will be directly absorbed by the CNS tissue, thus, not recirculating in the blood stream. After B-cell stimulation in vitro with polyclonal activators, however, all B-cells within the PBMC become activated and start producing antibodies. In a subsequent readout system that detects CNS antigen-specific B-cells, one can identify the number of CNS antigen-specific B-cells ("Indirect B-Cell" assay). In patients with acute disease and recent immune activation, B-cells secreting CNS antigen-specific antibodies can be directly detected in the blood without any polyclonal stimulation ("Direct B-Cell" assay). In the experiments described herein, membranes were coated with crude CNS protein lysate containing all CNS antigens or individual recombinant CNS antigens (e.g., MOG or MBP/PLP). When activated B-cells are seeded on top of the CNS antigen-coated membrane, the antibodies produced by CNS antigen-specific B-cells will bind to the membrane around the secreting B-cell and the individual spot forming cells can be enumerated via the ELISPOT technology thus revealing the frequency of CNS antigen-specific B-cells in the cell population of activated PBMCs. Antibodies produced by B-cells with other specificity are not bound to the membrane and go undetected. While we used ELISPOT detection, which is a highly quantitative and sensitive detection system, other detection systems well suited to detect antigen-specific antibodies after polyclonal stimulation of B-cells can also be used. These assays include ELISA, cytokine bead arrays, immune staining, immunoblotting, immune precipitation and immune agglutination.

Because it is known that B-cells produce antibodies in isolation only when they are acutely engaged in immune processes, we found that detection of such B-cells can help identify flares of MS. Distinguishing the two disease stages is important for making therapeutic decisions, we found that the Direct B-Cell assay can help identify active MS and the Indirect B-Cell assay can be effectively used to monitor MS patients not experiencing active disease or relapse.

Therapeutic significance of the Direct and Indirect B-Cell assays is the ability to guide therapeutic decisions for people with established MS. Because B-cells are also surfacing as possible mediators of the disease, the detection of such cells can help testing for the efficacy of therapies that aim to deplete B-cells for treatment of MS (e.g., using anti-CD20 and anti-CD22 antibodies). However, it may be generally considered that T-cells are causative in MS and B-cells have been considered only marginally important.

Initial trials of anti-CD20 antibodies have been demonstrated to be effective in MS patients, leading to a 91% reduction in new enhancing lesions and a 80% reduction in relapses compared to placebo treatment. Further, such antibodies are well tolerated by patients without major side effects.

In patients with CIS, only 4 of 12 responded to the Indirect B-Cell assay and one responded in the Direct B-Cell assay. However, when these findings are considered in light of two additional variables, 10 of 12 patients tested positive. Therefore, the combination of these four assays can be effective in diagnosing CIS. The four tests are: (1) Direct B-Cell assay, (2) Indirect B-Cell assay, (3) neuroantigen-induced (CNS-antigen induced) T-cell reactivity (via measurement of IFN-γ and IL-17), and (4) presence of serum antibodies to CNS antigen. The combination of these four assays therefore can be used to identify individuals at risk for developing MS at a stage of the disease where clinical diagnosis is still uncertain.

Furthermore, detection of CNS antigen-specific B-cells and T-cells can help to identify a subset of patients that benefit from immune modulatory treatment or T-cell or B-cell depletion therapy at any stage of the disease. Therefore, the assays of this invention are a useful companion for such treatments.

Our data show that myelin-reactive antibodies can play a significant role in the pathogenesis of EAE and due to the resemblance between EAE and the human disease it is to be assumed that this also applies to MS. It should be noted that disease occurred shortly after the injection of myelin-reactive serum delineating the role of antibodies for disease induction/outbreak. These data suggest that the correlation between the CNS antigen-specific T-cell response and the disease outcome also applies to the CNS antigen-/myelin-specific B-cell-/antibody response.

Our results indicate the importance of T-cells and B-cells and antibodies in the pathogenesis of the disease. We suggest that measurements of the CNS antigen-/myelin-specific T-cell responses and B-cell/antibody responses permit one to predict:

(a) whether a patient presenting with CIS or RIS will develop definite MS;
(b) whether and when a patient with definite MS will develop a disease relapse; and
(c) whether and how well a patient with CIS, RIS or MS will respond to treatment with immune modulators Statement (c) above implies that measurements of CNS antigen-/myelin-specific T-cell and B-cell/antibody responses also permit the identification of different patient subpopulations. Only if the pathogenesis has a predominant autoimmune component (meaning that T-cell and B-cell/antibodies contribute to the disease in a relevant way) immune modulatory treatment will be effective. If the pathogenesis in a patient is rather defined by e.g. primary oligodendrogliopathy immune modulatory treatment will not be as effective or even non-effective. Thus, the detection of CNS antigen-/myelin-specific T-cell responses and B-cell/antibody responses cannot only be regarded as diagnostic/prognostic test for MS, but also has important therapeutic implications.

While for the simple diagnosis of whether a patient will transit from CIS/RIS to MS it is sufficient to determine whether there is a myelin-specific T-cell/B-cell/autoantibody response, it can be useful to determine the magnitude of this response for defining whether and when the next relapse will occur and whether treatment will be effective and how effective it will be. The detection of a CNS antigen-/myelin-specific T-cell response or B-cell or antibody response and determining the magnitude of this response can be useful in evaluating treatment of MS.

Prior to this disclosure, there was discussion about whether treatment with immune modulatory drugs should be initiated as soon as an individual presents with CIS or RIS. Treatment can have severe side effects and it has also been reported that treatment responsiveness can decrease over time. In addition, patient compliance to treatment varies, considering the fact that it is unclear if a patient with CIS or RIS will actually develop MS. In some cases, CIS or RIS patients may not progress into definite MS. The diagnostic or prognostic methods we invented can help to avoid unnecessary treatment where possible and to initiate treatment where necessary. In addition, by predicting which patients with CIS/RIS will actually develop MS, our approach provides new methods to aid in preventive treatment options for MS. Thus far, there are only few studies exploring ways to prevent MS since prior to this disclosure, there have been no predictive tests available. Our methods can also contribute to the development of preventive treatment targeting the disease before significant CNS damage has occurred in the patient and thereby reducing the risk for the development of irreversible functional deficits in patients that can result from each additional relapse.

All patients that have MS or that will develop MS will have a detectable myelin-specific T-cell response and/or B-cell/autoantibody response. Modulations in the magnitude of this response can indicate whether a relapse is likely to occur, meaning that frequencies of cytokine/antibody producing T-cells/B-cells will increase prior to the relapse. This increase in the magnitude of the CNS antigen-specific T-cell response or B-cell antibody response can be therapeutically used. Here again, early therapy before the onset or recurrence of disease can prevent the development of irreversible CNS damage and thus irreversible functional deficits in patients. In addition, the correlation between the magnitude of the CNS antigen-specific response T-cell response or B-cell/antibody response and treatment effectiveness can help to optimize treatment options in individual patients, in particular avoiding treatment with drugs that are not successful in that patient, but can rather cause serious adverse effects.

The methods of this invention are rapid, cost effective, and do not require very expensive equipment, such as magnetic resonance imaging (MRI) devices. Tests of this invention can be carried out as an out-patient procedure, requiring only the acquisition of a sample of a patient's blood. These tests can be carried out at the point of care (e.g., physician's office), or can be carried out in a centralized location. The texts can be automated, and results obtained rapidly, thereby rapidly enabling appropriate diagnostic and therapeutic interventions. When combined with therapies disclosed herein, the diagnostic methods can be very powerful adjuncts to more traditional, and costly methods, such as MRI.

General Methods

Bead Array Based Assays

Use of Detection Surfaces in Detection Particle Bead Array Based Assay

Bead array technology is described in U.S. Pat. Nos. 7,598,093 and 8,088,630, both herein incorporated fully by reference. Briefly, a detection surface is in a cell culture plate (e.g., 96-well or 360-well microtiter plate) to detect cellular products. First, the detection surface can be the surface of a well in the plate or a membrane, which is coated with an antibody specific for the analyte of interest as a capture reagent. After several hours of incubation (2 hrs to overnight), during which the capture reagent(s) bind(s) to the membrane, excess capture reagent is washed away. The unsaturated surfaces of the membrane are then blocked with irrelevant protein (bovine serum albumin or gelatin) to prevent subsequent nonspecific binding of analytes. Following the blocking step, the plates are washed to remove non-plate bound, excess blocking reagent.

At this point the detection substrate is properly prepared to test cells. In some embodiments, human peripheral blood mononuclear lymphocytes (PBL or PBMCs) are added at a concentration of for example, about $5 \times 10^5$ per well. Specific antigen (e.g., hMOG) is added to the experimental wells, control wells contain no antigen or irrelevant antigen (e.g. myohemerythrin, a protein that humans have not encountered). Among all cells plated (about $5 \times 10^5$ cells) only the antigen specific T-cells will be stimulated by the antigen to release secretory products (e.g. IFN-gamma). In the control wells, in the absence of the antigen, antigen specific cells are not stimulated and do not release secretory products. During a 4-48 hr cell culture period (dependent on the product to be detected) the antigen specific cells secrete their products(s) being captured by the capture reagents around the secreting cell.

Following the culture period, the cells are washed away, leaving their secretory product retained on the membrane. In some embodiments, the cells can remain on the detection surface.

A detection reagent bound to a detection particle is added to bind to the plate-bound secretory product (the detection and capture antibodies specific for secretory products, e.g., IFN—have to recognize different parts of the molecule such as not to interfere with each other's binding). The detection particle is either directly labeled with a fluorochrome (e.g., FITC, PE or texas red) or has a characteristic spectral feature. (e.g., different spectral features for different cellular products). Directly labeled detection antibodies associated with detection particles are particularly useful. Alternatively, an antibody is added that is specific for the analyte and a secondary antibody is attached to the detection particle. Coupling of detection antibody to the detection particle by biotin-streptavidin can also be used.

There are a variety of means for visualizing the detection particles using a detection reagent such as: a) immune fluorescence if the secondary (or tertiary) reagent was a fluorochrome or b) a characteristic spectral feature (e.g., different "colors" for different analytes) visualized by light microscopy. Each "spot" of colored substrate corresponds to one cell producing or secreting the product. The difference in number of spots between antigen stimulated wells and the number of spots in the negative control wells (with medium alone or irrelevant antigen) establishes the "signal" to be analyzed (usually there is no spot formation in the negative control). Sizes of the spots correspond to the quantity of product secreted, the number of spots establishes the frequency of antigen specific cells in the cell population tested (i.e. cells that were induced by the antigen to secrete the product among all cells plated, e.g., 20 IFN-gamma spots in HIV antigen challenged PBL represent a frequency of 40/million, if $5\times10^5$ cells were plated).

To carry out peptide screening, microwells are employed to screen and identify the antigenic determinants that T-cells recognize, using peptides. Usually, in studies that involved peptides, a few randomly chosen sequences of the antigen are tested as peptides. However, even overlapping sequences that walk down the molecule in steps of 5 to 10 amino acids do not necessarily detect all determinants. By contrast, in this example overlapping sets of peptides are employed that walk the molecule amino acid by amino acid. This peptide scan includes every possible determinant on an antigen and provides an exact mapping of the T-cell repertoire. In some cases, a protein (hMOG, MBP, MP4 or other CNS antigen), or a peptide (e.g., hMOGp, MBPp and the like) can be used to screen for MS, CIS, RIS and related conditions.

While an assay system has been employed to test for antigen specific CD4 cells [G Gammon et al., "T Cell Determinant Structure: Cores and Determinant Envelopes in Three Mouse Major Histocompatibility Complex Haplotypes" J. Exp.Med. 173: 609-617 (1991)], the bead array methods allow for testing of CD8 cells. CD8 determinant mapping for HIV identifies possible peptides for vaccines. Determinant mapping for autoantigens in autoimmune disease has prognostic and possible therapeutic consequences.

For determinant mapping, Myelin Basic Protein ("MBP") peptides that walk the MBP molecule amino acids by amino acid are used. These peptides produce clear data in SHIV-ERER mice. The peptides can be frozen without losing bioactivity at 14 µM concentration in HL-1 medium, which is 2× the optimal concentration for the bioassay. Thus, the large number of peptides involved do not have to be diluted and plated for each experiment, but can be freshly thawed from storage. The entire peptide series is diluted, pipetted and frozen series in advance and, on the day of experiment, the required number of plates are prepared.

The number of cells available from patients can be limiting; one million cells can be obtained from one milliliter of blood and usually fifty milliliters of blood is available per patient (i.e., fifty million cells may be the total cells available for the assay). Because $2\times10^5$ cells per well provides clear results, this is sufficient for testing 250 peptides, which constitutes an average size protein. However, by miniaturizing the plates (e.g. to 50 microliter wells), one can test for 1000 peptides, which can cover even the larger proteins. The entire peptide series can be tested on an individual. The plating of the cells can be performed with 12 channel pipettors into the freshly prepared plates, reducing the time involvement on the first day of the assay to a couple of hours.

PBL cells (PBMCs) were plated at $2\times10^5$ cells per well into 96 well microtiter plates containing the hydrophobic membrane precoated with an antibody as capture reagent. The cells are incubated in the wells with antigen for 24 h at 37° C., 8% $CO_2$. During this culture period, T-cells with specificity for a given peptide are be activated and start secreting cytokines and other cellular products, which are captured by the appropriate antibody on the plate around producing cells. Thus, secreting cells (antigen specific memory cells) are surrounded by a "spot" of the cytokine. After an additional culture (24 hours), the cells can then be washed away and the bound cytokine is detected by a biotinylated second antibody that is specific for the same cytokine but recognizes a different determinant on it. The plate bound second antibody is attached to a microsphere with a characteristic marker thereon.

The numbers of spots in antigen containing wells vs. wells containing medium alone or irrelevant antigens establish the number of antigen specific cells in the culture. Since $2\times10^5$ cells are plated to each well, the absolute frequency represents the frequency of antigen reactive T-cells in $2\times10^5$ T-cells of the given specificity within the cell pool tested.

For a two color detection particle based assay, a capture surface is prepared as above, except that a second capture reagent and a second detection reagent/microsphere is used as well. To prepare the surface for a two-color assay, two (2) capture reagents (e.g., anti-IFN-γ and anti-IL-17 antibodies) are used simultaneously (for additional capabilities, still additional capture reagents can be employed for a "multicolor" assay).

Cells can be plated (about $5\times10^5$ cells) and only the antigen specific T-cells are stimulated by the antigen to release secretory products. In other embodiments, B-cell products (e.g., antibodies) can be detected. However, in the case of T-cells, the surface is capable of detecting both IFN-γ and IL-17. It can be appreciated that to detect antibodies secreted by B-cells, the surface of the plate can be coated with an antigen against which the B-cells produce antibodies. Thus, to use bead array assays to detect MS and related conditions, a plate can be coated with hMOG, hMBP, MP4 or a peptide thereof. When a B-cell is placed on the antigen, the cell can produce and secrete the anti-hMOG, anti-MBP, or anti-MP4 antibodies, which then can bind to the antigen and remain bound to the plate to enable detection using bead array methods.

After the culture period and washing described above, a second detection reagent attached to a second detection particle is employed together with the first detection reagent attached to a first detection particle. In this case, detection particles labeled with anti-IL-17 is added (alternatively, fluorochromes emitting different colors when excited by UV light permit two or multicolor assays e.g., FITC:green, PE:red). Spots originating from cells that secreted one of the products only, will appear as a single color (e.g., red or blue), while cells secreting both will have the both colors represented by different detection particles.

The detection particle based assay can be evaluated visually using a microscope or other optical device. Quantitative analysis (spots per $10^6$ splenocytes) for each cytokine reveals 180-250 spots per million cells. In order to verify that the assay is quantitatively reliable, a similar detection particle based analysis is performed on serially diluted samples, and we found that the number of responding cells falls linearly in relation to the serial dilution. Thus, the detection particle based assay yields reproducible quantitative and qualitative information regarding the alloimmune response. While it is not intended that the assays be limited by the use of particular antibodies, work with human PBLs has resulted in the determination that the antibody combinations set forth in Table 1 below can effectively detect human cytokines in recall responses to common antigens. It can be appreciated that the list in the Table is only exemplary. Many other capture reagents and detection reagents can be effectively used with bead based assays.

TABLE 1

Cytokines and Detection Reagents

| Cytokine | Coating Antibody (Capture Reagent) | Detection Antibody (Detection Reagent) |
|---|---|---|
| IL-2 | BG-5 (Serotec) | Rabbit polyclonal (BD) |
| IL-4 | 8D4-8 (PHRM) | MP4-25D2 (PHRM) |
| IL-5 | JES1-39D10 (PHRM) | JES1-5A10 (PHRM) |
| IL-10 | JES3-9D7 (PHRM) | JES3-12G8 (PHRM) |
| IFN | MA700 (ENDO) | MA701 (ENDO) |

In some instances, T-cells can be enriched from PBLs using human T-cell isolation columns (R and D Systems), as per manufacturer's recommendations. In other instances, depletion of T-cell subtypes is desired. Depletion of T-cell subtypes can be performed by standard methods, using OKT3 (anti-CD3), OKT4 (anti-CD4), or OKT8 (anti-CD8), and rabbit complement (Cedarlane, Hornsby Ont). Aliquots of the resultant cells can be washed and stained with FITC conjugated antibodies for phenotyping by FACS. The antibodies are isolated from hydridoma supernatants grown in our laboratory by standard methods.

In other embodiments, methods can be used to use particles directly labeled with detection secondary antibodies. It is analogous to the indirect method described here, with the difference that interaction of the streptavidin-labeled particles with biotinylated secondary antibodies takes place prior to their interaction with the cytokine-primary coating antibody complex on the surface. The method is based on the fact that interaction of streptavidin with its natural ligand, biotin, is practically irreversible; the equilibrium binding constant for this interaction exceeds the magnitude of $10^{11}$ $M^{-1}$.

Particles of each individual type (color) covalently conjugated with streptavidin or its analog, avidin, are premixed with the biotin-labeled secondary detection antibody (reagent) specific to each secreted product. After the reaction is completed, the excess of unbound biotinylated antibodies is removed by the addition of agarose beads coated with streptavidin. Agarose beads with the bound excessive biotinylated antibodies are then removed by centrifugation. Particles of different color, each labeled with single type of the secondary detection antibody (reagent) through streptavidin-biotin interaction, are incubated with the surface-bound secreted product similar to the way directly conjugated particles are used. Several particle types can be used either simultaneously or in a number of consecutive steps.

Specific Embodiments

Materials
B-Cell ELISPOT
1) MultiScreen$_{HTS}$™ Filter Plates for ELISPOT (Millipore, Billerica, Mass. Cat. No. MSIPS4W).
2) hMOG (Synthesized and kindly provided by Prof. Nancy H. Ruddle; Yale University, New Haven, Conn.).
3) Whole human brain lysate (Novus Biologicals, Littleton, Colo. Cat. No. NB820-59177)
4) MP4=MBP-PLP fusion protein (provided by Alexion Pharmaceuticals, Inc., Chesire, Conn.).
5) Recombinant human IL-2 for polyclonal stimulation: Synonyms: T-cell growth factor (TCGF), Aldesleukin. IL-2 is a powerful immunoregulatory lymphokine produced by T-cells in response to antigenic or mitogenic stimulation. IL-2/IL-2R signaling is required for T-cell proliferation and other fundamental functions which are essential for the immune response. IL-2 stimulates growth and differentiation of B-cells, NK cells, lymphokine activated killer cells, monocytes, macrophages and oligodendrocytes. (Peprotech, Rocky Hill, N.J.; Cat. No. 200-02).
6) R848 for polyclonal stimulation: R848 is an imidazoquinoline compound with potent anti-viral activity. This low molecular weight synthetic molecule activates immune cells via the TLR7/TLR8 MyD88-dependent signaling pathway. Recently, R848 was shown to trigger NF-κB activation in cells expressing murine TLR8 when combined with poly (dT) (Enzo Life Sciences, Farmingdale, N.Y.; Cat. No. ALX-420-038)
7) 2-mercaptoethanol for polyclonal stimulation: (Sigma-Aldrich, St. Louis, Mo.; Cat. No. M7154)
8) Detection antibodies for B-cell ELISPOT—Anti-Human IgG Fc PAN (1,2,3,4), biotin-conjugated (Hybridoma Reagent Laboratory, Baltimore, Md.; Cat. No. HP6043B)
9) Detection antibodies for B-cell ELISPOT—Anti-Human IgM, biotin-conjugated (Hybridoma Reagent Laboratory, Baltimore, Md. Cat. No. HP6083B).
10) Streptavidin-AP (Alkaline Phosphatase) (Sigma-Aldrich, St. Louis, Mo.; Cat. No. S2890).
11) Vector Blue Alkaline Phosphatase Substrate Kit; (Vector Laboratories, Burlingame, Calif.; Cat. No. SK-5300).
12) RPMI Media 1640 for cell culture with L-Glutamine: (Invitrogen, Grand Island, N.Y.; Cat. No. 11875).
13) Fetal bovine serum (FBS): (Invitrogen, Grand Island, N.Y.; Cat. No. 16140).

T-Cell ELISPOT
1) MultiScreen$_{HTS}$™ Filter Plates for ELISPOT: (Millipore, Billerica, Mass.; Cat. No. MSIPS4W).
2) Whole human brain lysate: (Novus Biologicals, Littleton, Colo.; Cat. No. NB820-59177).
3) MP4=MBP-PLP fusion protein: (Provided by Alexion Pharmaceuticals, Inc., Chesire, Conn.).
4) hMOG peptide library (synthesized by JPT Peptide Technologies GmbH, Berlin, Germany).
5) Anti-Human Interleukin-17A mAb MT44.6; purified (ELISPOT coating): (Mabtech, Nacka Strand, Sweden; Cat. No. 3520-3.
6) Anti-Human Interleukin-17A mAb MT504; biotinylated (ELISPOT detection): (Mabtech, Nacka Strand, Sweden; Cat. No. 3520-6.
7) Anti-Human Interferon-γ mAb 1-D1K; purified (ELISPOT coating) (Mabtech, Nacka Strand, Sweden; Cat. No. 3420-3).
8) Anti-Human Interferon-γ mAb 1-D1K; biotinylated (ELISPOT detection): (Mabtech, Nacka Strand, Sweden; Cat. No. 3420-6).
9) Streptavidin-AP (Alkaline Phosphatase): (Sigma-Aldrich, St. Louis, Mo.; Cat. No. S2890) 10) Vector Blue Alkaline Phosphatase Substrate Kit: (Vector Laboratories, Burlingame, Calif.; Cat. No. SK-5300.
11) RPMI Media 1640 for cell culture with L-Glutamine: (Invitrogen, Grand Island, N.Y.; Cat. No. 11875.
12) Fetal bovine serum (FBS): (Invitrogen, Grand Island, N.Y.; Cat. No. 16140).

Antibody ELISA
1) Immuno 96 MicroWell™ Solid Plates: (Thermo Scientific, Nunc, Rochester, N.Y.; Cat. No. 456537).
2) Whole human brain lysate: (Novus Biologicals, Littleton, Colo.; Cat. No. NB820-59177).
3) MP4=MBP-PLP fusion protein: (Provided by Alexion Pharmaceuticals, Inc., Chesire, Conn.).
4) Detection antibodies for B-cell ELISPOT—Anti-Human IgG Fc PAN (1,2,3,4), biotin-conjugated (Hybridoma Reagent Laboratory, Baltimore, Md.; Cat. No. HP6043B).

5) Fetal bovine serum (FBS): (Invitrogen, Grand Island, N.Y.; Cat. No. 16140).
6) Streptavidin-HRP (Horseradish Peroxidase): (BD Pharmingen, San Jose, Calif.; Cat. No. 557630).
7) TMB (3,3',5,5'-Tetramethylbenzidine) substrate: (eBioscience, San Diego, Calif.; Cat. No. 00-4201-56).

1. Direct B-Cell Test

Plasmablasts, also known as plasma cells or effector B-cells are characterized by the production of antibodies. If plasmablasts/plasma cells/effector B-cells are specific for CNS/myelin antigen they will produce antibodies against their specific CNS/myelin antigen, which can be directly measured in the blood. Measurement of such antibodies arising from the CNS can be detected using methods developed by Cellular Technology Ltd. (Neurospot™ is a trademark of Cellular Technology Ltd, Shaker Heights Ohio).

Approach

Filter or ELISA plates are coated with CNS/myelin antigen. PBMCs are isolated from the blood, e.g. by density gradient centrifugation and transferred to the plates as described in U.S. Pat. No. 7,598,093. After suitable incubation time, allowing sufficient secretion and binding of antibodies to the coated antigen, the production of CNS/myelin-specific antibodies is detected by either fluorescent or enzyme detection. Antibodies measured include IgM, IgD, IgG and IgG isotypes.

Therapeutic Significance for the Patient

B-cells will produce antibodies at isolation only when they are acutely engaged in immune processes (were recently activated). Therefore, detection of such B-cells will identify flares of MS (MS is known to progress in phases of clinical activity followed by periods of partial or complete remission). Clinically, this implies that patients with MS or at high risk to develop MS have to be monitored to detect the upcoming relapse before the patient has developed clinical symptoms. With each relapse there is a risk of remaining irreversible symptoms. Thus, the immune activity leading to the clinical relapse can desirably be attenuated before the patient develops clinically evident symptoms. The Direct B-Cell assay of this invention therefore can advantageously be used as an immune monitoring tool with direct therapeutic implications for the patient. A positive Direct B-Cell assay response indicates that treatment has to be initiated. Because immune activity needs to be suppressed at this stage, immunosuppressive treatment such as the administration of corticosteroids (which are commonly used for the treatment of acute disease in MS patients) or other immunosuppressive agents such as azathioprine, cyclophosphamide or mitoxantrone can be used when a positive B Cell assay response is observed.

2. Indirect Memory B-Cell Test

Memory B-cells may require several days of stimulation with polyclonal activators before they start secreting antibodies. We therefore developed an in vitro "Indirect B-Cell test" to identify such cells from the blood. Polyclonal stimulation can be done in a pre-incubation step, in which B-cells are stimulated with polyclonal activators for 3-8 days in culture. Polyclonal stimulation may include pre-incubation with IL-2, R-848 and β-mercaptoethanol and other protocols that are commonly used to polyclonally stimulate B-cells. Consecutively, the production of CNS antigen-/myelin-specific antibodies by polyclonally activated B cells can be performed as described in Section 1 above for Direct B Cell assays.

Approach

Peripheral blood mononuclear cells (PBMCs) are isolated from the blood, e.g. by density gradient centrifugation. The B cells contained in the sample are polyclonally stimulated e.g. with IL-2, R-848 and β-mercaptoethanol and subsequently transferred to filter plates or ELISA plates that have been coated with CNS antigen (that is whole brain lysate, MBP/PLP or human MOG). The polyclonally stimulated cells are then incubated on the plate. After suitable incubation time, allowing sufficient binding of secreted antibodies to the antigen on the plate, the production of CNS/myelin-specific antibodies is detected by either fluorescent or colorimetric enzyme detection. Antibodies measured include IgM, IgD, IgG and IgG isotypes.

Therapeutic Significance for the Patient

Therapeutic significance of the indirect memory B-cell test is the ability to guide therapeutic decisions for people with established MS.

1) The Indirect Memory B-Cell test can be used for verifying the diagnosis of definite MS. Our data show that 100% of definite MS patients tested positive in using the Indirect Memory B-Cell Test. The current diagnostic tool for diagnosing MS is mainly MRI. However, as a systematic literature review revealed "Magnetic resonance imaging (MRI) is not particularly useful in ruling in or ruling out multiple sclerosis (MS). Relying on it will result in overdiagnosis; using it to rule out MS will cause you to miss about half of those eventually clinically diagnosed." (Whitting et al., 2006). With a sensitivity and specificity of 100%, the Indirect Memory B-Cell Test of this invention is a reliable tool for the diagnosis of MS, while being more cost-effective and easy to perform at the same time since only a blood sample is needed.

2) In our studies, the Indirect Memory B-Cell test shows that B-cells are importantly involved in the pathogenesis of MS. This finding has direct therapeutic consequences for the treatment of MS patients. Currently, treatment relies on immune modulatory strategies that do not specifically target individual immune cell populations, but rather show a more general mode of activation. These drugs comprise glatirameracetate, interferon-beta, natalizumab and fingolimod. The therapeutic strength of anti-B-cell treatment via B-cell depleting agents such as anti-CD20 or anti-CD22 antibodies (e.g. rituximab, ocrelizumab, ofatumumab) or via agents targeting the survival of B-cells such as atacicept and belimumab has been shown in initial trials leading to a 91% reduction in new enhancing lesions and a 50% reduction in relapses compared to placebo treatment. However, so far, none of these highly potent drugs has been approved for the treatment of MS, partly due to the fact that there is currently no highly sensitive and specific monitoring tool available allowing the reliable diagnosis of whether a patient has B-cell-dependent MS. The Indirect Memory B-Cell test of this invention will allow a practitioner to determine whether a patient has B-cell-dependent MS. Following a positive Indirect Memory B-Cell test in these patients, B-cell therapy is to be initiated, and is highly likely to be very effective. Therefore, a positive Indirect Memory B-Cell test response has direct therapeutic consequences for the individual patient and will justify B-cell-specific therapy.

3) The magnitude of the positive test response in the Indirect Memory B-Cell test is related to the magnitude of the autoimmune B-cell response in individual patients. Thus, once either B-cell-specific or immune modulatory treatment has been initiated the treatment success can be monitored via the Indirect Memory B-Cell test. Treatment success is likely to be related to a diminution of the magnitude of the positive response in the Indirect Memory B-Cell test (i.e., a decrease in spot number, spot size or spot intensity).

3. Detection of CNS Antigen-Specific Antibodies in the Serum or Plasma

Despite detecting CNS antigen-specific lymphocytes in the blood, antibodies that have already been secreted by these cells in vivo can be detected in the serum/plasma.

Approach

ELISA plates are coated with CNS/myelin antigen. A sample of serum or plasma is collected and applied to the coated plates. After suitable incubation time allowing for sufficient binding of antibodies to the coated antigen, the presence of CNS/myelin-specific antibodies is detected by enzyme detection. Antibodies measured include IgM, IgD, IgG and IgG isotypes.

4. Combined Detection of B-Cells and T-Cells

In other embodiments, this invention includes methods to combine measurements of CNS antigen-/myelin-specific B-cells and the production of CNS antigen-/myelin-specific antibodies by these B-cells with the detection of, IFN-γ and IL-17 production by CNS antigen-/myelin-specific T-cells in the blood. Both CNS antigen-/myelin-specific B-cells/antibodies and T-cells can contribute to the pathogenesis of MS. While in one subset of patients CNS antigen-/myelin-reactive B-cells/antibodies may be the main pathogenic correlate, CNS antigen-/myelin-reactive T-cells can be the main pathogenic correlate in another subset of patients. Also, there is a subset of patients, in which both CNS antigen-/myelin-specific B-cells/antibodies and T-cells equally contribute to the pathogenesis. As mentioned above, there can also be a subset of patients, in which both CNS antigen-/myelin-reactive B-cells/antibodies and T-cells are not crucially involved. The combined measurement of CNS antigen-/myelin-specific B-cells/antibodies and T-cells is necessary to cover the full pathogenic spectrum evident in patients, thus increasing diagnostic/predictive efficiency and precision of the assay and also permitting the distinction between different patient subpopulations.

5. Detection of B-Lymphocyte or T-Lymphocyte Products

In certain embodiments of this invention, detection of B-lymphocyte or T-lymphocyte products can be carried out using one of a variety of methods. Such methods include fluorometric spot assays ("Fluorospot™" Cellular Technology Ltd. Shaker Heights, Ohio), enzyme-linked spot (ELISPOT) assays, enzyme-linked immunosorbent assays (ELISA), immunoblotting (e.g., dot blot technique), polymerase chain reaction (PCR), and real-time PCR (RT-PCR), Radioimmunoassays (RIA), cytokine bead arrays, protein arrays, bead aggregation assays, intracellular cytokine staining, immunoprecipitation assays, immunohistochemistry, in situ cytokine detection on slides, cell screening or ultrasensitive densitometry by nanoparticle-modified aptamers.

ELISPOT Assays

According to embodiments of this invention, enzyme linked immune spot ("ELISPOT") assays can be carried out using methods described in U.S. Pat. Nos. 7,598,093 and 8,088,630, (incorporated herein fully by reference. Analyzers and methods from Celleular Technology Ltd (Immunospot® is a Registered Trademark of Cellular Technology Ltd. ("CTL"), Shaker Heights, Ohio). Analyzers and methods can be obtained from CTL.

CNS antigen-specific antibodies can be detected and measured in serum using ELISA, cytokine bead arrays, protein arrays and test strips. Antibodies detected can include IgA, IgD, IgE, IgG and IgM and their isotypes. Detection of B-lymphocytes in the blood includes measuring spontaneous production of antibodies by white blood cells after their isolation from the blood. B-lymphocyte ELISPOT assays, ELISA, cytokine bead arrays and protein array assays can be used. B-lymphocyte stimulation can be carried out by exposing B-cells to CNS antigens or by polyclonal stimulation by IL-2, R-848 and β-mercaptoethanol or other method commonly used to stimulate polyclonal production of B-lymphocytes.

T-lymphocyte measurements also include antigen-induced cellular proliferation, as assayed, for example, by thymidine incorporation assays. Assays using MTT or similar compounds can also be used. MTT (3-(4,5-Dimethyl-2-yl)-2,5-diphenyltetrazolium bromide, a yellow tetrazole), is reduced to purple formazan in living cells. A solubilization solution (usually either dimethyl sulfoxide, an acidified ethanol solution, or a solution of the sodium dodecyl sulfate is added to dissolve the insoluble purple formazan product into a colored solution the absorbance of this colored solution can be quantified by measuring at a certain wavelength. The absorption maximum is dependent on the solvent employed.

XTT (2,3-bis-(2-methoxy-4-nitro-5-sulfophenyl)-2H-tetrazolium-5-carboxanilide) can also be used. The formed formazan dyes is water soluble, avoiding a final solubilization step.

Water soluble tetrazolium salts were developed by introducing positive or negative charges and hydroxyl groups to the phenyl ring of the tetrazolium salt, or better with sulfonate groups added directly or indirectly to the phenyl ring.

MTS (3-(4,5-dimethylthiazol-2-yl)-5-(3-carboxymethoxyphenyl)-2-(4-sulfophenyl)-2H-tetrazolium), in the presence of phenazine methosulfate (PMS), produces a formazan product that has an absorbance maximum at 490-500 nm in phosphate-buffered saline.

WSTs (Water Soluble Tetrazolium salts) are a series of other water soluble dyes for MTT Assays, developed to give different absorption spectra of the formed formazans. WST-1 and in particular WST-8 (2-(2-methoxy-4-nitrophenyl)-3-(4-nitrophenyl)-5-(2,4-disulfophenyl)-2H-tetrazolium), are advantageous over MTT in that they are reduced outside cells, combined with PMS electron mediator, and yield a water-soluble formazan. Finally, WST assays (1) can be read directly (unlike MTT that needs a solubilization step), (2) give a more effective signal than MTT, and (3) decrease toxicity to cells (unlike cell-permeable MTT, and its insoluble formazan that accumulate inside cells).

Additionally, T-lymphocyte response can be assayed by measuring adenosine tri-phosphate (ATP) production and CFSE methods.

Therapeutic Significance for the Patient

Clinical significance of combining the above described B-cell or T-cell approaches with the detection of CNS antigen-reactive $T_H1/T_H17$ responses and serum or plasma measurements of CNS antigen-specific antibodies resides in the effectiveness to solidify the diagnosis of MS in patients with clinically-isolated syndrome or radiologically-isolated syndrome (CIS/RIS). As mentioned above, basing the diagnosis of MS solely on MRI is not reliable. As shown by our data, 10 of 12 patients who were suspected to have MS tested positive in the combined approach. For all of these patients, the diagnosis of MS has subsequently been confirmed due to the emergence of a new clinical relapse and the occurrence of additional CNS lesions. For the two patients that had negative test results the diagnosis of MS was not confirmed. Thus, a combined test approach of this invention is a highly sensitive and specific test for diagnosing MS at an early stage. This has broad therapeutic implications for the patients since a positive test response determines the need for initiating immune modulatory therapy. At the current stage, it is unclear whether patients with CIS/RIS should be treated for MS and a significant amount of patients refuses therapy at this stage, since immune modulatory treatment has adverse side effects. However, it has been shown that in case a patient has definite MS, early treatment is important to prevent long-term CNS atrophy and functional deficits. In many patients, treatment is only initiated once a second relapse has occurred, always bearing the risk to lead to irreversible symptoms. Thus, a positive result in our combined test will directly indicate a therapeutic decision to initiate immune modulatory treatment.

In addition, our data show that with disease progression to the secondary-progressive stage of MS, patients increasingly become negative in the combined B-cell T-cell-antibody test. This result is indicative of a transition from a primary autoimmune pathogenesis of MS to primary neurodegeneration that occurs in the CNS itself. Once a state of prevailing neurodegeneration has been reached, immune modulatory treatment is likely to become ineffective. On the one hand, our combined test allows one to monitor disease activity in individual patients. The transition from a positive to a negative test result will indicate that cessation of treatment is prudent because therapy is unlikely to be effective. Should there be the option for neuroregenerative treatment in the future (so far, such drugs are not available) negative test results will indicate that such options are likely to be more effective than immune modulatory treatment. However, our data also show that 5/12 patients with secondary progressive MS retained a positive Indirect Memory B-Cell test response. These patients are likely to still benefit from immune modulatory treatment, in particular anti-B-cell therapy and can be identified by our test.

EXAMPLES

This invention is further illustrated by the following examples, which are not considered limiting to the scope of this invention. Rather, they are used to point out certain embodiments. Persons of skill in the art can use the descriptions and teachings herein to produce other embodiments that are within the scope of this invention. All such embodiments are considered to be part of this invention.

Example 1: Detection of Myelin-Specific B-Cells and Antibodies from Human Patients with Multiple Sclerosis I Methods:

Filter plates were coated with MBP/PLP antigen. PBMC were isolated from the blood by density gradient centrifugation and transferred to the plates as described in U.S. Pat. No. 7,598,093. After a suitable incubation time, allowing sufficient secretion and binding of antibodies to the coated antigen, the production of CNS/myelin-specific antibodies was detected by enzyme-linked immunoassay detection. Antibodies measured included IgM and IgG.

Figure 1A:
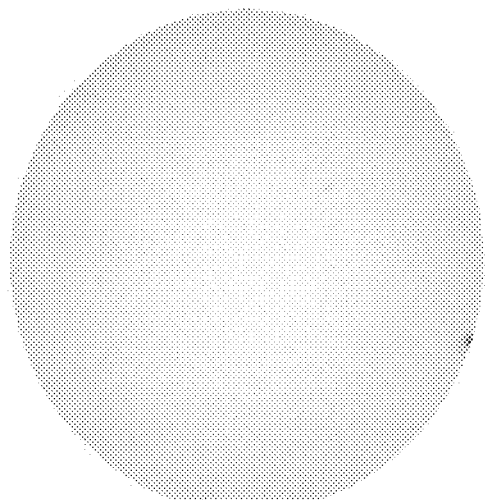
FIGS. 1A-1D depict photographic detection of myelin (MP4)-specific antibodies in MS patients (FIGS. 1A and 1B).
Figure 1B:
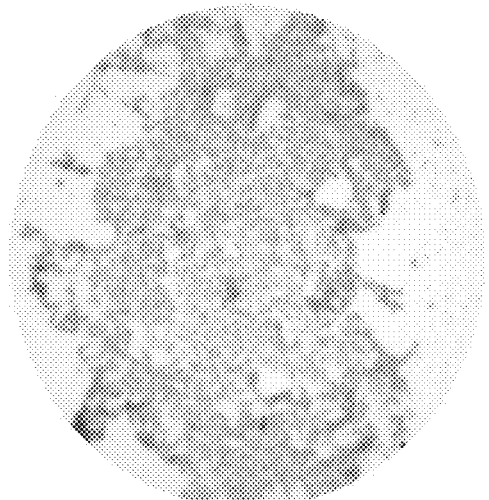
Figure 1C:
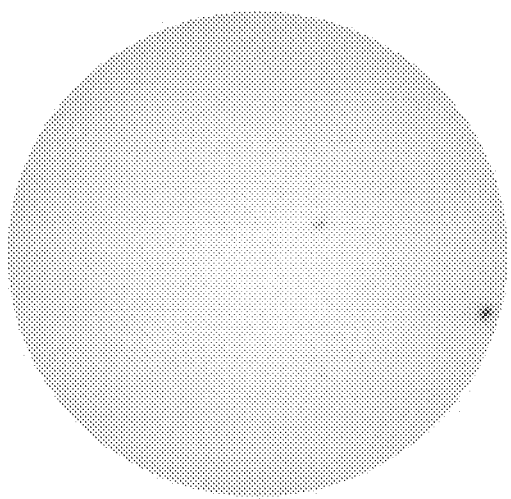
Figure 1D:
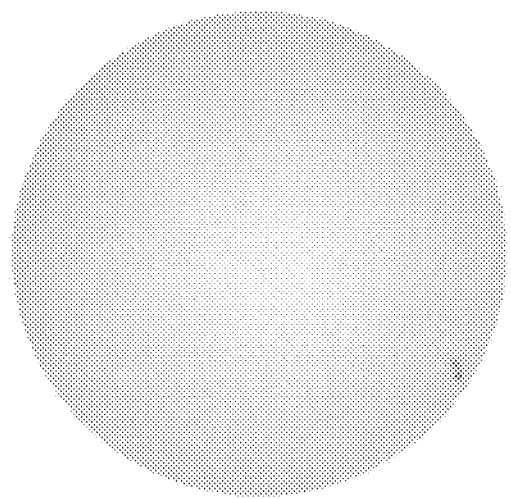

Results:

FIG. 1 depicts detection of MBP/PLP-specific antibodies in the blood of an MS patient with acute relapse of disease activity/(FIG. 1B). CNS antigen-specific antibody secreting B-cells were present in the blood of this patient and the antibody secretion by B-cells could be readily detected by B-cell ELISPOT (using a Direct B-Cell assay of this invention). This reaction was antigen-specific and did not occur in the absence of antigen (medium control; FIG. 1A) or in healthy controls (FIGS. 1C and 1D).

Example 2: Detection of Myelin-Specific Immune Cells from a Human Patient with Multiple Sclerosis II Peripheral blood mononuclear cells (PBMCs) were isolated from the blood by density gradient centrifugation. The B-cells contained in the sample were polyclonally stimulated with IL-2, R-848 and β-mercaptoethanol for 3 days and subsequently transferred to filter plates that have been coated with CNS antigen (that is whole brain lysate or human MOG). The polyclonally stimulated cells were then incubated on the plate for 24 h. The production of CNS/myelin-specific antibodies and binding to the antigen on the plate was detected by colorimetric enzyme detection. Antibodies measured included IgG.

FIG. 2 depicts detection of interferon-gamma (IFN-γ) from immune cells in the blood of an MS patient after polyclonal stimulation in response to whole human brain lysate-specific antibodies and hMOG-specific antibodies. (FIG. 2B; upper right photograph). The response was antigen-specific and did not occur in the absence of antigen (medium control; FIG. 2A; upper left photograph) or in healthy controls (FIG. 2C; lower left photograph and 2D; lower right photograph).

Figure 2A:
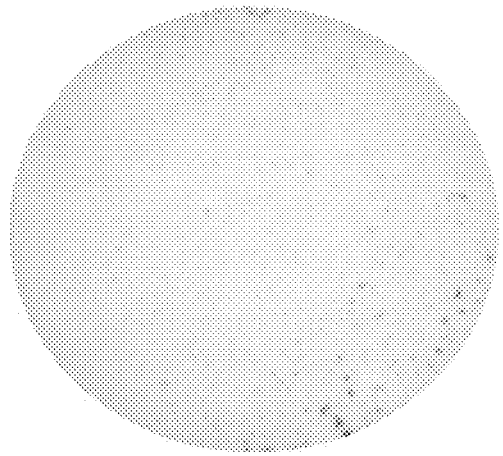
FIGS. 2A-2H depict detection of myelin (MP4)-specific IFN-γ secretion from immune cells in MS patients. Incubation of PBMCs isolated from the blood with control medium (FIGS. 2A and 2C) shows no IFN-γ immunoreactivity. In contrast, FIGS. 2B and D shows that CNS antigen triggers IFN-γ production in MS patients (FIG. 2B), but not in healthy controls (FIG. 2D). This reaction is antigen-specific and does not occur in the absence of antigen (medium controls).
Figure 2B:
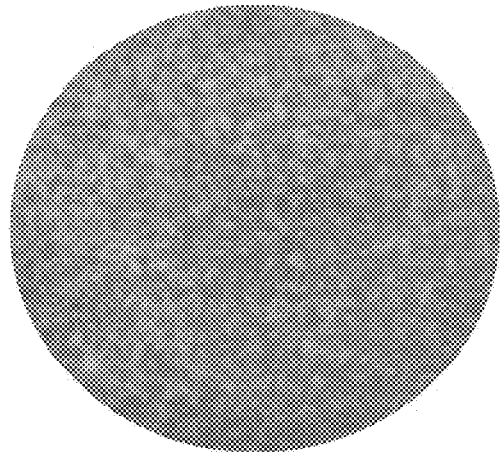
Figure 2C:
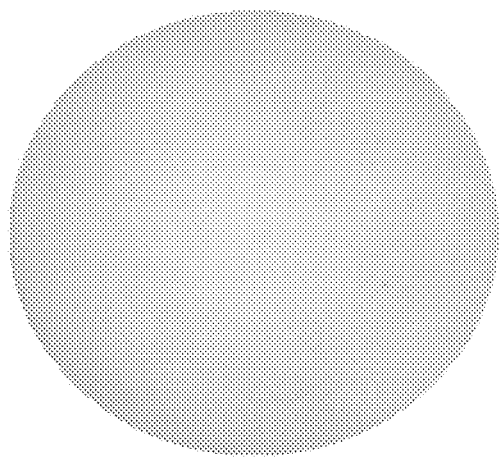
Figure 2D:
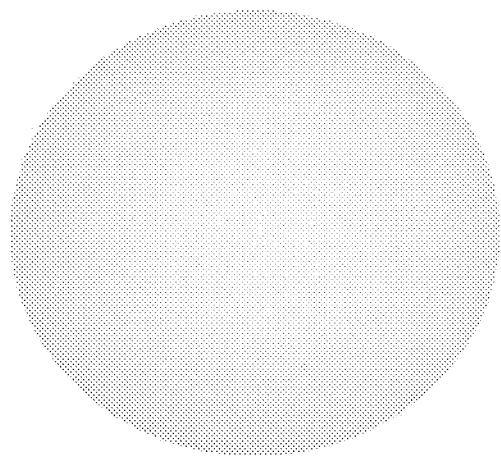
Figure 2E:
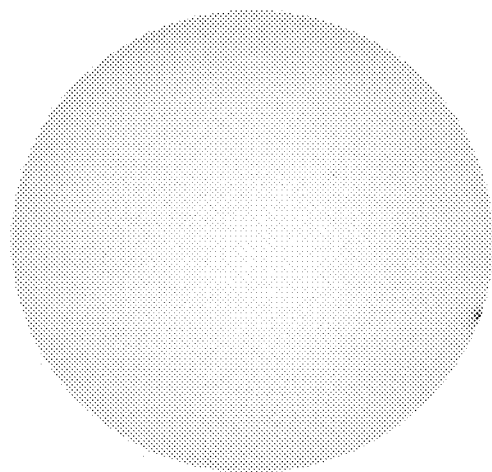
Figure 2F:
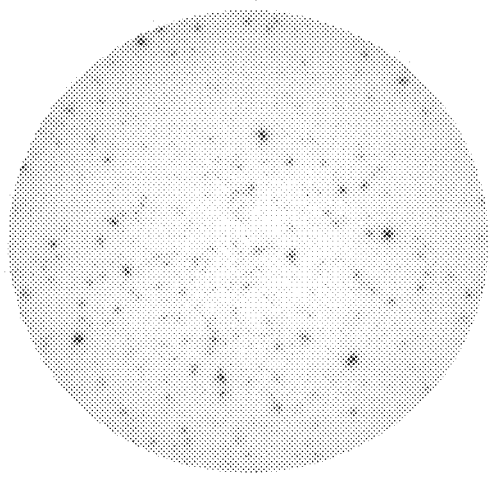
Figure 2G:
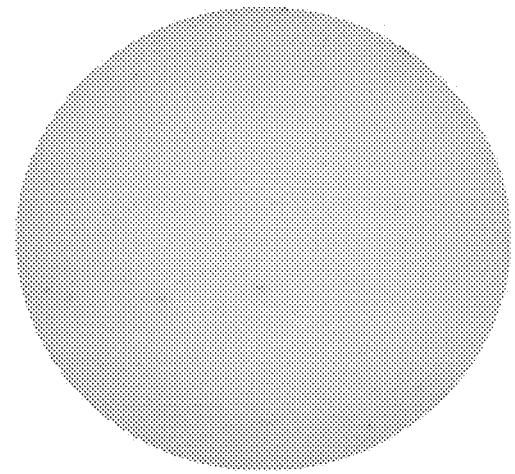
Figure 2H:
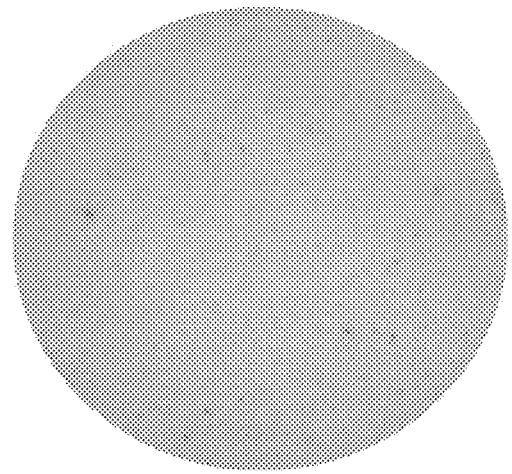

FIGS. 2E-2H depict photographs of cell culture wells containing PBMCs from a patient with MS (FIG. 2F, upper photographs) in the presence of a medium control (FIG. 2E; upper left photograph) or MP4 (upper right photograph). The spots in the photograph represent detection of interleukin 17 (IL-17) released from the immune cells. In contrast, PBMCs from a healthy control subject showed few, if any stained cells, either in the presence of a medium control (FIG. 2G; lower left photograph) or MP4 (FIG. 2H; lower right photograph).

Example 3: CNS Antigen-Specific IFN-γ and IL-17 Responses Detected in the Blood of Immunized Mice To determine whether CNS antigen-specific IFN-γ and IL-17 responses could be detected in the blood of mice, n=16 SJL mice were immunized with 100 μg PLPp in CFA, and n=14 B6 mice with 100 μg MOGp in CFA. In addition, n=8 SJL and n=8 B6 mice received PBS in the absence of antigen in CFA. PTx was given on the day of immunization and 48 h later. On day 10 after immunization, mice were bled and PBMCs were isolated as described above and tested for their respective CNS antigen-specific IFN-γ and IL-17 response in double-color ELISPOT assays.

FIG. 3A depicts the detection of myelin (MBP/PLP)-specific IFN-γ and IL-17 secretion from T-cells from mice treated with EAE. PBS/CFA immunization did not trigger PLPp- or MOGp-specific IFN-γ and IL-17 responses in SJL or B6 mice, respectively. Incubation of PBMCs isolated from the blood with MBP/PLP triggered IFN-γ (open circles) and IL-17 (filled circles) production by CNS antigen-specific T-cells in mice with EAE (PLPp/CFA and MOGp/CFA), but not in healthy controls (PBS/CFA). Although the difference between IFN-γ and IL-17 producing cells was statistically significant in the PLPp model ($p<0.001$), spot numbers were similar in MOGp-induced EAE ($p=0.564$). The reactions were antigen-specific and did not occur in the absence of antigen (medium control (PBS/CFA).

Figure 3B:
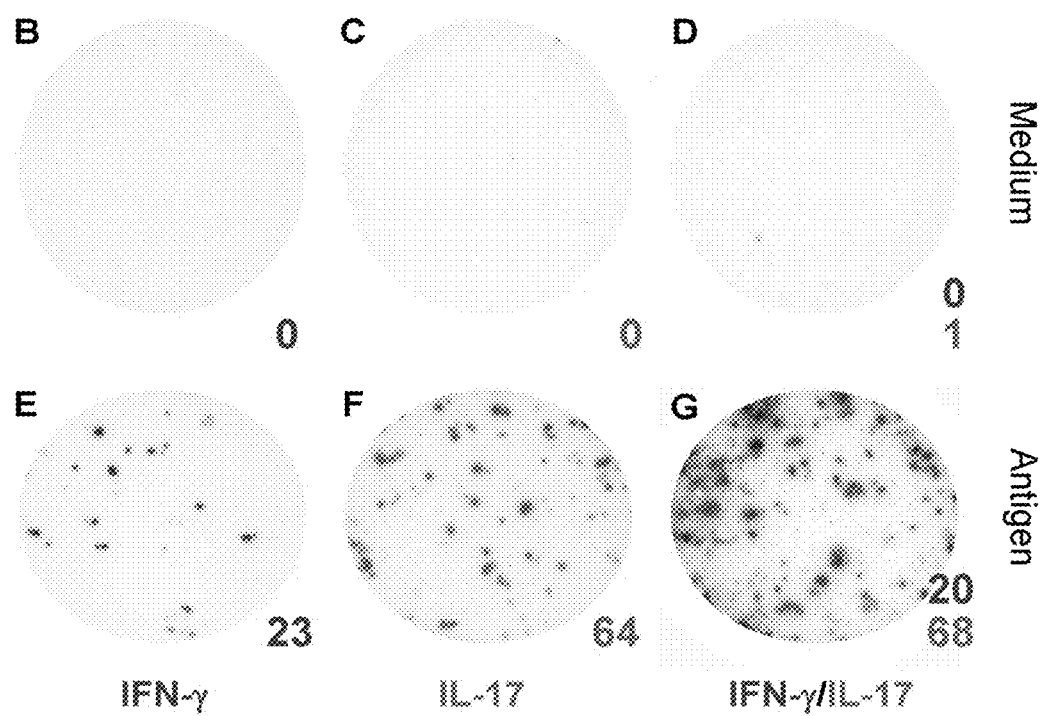

FIGS. 3B-3D depict photographs of cell culture wells in which medium was incubated without any antigen. FIGS. 3B, 3C and 3D show no spots, indicating lack of presence of any cellular responses. In contrast, FIGS. 3E, 3F and 3G each show spots indicating presence of cellular responses. FIG. 3E shows that cells released IFN-γ, (23 spots). FIG. 3F shows release of IL-17 (64 spots), and FIG. 3G shows both IFN-γ (68 spots) and IL-17 (20 spots) together. Spot counts in the medium control wells were typically low (<3 spots/$10^6$ cells) (FIGS. 3B-3D) and CNS antigen-specific responses could clearly be detected over this background (FIGS. 3E-3G).

We conclude from this study that assays of this invention provide the ability for the first time, to detect T-cell responses reflective of their ability to produce cytokines in response to stimulation by CNS antigens. We further conclude that assays of this invention can be useful to detect T-cell responses in disorders involving CNS antigen sensitivity in human beings. In particular, we conclude that assays of this invention can be useful in detecting MS in human beings, and can be useful in monitoring state of relapse, recurrence, and responses to therapy for MS.

Example 4: Double-Color Assay

To validate use of a double-color assay for INF-γ and IL-17 as described above in Example 3, we compared results of assays carried out using either a single color assay for INF-γ or IL-17, and compared the results with those obtained using a double-color assay for both cytokines.

Figure 4:
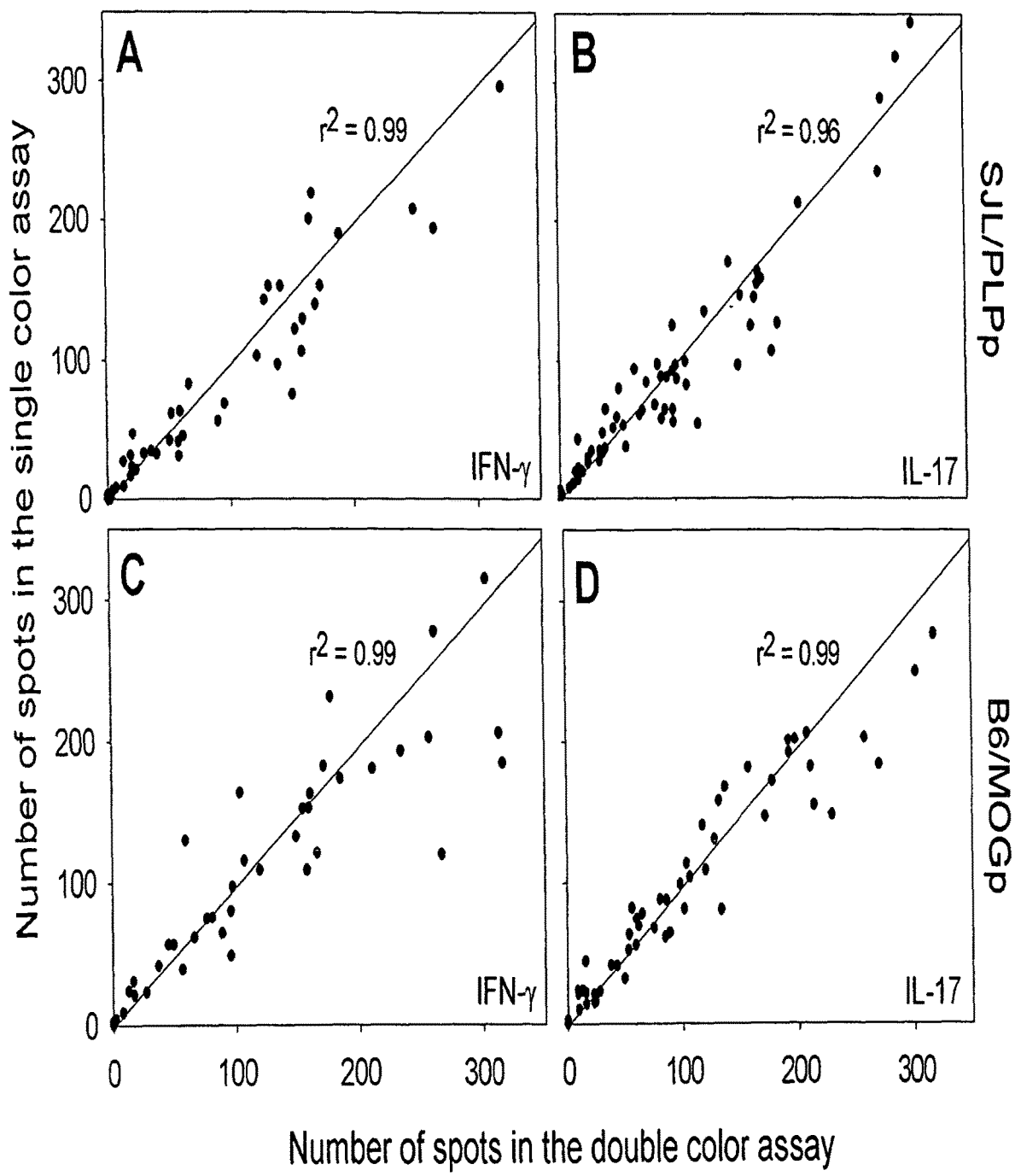
FIGS. 4A-4D depict graphs comparing a double-color IFN-γ/IL-17 ELISPOT assay and a corresponding single-color assay. SJL and B6 mice were immunized with the corresponding CNS antigen. On days 10, 20, 30 and 40 (SJL mice.

FIGS. 4A-4D depict graphs comparing a double-color IFN-γ/IL-17 ELISPOT assay and a corresponding single-color assay. SJL and B6 mice were immunized with the corresponding CNS antigen. On days 10, 20, 30 and 40 (SJL mice; FIGS. 4A and 4B) or 10, 25 and 40 (B6 mice; FIGS. 4C and 4D) after immunization, PBMCs were obtained from blood, spleen and drLNs, then tested for their antigen-specific IFN-γ (FIGS. 4A and 4C) and IL-17 (FIGS. 4B and 4D) production in single- and double-color ELISPOT assays. The number of spots obtained in the single-color assay was highly correlated to the results in the double-color assay for each cell sample. The correlation coefficients ($r^2$) were all above 0.96. A total of n=30 SJL mice and n=17 B6 mice were tested in four and three independent experiments, respectively. All results are medium-subtracted and normalized to $10^6$ cells.

Example 5: EAE and CNS Antigen-Specific T-Cells in Mice Correlate with Disease Severity Due to the limited numbers of PBMCs that can be obtained from the blood of individual mice, a key question whether central disease parameters such as onset, progression and severity correlate with the magnitude and cytokine quality of the T-cell response in experimental autoimmune encephalomyelitis (EAE) has remained unanswered.

In embodiments of this invention, we developed an ELISPOT-based PBMC test system in which as little as 150 μl of murine blood are sufficient, allowing to bleed mice repeatedly while continuing to observe the clinical course of EAE. Using this technique, we demonstrate that longitudinal measurements of antigen-specific IFN-γ and IL-17 production in the blood are a highly suitable approach to predict the disease outcome in remitting-relapsing PLP:139-151- and chronic MOG:35-55-induced EAE of SJL/J and C57BL/6 mice, respectively. We demonstrated low volume cytokine monitoring as useful in for efficient diagnostic and prognostic options in human multiple sclerosis and other autoimmune diseases.

Experimental autoimmune encephalomyelitis (EAE) is a common model for multiple sclerosis (J. Goverman and T. Brab, Lab. Anim Sci. 46 (1996) 482-492; M. Sospedra and R. Martin, Annu. Rev. Immunol. 23 (2005) 683-747; L. Steinman and S. S Zamvil, Ann. Neurol. 60 (2006) 12-21; R. Gold et al., Brain 129 (2006) 1953-1971). EAE is induced by immunization with CNS antigens that trigger an autoimmune T cell response. For example, the proteolipid protein (PLP) peptide 139-151-induced EAE in SJL mice (V. K. Tuohy et al., J. Immunol. 142 (1989) 1523-1527; R. A. Sobel et al., J. Neuropathol. Exp. Neurol. 49 (1990) 468-479) and the myelin oligodendrocyte glycoprotein (MOG) peptide 35-55-triggered disease in C57BL/6 (B6) mice (I. Mendel et al., Eur. J. Immunol. 25 (1995) 1951-1959; I. Mendel et al., Eur. J. Immunol. 26 (1996) 2470-2479) have evolved as prevalent murine models. Whereas the former is characterized by a predictable relapsing-remitting course, the disease is chronic in the latter. In both models, the respective CNS antigen-specific $CD4^+$ T cells are known to cause the immunopathology in the absence of antibodies playing a significant role (N. T. Potter and T. S. Stephens, J. Neurosci. Res. 37 (1994) 15-22; B. L. McRae and S. D. Miller, Neurochem. Res. 19 (1994) 997-1004;] P. Hjelmstrom et al., J. Immunol.161 (1998) 4480-4483; A. R. Oliver et al., J. Immunol. 171 (2003) 462-468).

Sequences of immunogens are shown below in single letter code.

```
1) Human Myelin Oligodendrocyte Glyoprotein (hMOG)
                                                          SEQ ID NO. 1
   MASLSRPSLP SCLCSFLLLL LLQVS SSYAG QFRVIGPRHP IRALV GDEVE LPCRISPGKN        60

ATGMEVGWYR PPFSRVVHLY RNGKDQDGDQ APEYRGRTEL LKDAIGEGKV TLRIRNVRFS         120

DEGGFTCFFR DHSYQEEAAM ELKVEDPFYW VSPGVLVLLA VLPVLLLQIT VGLVFLCLQY         180

RLRGKLRAEI ENLHRTFDPH FLRVPCWKIT LFVIVPVLGP LVALIICYNW LHRRLAGQFL         240

EELRNPF                                                                  247

2) Human MOG 35-55
                                                          SEQ ID NO. 2
   SSYAGQFRVI GPRHPIRALV                                                    20

3) Human Myelin Basic Protein (MBP), Isoform 3, 21.5 kDa
                                                          SEQ ID NO. 3
   MASQKRPSQR HGSKYLATAS TMDHARHGFL PRHRDTGILD SIGRFFGGDR GAPKRGSGKV         60

PWLKPGRSPL PSHARSQPGL CNMYKDSHHP ARTAHYGSLP QKSHGRTQDE NPVVHFFKNI         120
```

```
                                                          -continued
VTPRTPPPSQ GKGRGLSLSR FSWGAEGQRP GFGYGGRASD YKSAHKGFKG VDAQGTLSKI            180

FKLGGRDSRS GSPMARR                                                           197

4) Human Proteolipid Protein (ΔPLP4)
                                                                       SEQ ID NO. 4
MGLLECCARC LVGAPFASLV ATGLCFFGVA LFCGCGHEAL TGTEKLIETY FSKNYQDYEY             60

LINVIHAFQY VIYGTASFFF LYGALLLAEG FYTTGAVEQI FGDYKTTICG KGLSATVTGG            120

QKGRGSRGQH QAHSLERVC H CLGKWLGHPD KF VGITYALT VVWLLVFACS AVPVYITFNT          180

PWNAFPGKVC GSNLLSICKT AEFQMTFHLF IAAFVGAAAT LVSLLTFMIA ATYNFAVLKL            220

MGRGTKF                                                                      227

5) PLP peptide 139-151 (PLPp)
                                                                       SEQ ID NO. 5
HCLGKWLGHP DKF                                                                13

6) The Linker for MBP and ΔPLP4 (MP4)
                                                                       SEQ ID NO. 6
LLGGLEDP                                                                       8

7) MP4
                                                                       SEQ ID NO. 7
MASQKRPSQR HGSKYLATAS TMDHARHGFL PRHRDTGILD SIGRFFGGDR GAPKRGSGKV             60

PWLKPGRSPL PSHARSQPGL CNMYKDSHHP ARTAHYGSLP QKSHGRTQDE NPVVHFFKNI            120

VTPRTPPPSQ GKGRGLSLSR FSWGAEGQRP GFGYGGRASD YKSAHKGFKG VDAQGTLSKI            180

FKLGGRDSRS GSPMARR        LLGGLEDP    MGLLECCARC LVGAPFASLV ATGLCFFGVA       235

LFCGCGHEAL TGTEKLIETY FSKNYQDYEY LINVIHAFQY VIYGTASFFF LYGALLLAEG            295

FYTTGAVEQI FGDYKTTICG KGLSATVTGG QKGRGSRGQH QAHSLERVCH CLGKWLGHPD            355

KFVGITYALT VVWLLVFACS AVPVYITFNT PWNAFPGKVC GSNLLSICKT AEFQMTFHLF            415

IAAFVGAAAT LVSLLTFMIA ATYNFAVLKL MGRGTKF                                    452
```

CD4+ T-cells can mediate the immune pathology by secreting cytokines that activate and attract cells of the innate immune system, primarily macrophages, into delayed-type hypersensitivity (DTH)-like reaction. For many years, the mediation of DTH in the CNS was attributed to IFN-γ secreting "$T_H1$ type" cells and subsequently, most efforts of immune monitoring focused on measuring IFN-γ to identify the autoreactive effector cells (J. E. Merrill et al., Proc. Natl. Acad. Sci. USA 89 (1992) 574-578; V. Navikas and H. Link, J. Neurosci. Res. 45 (1996) 322-333; H. H. Hofstetter et al., J. Neuroimmunol. 170 (2005) 105-114; H. H. Hofstetter and T. G. Forsthuber, Neurosci. Lett. 476 (2010) 150-15). More recently though, the pathogenic/encephalitogenic quality of autoreactive cells was linked to the ability to produce IL-17, accounting for a $T_H$ lineage independent of the IFN-γ producing $T_H1$ cell and termed $T_H17$ (H. H. Hofstetter et al., Cell. Immunol. 237 (2005) 123-130; I. I. Ivanov et al., Cell 126 (2006) 1121-33; Y. Komiyama et al., J. Immunol. 177 (2006) 566-73). In line with this basic understanding of the immune pathology of EAE, we suspected that the magnitude of the CNS antigen-specific T-cell response might be reflected by the frequencies of the IFN-γ or IL-17 producing T-cells is the primary criterion that defines the severity of the disease.

It has been established that after immunization with CNS antigen including PLP peptide (PLPp) and MOG peptide (MOGp), the frequencies of IFN-γ and IL-17 producing cells in draining lymph nodes (drLNs) and spleen are highly variable, ranging from very low to rather high (H. H. Hofstetter et al., J. Immunol. 174 (2005) 4598-4605). It is also well known that the severity of the disease shows considerable interindividual fluctuations, ranging from mild to lethal, even when keeping the variables that could influence the disease outcome constant (e.g. age of the mice at immunization, gender, genetic background, colony etc.) (H. H. Hofstetter et al., J. Immunol. 174 (2005) 4598-4605; S. Kuerten et al., J. Neuroimmunol. 189 (2007) 31-40). Taking the causative relationship between CD4+ T-cells producing IFN-γ and IL-17 and the development of EAE into account, we suggest that the magnitude of the T-cell response and the disease severity will be in direct correlation to each other. In other words, those mice that do not develop severe disease, for example, due to their T-cell repertoires, will not display a high frequency of effector cells, whereas a high effector cell mass will accumulate in those mice, in which the pathology is severe enough to cause lethality.

However, this hypothesis has previously not been tested in mice. This is because T-cell assays typically require $5 \times 10^5$ to $1 \times 10^6$ cells per test condition, and if one includes control and experimental sets in replicates, then 3 to $6 \times 10^6$ cells may be needed for a single measurement. For this reason, most immune monitoring in mice has been performed with lymphoid tissue such as drLNs and spleen, from which sufficient cell numbers can be obtained for testing. Needless to say, mice have to be sacrificed for such tests. Therefore, no information can be obtained as to what clinical disease would have looked like if they had been permitted to live longer.

We introduced an ELISPOT assay for testing mouse blood in order to move closer to the human standard where blood is the primary sampling site for measuring T-cell reactivity (H. H. Hofstetter et al., J. Immunol. 174 (2005) 4598-4605).

For these first generation murine blood assays, a sufficient amount of blood was obtained for examining individual mice, but only if the mice were sacrificed. Thus, these assays were not suited for longitudinal studies. Here we developed a variant of the assay that functioned with only 150 µl of blood and thereby permitted repeated bleeding of individual mice, while the clinical course of EAE could be observed over time.

To study both IFN-γ and IL-17, we performed double-color measurements. These technical advances enabled us to experimentally address one of the weighty outstanding questions in autoimmune research, that is, how the T cell reactivity in the blood is reflective of the clinical course of disease in individual mice.

Example 6: Materials and Methods

Mice

Female SJL/J and C57BL/6 (B6) mice (6-8 weeks old) were purchased from the Jackson Laboratory (Bar Harbor, Me.) and maintained at the animal facilities of Case Western Reserve University, Cleveland, Ohio, USA under specific pathogen-free conditions. All treatments were performed according to an approved IACUC protocol and complied with the institutional guidelines.

Induction and Clinical Assessment of EAE

Incomplete Freund's Adjuvant (IFA) was prepared as a mixture of mannide monooleate (Sigma-Aldrich Corp., St. Louis, Mo.) and paraffin oil (EMScience, Gibbstown, N.J.), CFA was obtained by mixing *Mycobacterium tuberculosis* H37RA (Difco Laboratories, Franklin Lakes, N.J.) at 5 mg/ml into IFA. For disease induction, mice were immunized subcutaneously in both sides of the flank with a total dose of 100 µg PLP peptide 139-151 (SJL/J) or 100 µg MOG peptide 35-55 (B6). Both peptides were obtained from Princeton Biomolecules, Langhorne, Pa. 200 ng pertussis toxin (PTx; List Biological Laboratories, Hornby, ONT, Canada) in 500 µl sterile PBS was given on the day of immunization and 48 h later. Control mice received both CFA and PTx, however in the absence of CNS antigen. Clinical assessment of EAE vas performed daily according to the following criteria: (0), no disease; (1), floppy tail; (2), hind limb weakness; (3), full hind limb paralysis; (4), quadriplegia; (5), death. Mice that were in between the clear-cut gradations of clinical signs were scored intermediate in increments of 0.5.

Cell Preparations from Various Organs

Mouse blood (150 µl per mouse and time point) was collected by tail vein bleeding using heparin as anti-coagulant. The blood was diluted at 1:2 with sterile calcium-free PBS. After centrifugation, red blood cells were lysed with ammonium chloride. Cells were then washed thoroughly with HL-1. Single cell suspensions from spleen and draining lymph nodes were prepared as previously described (H. H. Hofstetter et al., J. Neuroimmunol. 170 (2005) 105-114). All cells were counted using acridine orange/ethidium bromide (Sigma-Aldrich Corp.).

ELISPOT Assays and Image Analysis

Whatman Unifilter low-volume plates (Whatman Inc., Florham Park, N.J.) were coated overnight with the capture antibodies in sterile PBS. AN-18 (eBioscience, San Diego, Calif.) was used at 3 µg/ml for capturing IFN-γ and TC-11-18H10 (BD Pharmingen, San Jose, Calif.) at 4 µg/ml for IL-17. For double-color assays, anti-IFN-γ antibody was applied to the plate 10 min before the addition of anti-IL-17 antibody. The plates were blocked for 2 h at room temperature with sterile PBS containing 1% bovine serum albumin (Sigma-Aldrich Corp.). The cells were plated in HL-1 supplemented with 1 mM glutamine without (medium) or with antigen (final concentration of 15 µg/ml for both MOG:35-55 and PLP:139-151). The plates were cultured at 37° C. and 7% $CO_2$ for 24 h. Subsequently, the detection antibodies were added for overnight incubation, FITC-labelled rat anti-mouse R4-6A2 (purified and HTC-labelled in our laboratory) was used at 0.5 µg/ml for detecting IFN-γ, while rat anti-mouse TC11-8H4.1-biotin was used for the detection of IL-17 (BD-Pharmingen; 0.5 µg/ml). For double-color assays, both antibodies were added at the same time. As a third reagent for IFN-γ anti-FITC-AP (Dako North America, Inc., Carpinteria, Calif.) was added at 1:500 dilution in PBS containing 1% BSA and 0.025% Tween 20, and Streptavidin-HRP (Dako) was added at 1:1000 for IL-17. After incubation for 2 h at room temperature, plates were developed using the Vector Blue substrate kit (Vector Laboratories, Inc., Burlingame, Calif.) for visualizing IFN-γ and AEC substrate solution (Cellular Technology Limited, Cleveland, Ohio) for IL-17. For double-color assays, blue spots were developed prior to red spots. The plates were analyzed on an ImmunoSpot® Series 5 Analyzer (ImmunoSpot is a Registered Trademark of Cellular Technology Limited, Shaker Heights, Ohio). All results were normalized to $10^6$ cells, and the difference between stimulated and non-stimulated cells was calculated.

Statistical Analysis

SigmaStat software (Version 7.0; SPSS, Chicago, Ill.) was used to assess correlation coefficients and the statistical significance of the differences between two groups using Student's t-test. Statistical significance was set at $P \leq 0.05$.

Example 7: PLPp-Specific and MOGp-Specific IFN-γ and IL-17 Producing T-Cells and Initial Disease Severity Given that the primary variable that defines the immune pathology of EAE is the CNS antigen specific T-cell response, we carried out studies to determine if the magnitude of this response is correlated with the severity of the disease. This hypothesis was assessed in n=16 SJL mice that were immunized with PLPp in CFA, with PTx given on the day of immunization and 48 h later. We also studied B6 mice immunized using MOGp.

All mice were bled on day 10 after immunization and the magnitude of the PLPp-specific T-cell response was determined in double-color IFN-γ/IL-17 ELISPOT assays. The resulting IFN-γ and IL-17 spot numbers were then correlated with the maximal severity of the following initial disease episode that typically occurred on day 13 after immunization in the SJL model.

Figure 5A:
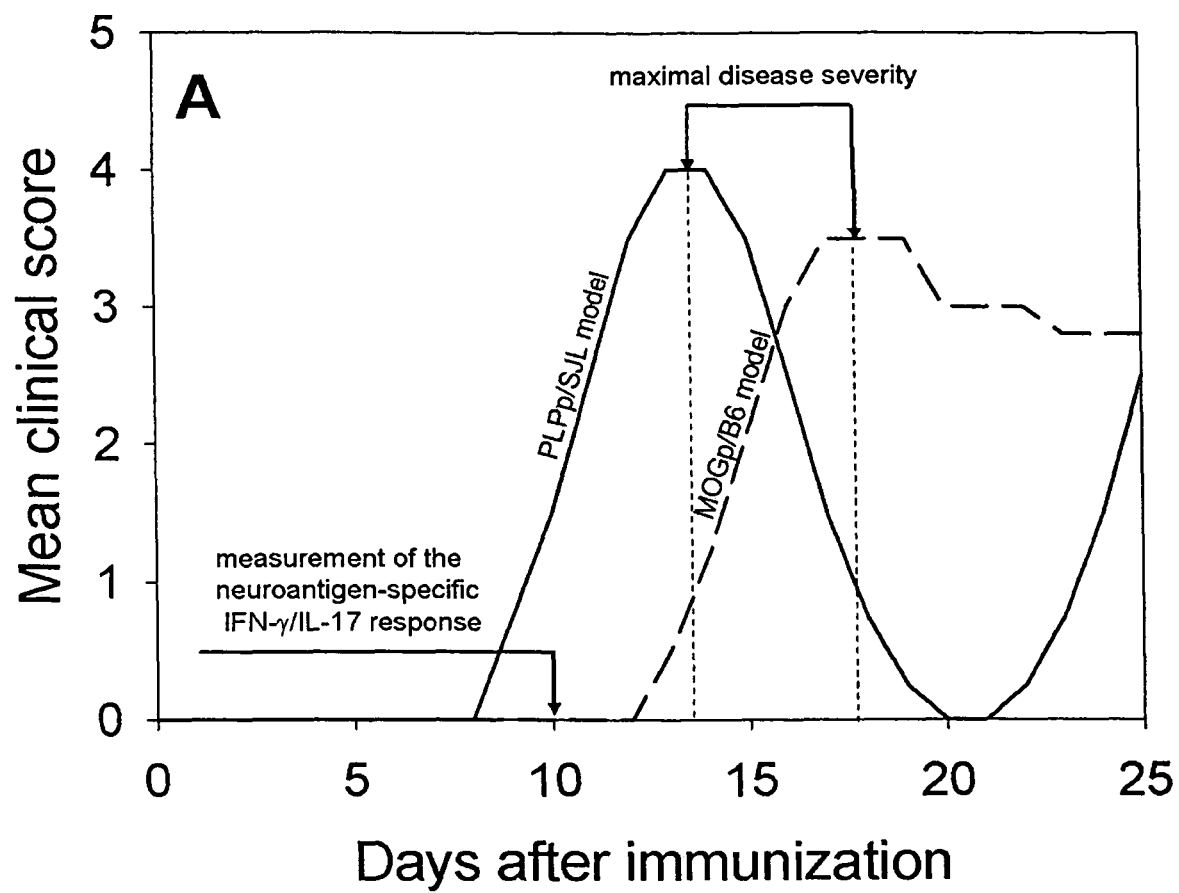
FIG. 5A depicts a graph schematically showing the mean clinical score in the PLPp/SJL and the MOGp/B6 model. By about 8 days after immunization, the PLPp-treated SJL mice showed increasing severity until reaching a maximum at about day 14. In MOG-treated B6 mice, the appearance of clinical symptoms began at about day 13, and the symptom score increased until about day 18.

FIG. 5A depicts a graph schematically showing the mean clinical score in the PLPp/SJL and the MOGp/B6 models. By about 8 days after immunization, the PLPp-treated SJL mice showed increasing severity until reaching a maximum at about day 14. In MOGp-treated B6 mice, the appearance of clinical symptoms began at about day 13, and the symptom score increased until about day 18. FIG. 5A also shows that the antigen-specific IFN-γ and IL-17 response measured on day 10 after immunization and the subsequent maximal disease severity.

Figure 5B:
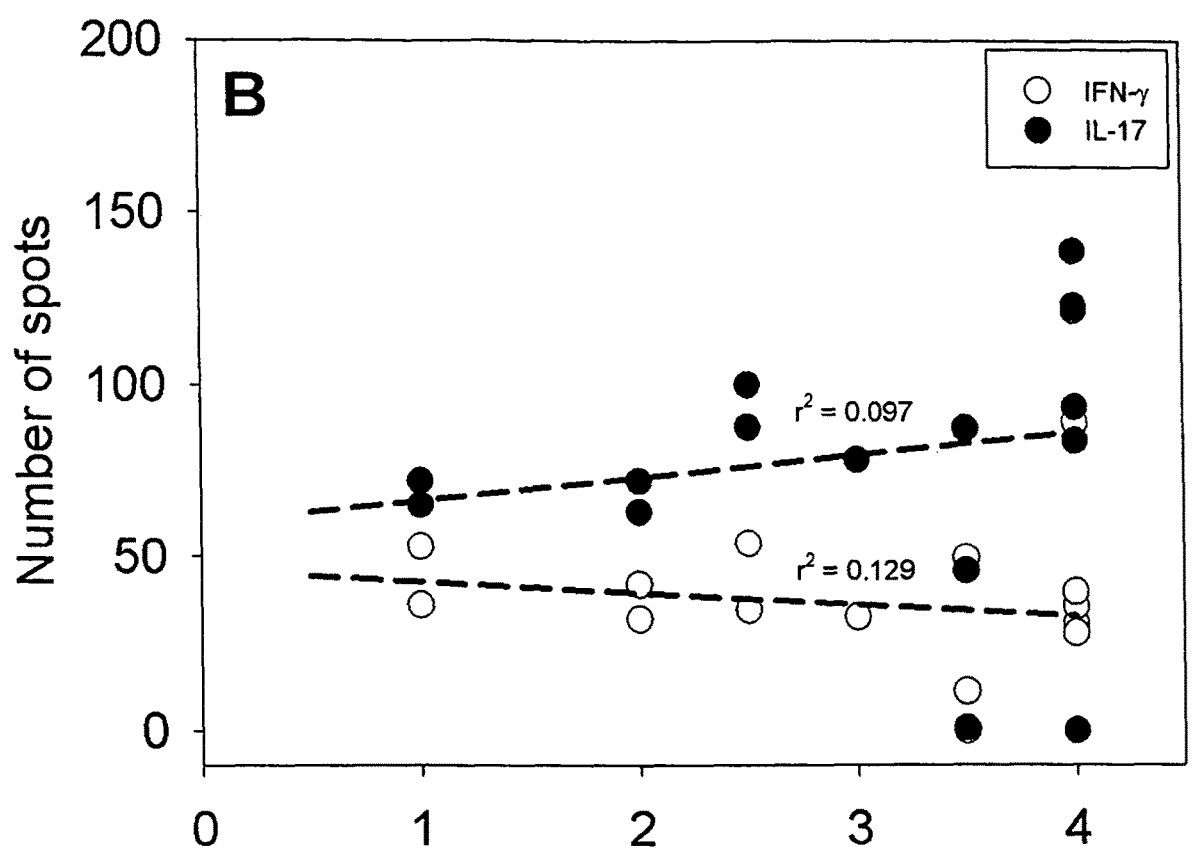
FIG. 5B depicts a graph of the correlation between the magnitude of the PLPp-specific IFN-γ (white circles) and IL-17 (black circles) responses (vertical axis) and the maximal severity of the initial disease episode in SJL mice (horizontal axis). Each circle refers to an individual mouse.
Figure 5:
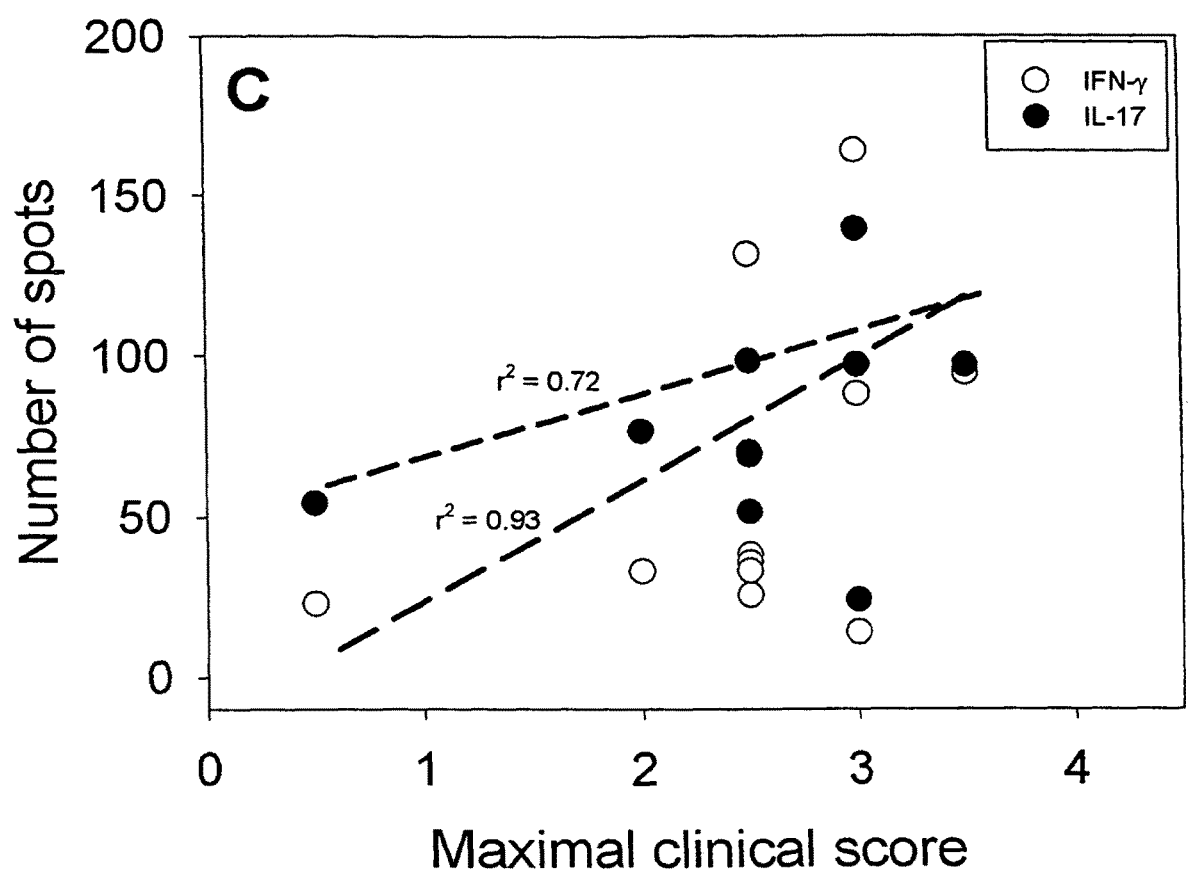
FIG. 5 depicts a graph showing absent versus positive correlation between the frequencies of CNS antigen-specific IFN-γ and IL-17 producing T-cells and initial disease severity in PLPp- vs. MOGp-induced EAE of SJL and B6 mice, respectively. N=16 SJL and n=10 B6 mice were immunized with the respective CNS antigen. On day 10 after immunization, PBMCs were isolated from the blood (collected from the tail vein) and tested for their CNS antigen-specific IFN-γ and IL-17 response in double-color ELISPOT assays. The magnitude of the T-cell response was correlated with the maximal onset severity of the disease in all mice.
Figure 6:
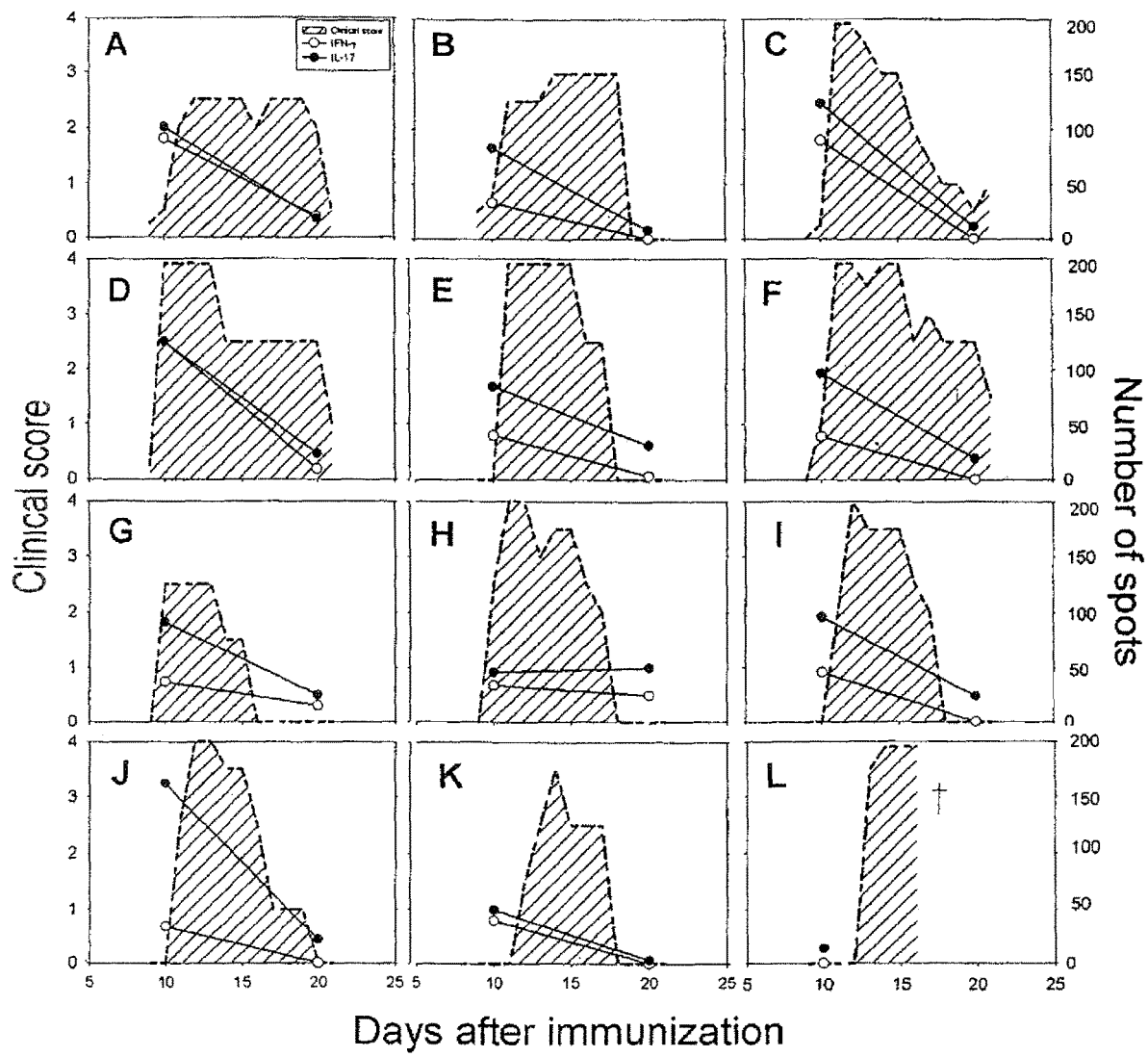
FIGS. 6A-6L depict graphs of data showing that recovery from initial EAE is accompanied by a drop in PLPp-specific T-cell frequencies in PLPp-induced EAE of SJL mice. N=12 individual SJL mice (A-L), were immunized with PLPp. PBMCs were isolated on days 10 and 20 after immunization, corresponding to the initial episode of the disease and the remission, respectively.

FIG. 5B depicts a graph of the correlation between the magnitude of the PLPp-specific IFN-γ (white circles) and IL-17 (black circles) responses (vertical axis) and the maximal severity of the initial disease episode in SJL mice (horizontal axis). Each circle refers to an individual mouse.

FIG. 5C depicts the correlation between the magnitude of the MOGp-specific IFN-γ (white circles) and IL-17 (black circles) responses (vertical axis) and the maximal onset severity in B6 mice (horizontal axis, n=10). Each circle refers to an individual mouse. Results are representative of two independent experiments performed. All results are medium-subtracted and normalized to $10^6$ cells. In this model a correlation between the magnitude of the MOGp-specific IFN-γ and IL-17 response measured prior to EAE onset and the consecutive maximal disease severity was evident ($r^2$=0.93 for IFN-γ, $r^2$=0.72 for IL-17). In the MOGp model the onset severity ranged from 0.5 to 3.5 and was typically reached on day 18 after immunization.

Example 8: Clinical Recovery from Initial EAE is Accompanied by a Drop in PLPp-Specific T-Cells in PLPp-Induced EAE The double-color ELISPOT assay that we developed functioned with as little as 150 μl of murine blood. This allowed us to repeatedly measure the CNS antigen-specific T-cell responses in individual mice while following up on the clinical course of EAE. N=12 SJL mice were immunized with PLP peptide 139-151 in CFA, with PTx given on the day of immunization and 48 h later. On days 10 and 20 after immunization, corresponding to the acute stage of EAE and remission, mice were bled and the PLPp-specific IFN-γ and IL-17 responses were assessed.

Results are shown in FIGS. 6A-6L, with each panel referring to an individual mouse. In 10 out of 12 mice tested, the clinical recovery from EAE was accompanied by a drop in PLPp-specific T-cell frequencies (FIGS. 6A-6K), in one mouse (FIG. 6H) the frequencies were unchanged; one mouse died of EAE (FIG. 6L).

The magnitudes of the PLPp-specific IFN-γ and IL-17 responses were assessed in each individual mouse (FIGS. 6A-6L) on both time points in double-color ELISPOT assays. Open circles refer to IFN-γ and black circles to IL-17 (right vertical axis). The shaded areas denote the clinical score course (left vertical axis) over time after PLPp-induced EAE (horizontal axis). When calculating the mean PLPp-reactive T-cell frequencies for all mice, there was a significant decrease in IFN-γ spots from a mean of 55.9 to 7.1 spots per $10^6$ cells (p=0.0004). The same applied to IL-17. Here, the number of spots decreased from a mean of 89.5 to 23.4 spots per $10^6$ cells (p=0.0001). IFN-γ and IL-17 followed a similar trend. Results are medium-subtracted, normalized to $10^6$ cells, and representative of two independent experiments. In 10 of the animals, there was an initial high level of spots detected using the double-color assay of this invention. This initial high level of spots correlated with the onset of EAE. As the course of the EAE progressed, and the clinical score decreased (with remission of the symptoms), the number of spots decreased. Thus, there was a direct and substantial correlation between immune cell responses and clinical severity in EAE.

Example 9: Relapse and Increase of PLPp-Specific T-Cells in PLPp-Induced EAE

The dynamics of PLPp-specific T-cell frequencies relative to the clinical course of EAE were further assessed by comparing remission and relapse. The same n=12 SJL mice shown in Example 8 as above were additionally bled on day 30 after immunization corresponding to the clinical relapse. PBMCs were isolated and again tested for their PLPp-specific IFN-γ/IL-17 responses in double-color ELISPOT assays.

FIGS. 7A-7L depict graphs of PLPp-specific T-cell responses in individual mice over time (right vertical axis), compared to the appearance of clinical relapse (shaded area; left vertical axis) in SJL mice with time after immunization with PLPp-induced EAE (horizontal axis). Open circles refer to IFN-γ and black circles to IL-17 (right vertical axis). In 9 out of 12 mice tested, the relapse of disease was accompanied by a remarkable increase in PLPp-specific T-cell frequencies (FIGS. 7A-G, 7J and 7K. In 10 of these animals, there was a direct correlation between IFN-γ producing T-cells, IL-17 producing T-Cells and clinical severity during the relapse phase of EAE.

Figure 7:
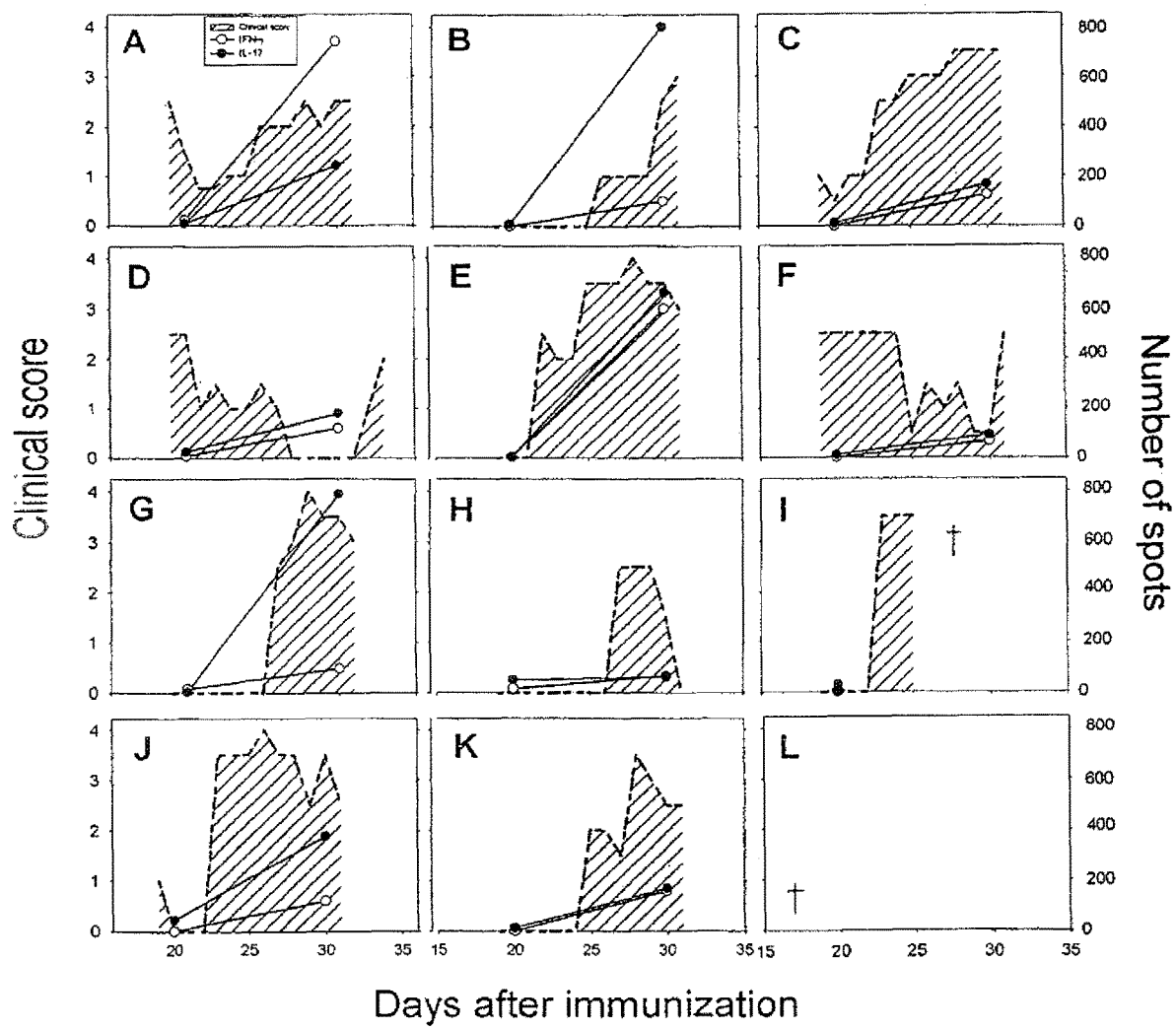
Figure 8:
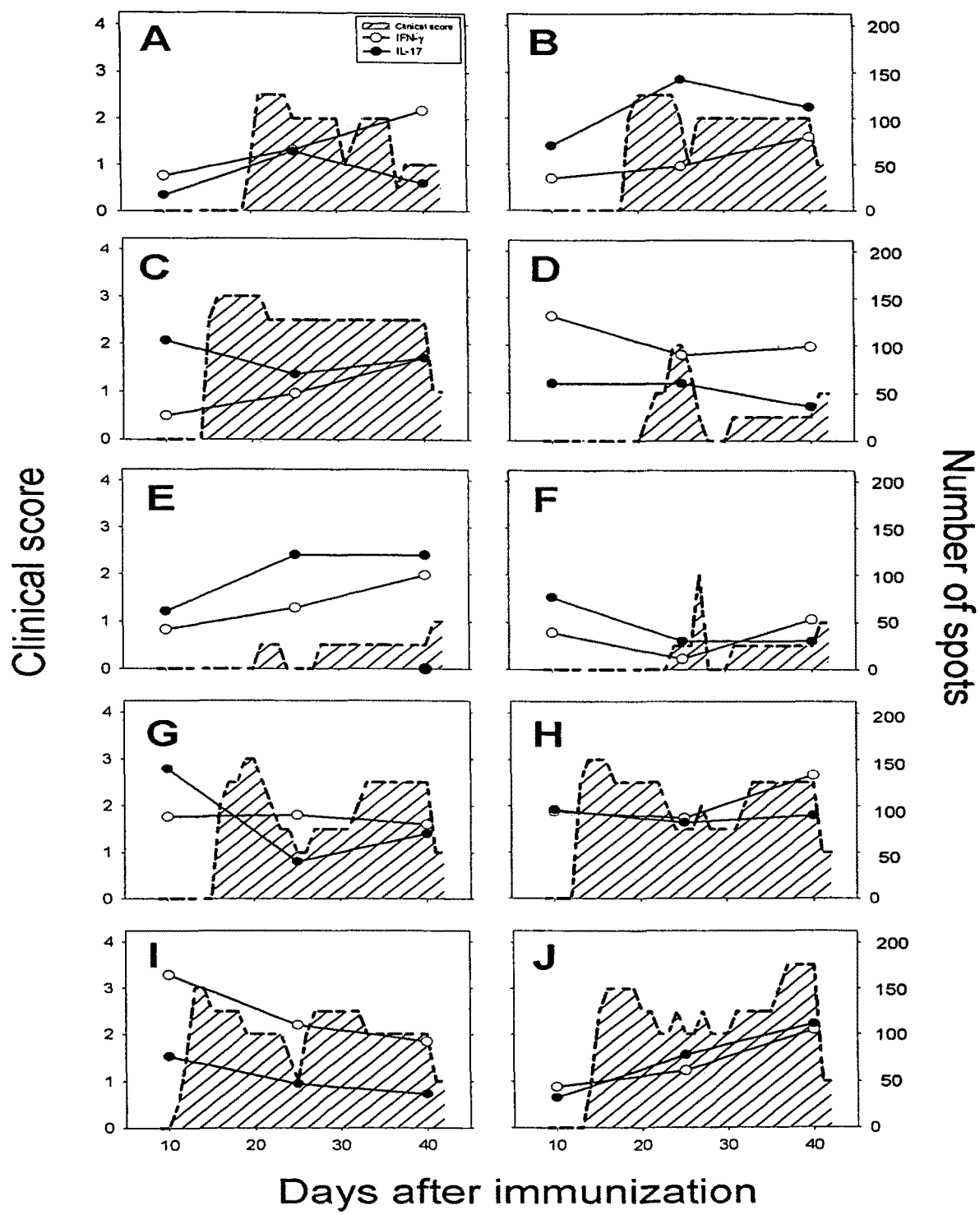

In one mouse the frequencies remained unchanged (FIG. 7H). Two mice died of EAE (FIGS. 7I and 7L). Taking all mice together, spot counts significantly increased from a mean of 7.1 to 212.5 IFN-γ spots per $10^6$ cells (p=0.005) and from a mean of 23.4 to 320.2 IL-17 spots per $10^6$ cells (p=0.01). Overall, both antigen-specific IFN-γ and IL-17 responses behaved similarly.

Example 10: Course of Disease in MOGp-Induced EAE Parallels MOGp-Specific T-Cell Response As the dynamics of clinical disease were reflected by fluctuations in the T-cell compartment in PLPp-induced EAE of SJL mice, we assessed whether the chronic course of the disease was equally accompanied by stable frequencies of MOGp-specific T-cells in MOGp-induced EAE of B6 mice. N=10 B6 mice were immunized with MOGp in CFA and PTx was given on the day of immunization and 48 h later. Mice were bled on days 10, 25 and 40 after immunization. PBMCs were isolated and tested for their MOGp-specific IFN-γ and IL-17 response in double-color ELISPOT assays while we followed up on the clinical course of EAE.

Results are shown in FIGS. 8A-8J, with each panel representing the results for an individual mouse. FIGS. 8A-8J depict graphs of IFN-γ and IL-17 producing T-cells (detected using the double-color assay of this invention; right vertical axis) and the chronic disease course (shaded areas; left vertical axis) versus time after immunization of 10 individual B6 mice innoculated with MOGp. White circles refer to IFN-γ and black circles to IL-17. The shaded areas denote the clinical disease course over time. Results are medium-subtracted, normalized to $10^6$ cells, and representative of three independent experiments. MOGp-induced EAE is paralleled by stable frequencies of MOGp-specific T-cells. N=10 individual B6 mice (FIGS. 8A-8J) were immunized with MOGp. PBMCs were isolated on days 10, 25 and 40 after immunization, reflecting the pre-onset, peak and chronic stage of the disease, respectively.

In 10 out of 10 mice, the chronic non-remitting-relapsing course of EAE was reflected by stable frequencies of MOGp-specific IFN-γ producing T-cells (means of 64.7, 60.2 and 72.7 for days 10, 25 and 40 with p=0.81 and p=0.45 respectively). The same applied to IL-17 (means of 69.2, 60.3 and 67.2 for days 10, 25 and 40 with p=0.63 and p=0.77, respectively). Again, both cytokines—IFN-γ and IL-17—followed a similar trend.

FIG. 9 summarizes the relationship between the frequencies of IFN-γ/IL-17 producing T-cells and the clinical disease course in both models. FIGS. 9A-9F depict graphs of antigen-specific IFN-γ and IL-17 response versus time after immunization in the blood of PLPp- and MOGp-immunized SJL/J (FIGS. 9A, 9C and 9E) and B6 (FIGS. 9B, 9D, and 9F)

mice, respectively. In FIGS. 9A, 9C and 9E, SJL/J mice were immunized with PLPp. Mean clinical EAE scores were assessed daily (FIG. 9A). On days 10, 20 and 30 150 µl of blood was obtained from the tail vein, PBMCs were isolated and tested for their PLPp-specific IFN-γ (FIG. 9C) and IL-17 (FIG. 9E) responses in double-color ELISPOT assays. In FIG. 9B, B6 mice were immunized with MOGp. EAE scores were assessed daily. On days 10, 25 and 40 150 µl of blood was obtained from the tail vein, PBMC isolated and tested for their MOGp-specific IFN-γ (FIG. 9D) and IL-17 (FIG. 9F) response as above.

These results indicate that under the conditions of this study, PLPp appeared to produce greater severity of EAE and larger IFN-γ and IL-17 responses than did MOGp.

Example 11: B-Cell-Deficient µMT and $J_HT$ Mice are Resistant to MP4-Induced EAE In our initial characterization of the MP4 model we found that MP4-immunized µMT mice did not develop clinically severe EAE. Here we additionally performed histological analysis. Moreover, we included $J_HT$ mice, a different B-cell-deficient strain. WT B6 and B-cell-deficient µMT and $J_HT$ mice were immunized with 150 µg MP4 in CFA. PTX was injected on days 0 and 2. The clinical course of the disease was assessed over a period of 40 days and is shown in FIG. 10A: wild-type (n=11; filled circles), µMT mice (n=8; open squares) and $J_HT$ mice (n=5; open triangles). Clinical scores were assessed daily according to the standard scale. Results are displayed as mean+SD and were reproduced in two additional independent experiments.

As depicted in FIG. 10A, all WT B6 mice (n=11) developed EAE with a mean disease onset on day 9.4±1.9 and a mean maximal clinical score of 2.56±0.85. Upon histological examination, WT mice showed degenerative plaque formation in the white matter, in particular in the anterolateral tract. The plaques were characterized by cellular infiltration, severe demyelination and axonal loss (FIG. 10B).

In contrast, in the B-cell-deficient mice, no pathological changes were detected (FIG. 10D). These light microscopic results were confirmed by ultrastructural analysis (FIGS. 10C and 10E). Neither µMT (n=8) nor $J_HT$ (n=5) mice showed any clinical signs of EAE. On day 40 after immunization, mice were sacrificed and histological analysis of CNS tissue was performed.

Example 12: Myelin-Reactive Antibodies Mediate the Pathology of MBP-PLP Fusion Protein MP4-Induced EAE Introduction Experimental autoimmune encephalomyelitis (EAE) is generally considered a model for multiple sclerosis (MS) (M. Sospedra and R. Martin, Annu. Rev. Immunol. 23 (2005) 683-747; R. Gold et al., Brain 129 (2006) 1953-1971). EAE can be induced by immunization with various myelin antigens. The initial EAE models entailed inoculation of crude spinal cord (E. A. Kabat et al., Res. Publ. Assoc. Res. Ner. Ment. Dis. 28 (1950) 113-132; J. Freund et al., Arch. Pathol. (Chic.) 50 (1950) 108-121; S. Levine and R. Sowinski, J. Immunol. 110 (1973) 139-143). Over the decades, they were replaced by increasingly defined systems, in which disease was elicited with purified antigens. At first, these antigens were proteins isolated from the brain and included myelin basic protein (MBP), proteolipid protein (PLP) and later myelin oligodendrocyte glycoprotein (MOG). Because such protein preparations are not necessarily pure and frequently not easy to obtain, the field progressed towards work with synthetic peptides.

In all EAE models studied so far it has become evident that CNS antigen-specific antibodies alone are insufficient to cause CNS pathology that is reminiscent of MS: injection of serum from myelin antigen- or antigenic peptide-immunized mice into naïve recipients does not induce EAE (S. H. Appel and M. B. Bornstein, J. Exp. Med. 119 (1964) 303-312; D. O. Willenborg, Scand. J. Immunol. 16 (1982) 437-441). Because the immunization of wild-type (WT) animals typically elicits T-cell and B-cell responses in parallel, it cannot be mechanistically dissected whether the accompanying antibody response is merely a bystander phenomenon or plays an additional role in accelerating the disease. Only the introduction of B-cell knock-out (KO) mice has enabled progress with studies that clearly distinguish between the T-cell and B-cell contribution to the disease process. These KO mice are on the C57BL/6 (B6) background that is particularly susceptible to MOG- and MOG peptide-induced EAE (while being relatively resistant to MBP or MBP peptide immunizations). A milestone paper demonstrated that immunization of B-cell-deficient µMT mice on the B6 background with MOG peptide 35-55 causes EAE that is similar to WT mice in course and severity (P. Hjelmstrom et al., J. Immunol. 161 (1998) 4480-4483). These results supported the prevailing thought that antibodies/B cells are not required for EAE pathogenesis. A later extension of these studies modified this notion showing that antibodies induced by immunization with human MOG protein (as opposed to rat MOG) contribute to EAE (while being not pathogenic on their own) [9-12]. These data provided the first direct evidence that MOG-specific antibodies can play a role in MOG-induced EAE. However, they have left the questions open if autoantibodies to other myelin antigens can be pathogenic in EAE and possibly also in MS.

The question of the pathogenetic significance of myelin-specific autoantibodies is of particular interest because in MS such autoantibodies can be regularly detected in the serum and cerebrospinal fluid (CSF) and in CNS lesions of patients (P. Dharmasaroja, J. Neurol. Sci. 206 (2003) 7-16; Y. Qin and P. Duquette, Int. MS J. 10 (2003) 110-120; T. Ziemssen and F. Ziemssen, Autoimmun. Rev. 4 (2005) 460-467; P. Martin Mdel and N. L. Monson, Front. Biosci. 12 (2007) 2735-2749; K. A. McLaughlin and K. W. Wucherpfennig, Adv. Immunol. 98 (2008) 121-149; S. Kuerten et al., Fortschr. Neurol. Psychiatr. 79 (2011) 83-91). The same applies to Devic's disease, also known as neuromyelitis optica (NMO), which is frequently considered a variant of MS. NMO primarily affects the optic nerve and spinal cord and is focused on an autoantibody response, in particular against aquaporin-4. Similar to MS, many aspects of the pathogenesis of NMO have remained unclear (S. Janus et al., Nat. Clin. Pract. Neurol.4 (2008) 202-214.

Among the autoantigens for which EAE models are available, MBP and PLP are frequently targeted by autoantibodies in MS. In humans it is impossible to experimentally establish whether antibodies against MBP and PLP indeed play a pathogenic role or occur as epiphenomena of the disease. MBP-specific antibodies are unlikely to be pathogenic at least in the initial stages of the disease since MBP is an intracellular protein and as such not accessible to antibodies on intact myelin. In EAE there is little and controversial evidence for a pathogenic role of MBP-specific antibodies (M. Morris-Downes et al., J. Neuroimmunol. 125 (2002) 114-124; Z. Jingwu et al., J. Neuroimmunol. 24 (1989) 87-94).

PLP is a more likely candidate for antibody-mediated pathology. PLP is a transmembranous protein. Two of its seven domains are located on the myelin surface readily accessible to antibodies (V. K. Tuohy, Neurochem. Res. 19 (1993) 935-944). Presently, it is not established whether PLP specific antibodies can contribute to EAE pathogenesis. Addressing this question was hampered by the extreme hydrophobicity of the PLP molecule, which made experimental work with the native protein rather difficult. Among PLP peptides, the sequence 139-151 is strongly pathogenic in SJL mice and hence this peptide and mouse strain combination has become the classic PLP model. In this model antibodies do not play a pathogenic role (N. T. Potter and T. S. Stephens, J. Neurosci. Res. 37 (1994) 15-22; B. L. McRae and S. D. Miller, Neurochem. Res. 19 (1994) 997-1004). It should be noted, however, that the 139-151 PLP peptide sequence occurs intracellularly, leaving the question open whether antibodies that recognize extracellular PLP domains could participate in the disease.

The role of PLP-specific autoantibodies can be studied using the MP4-induced EAE model. MP4 is a fusion protein of human MBP and an engineered form of PLP, which contains the three hydrophilic domains including the two extracellular loops (while the hydrophobic parts have been omitted) (E. A. Elliott et al., J. Clin. Invest. 98 (1996) 1602-1612; S. Kuerten et al., J. Neuroimmunol. 177 (2006) 99-111). B6 mice are weak responders to MBP (C. C. Bernard, J. Immunogenet. 3 (1976) 263-274; S. S. Zamvil et al, Nature 324 (1986) 258-260; R. B. Fritz and M. L, J. Neurosci. Res. 5 (1996) 471-474), and due to the intracellular localization of MBP, the PLP-specific component of the MP4-induced antibody response should prevail if indeed MP4-induced antibodies contribute to the disease.

We established that B6 are susceptible to MP4-induced disease. Therefore, the MP4 model in WT versus congenic B-cell KO mice provides a new system for studying the pathogenic role of MBP/PLP-specific antibodies. In our initial characterization testing B-cell-deficient mice, we demonstrated that MP4-induced EAE was B-cell-dependent. B-cells can play various roles in the disease process. On the one hand, they could be useful as antigen presenting cells triggering the MBP-PLP-specific T-cell response in MP4-immunized mice. On the other hand, MBP-PLP-specific antibodies could be involved in disease development. The experiments reported herein were designed to directly address the latter hypothesis. We showed that MBP/PLP-specific autoantibodies, when transferred into MP4-immunized B-cell-deficient mice, can convert such mice from resistant to fully EAE susceptible. These data establish that MBP-PLP-specific antibodies do not only contribute to the disease, but are a significant component of MBP/PLP-induced EAE in B6 mice. The demonstration of a pathogenic role of MBP-PLP-specific antibodies in mice indicates that such antibodies can also play a role in human patients with MS.

Materials and Methods

Mice

Female B6 and B-cell-deficient μMT mice on a C57BL/6 background were purchased from the Jackson Laboratory (Bar Harbor, Me.), $J_HT$ mice were a kind gift from Ari Waisman (University of Mainz, Germany). All mice were 6-8 weeks old at the time of treatment. The mice were maintained at our local animal facilities under specific pathogen-free conditions. All treatments were performed according to an approved protocol and complied with the institutional guidelines.

Example 13: Immunizations

The MBP-PLP fusion protein MP4/Apogen (SEQ ID NO. 6; containing the 21.5 kD isoform of human MBP and the three hydrophilic domains of PLP) was obtained from Alexion Pharmaceuticals (Cheshire, Conn.). Incomplete Freund's adjuvant (IFA) was prepared as a mixture of Mannide Monooleate (Sigma-Aldrich, St. Louis, Mo.) and Paraffin Oil (EMScience, Gibbstown, N.J.), complete Freund's adjuvant (CFA) was obtained by mixing *Mycobacterium tuberculosis* H37 RA (Difco Laboratories, Franklin Lakes, N.J.) at 5 mg/ml into IFA. For active immunization, B6, μMT or $J_HT$ mice were immunized subcutaneously in both sides of the flank with a total dose of 150 μg MP4, 100 μg MOG:35-55 or 200 μg OVA in CFA. Control-immunized mice received PBS in CFA. Pertussis toxin (PTX; List Biological Laboratories, Hornby, ONT, Canada) was given at 200 ng per mouse on the day of immunization and 48 h later. For passive transfer experiments, the protocol of Lyons et al. (Eur. J. Immunol.32 (2002) 1905-1913) was used with μMT or $J_HT$ mice receiving four 150 μl-injections of pooled antisera at 3-day intervals for a total of 600 μl. The donor sera had been obtained from WT B6 mice 20, 30, 40 and 50 days after immunization with MP4, OVA or PBS in CFA. In addition, serum was obtained from naïve WT B6 mice. The presence or absence of antigen-specific antibodies in the serum samples was confirmed by ELISA. Clinical assessment of EAE was performed daily according to the following criteria: (0), no disease; (1), floppy tail; (2), hind limb weakness; (3), full hind limb paralysis; (4), quadriplegia; (5), death. Mice that were in between the clear-cut gradations of clinical signs were scored intermediate in increments of 0.5.

Example 14: MP4-Immunized B6 Mice Develop MP4-Specific IgG1 and IgG2a Antibodies Because MP4-induced EAE was bound to be B-cell-dependent, the question arose whether MP4-specific antibodies were present in the serum of MP4-immunized WT B6 mice. To this end, ELISAs were performed measuring MP4-specific IgG, IgG1 and IgG2a in MOG:35-55-immunized WT B6 and MP4-immunized WT B6 and μMT mice. In MOG peptide-immunized mice there was only a slight elevation in MOG:35-55-specific antibody titers starting on day 32 after immunization (FIG. 11A). While in MP4-immunized μMT mice (n=8) MP4-reactive antibodies were absent (FIG. 11B), in WT B6 mice immunized with MP4 (n=8) antibodies reactive to MP4 were evident as early as 15 days after immunization (FIG. 11C). The MP4-specific antibody response reached a plateau around day 40 after immunization. The MP4-specific antibodies were of the IgG1 and IgG2a isotype, with IgG1 apparently prevailing, but the difference did not reach statistical significance.

FIGS. 11A-11C depict graphs of optical density (vertical axis) of ELISA antibody assays of the immunoglobulins IgG (filled circles), IgG1 (hatched circles) and IgG2a (open circles) versus days after immunization (horizontal axis). FIG. 11A depicts results for WT B6 mice immunized with MOG peptide 35-55. FIG. 11B depicts results for μMT-treated mice immunized with MOGp 35-55. FIG. 11C depicts results in WT B6 mice immunized with 150 μg MP4 in CFA. PTX was given on days 0 and 2. Results are representative for a total of n=8 mice per group. Mean values±SD are shown.

From FIGS. 11A-11C, MOGp produced little (FIG. 11A) or no detectible (FIG. 11B) immune response. In striking contrast, immunization of wild-type B6 mice with MP4 produced striking increases in production of each type of immunoglobulin.

Example 15: MP4-Specific Antibodies are Myelin-Reactive

In another study, we investigated whether the antibody responses from mice with EAE are specific for CNS antigen. We removed spinal cords from mice using standard methods. We then compared the staining of longitudinal sections of spinal cords from different strains of mice immunized with CNS antigens.

FIGS. 12A-12C depict photomicrographs of 7 µm thick longitudinal sections of spinal cords from mice. FIG. 12A depicts a photomicrograph of spinal cord from a naive, control wild-type B6 mouse treated with MOG 35-55 serum. The detection of MP4 protein-specific antibodies in the serum of MP4-immunized mice does not necessarily prove that these antibodies are reactive to endogenous myelin. In order to prove myelin-reactivity, longitudinal spinal cord sections of naive WT B6 mice were incubated with serum from MOG peptide 35-55-immunized WT B6 mice (FIG. 12A).

FIG. 12B depicts a section of spinal cord from an animal treated with serum from an MP4-immunized µMT-treated animal exposed to MP4 serum. As with FIG. 12A, little staining was observed. FIG. 12C depicts a section of spinal cord from a B6 wild-type mouse treated with MP4 serum from a B6 wild-type mouse. In FIG. 12C, bands of myelin are shown, being labeled with antibodies from serum of MP4-immunized mice. The sera had been obtained on day 40 after immunization. Incubation of sections with MP4-specific serum resulted in a highly distinct staining of the myelin sheath architecture. All images are at 200× magnification. We conclude that MP4-specific antibodies in animals that develop EAE are myelin-reactive.

We tested whether WT B6 mice immunized with MP4 have antibody depositions in vivo and if such depositions are colocalized with demyelinated plaques. WT B6 mice (n=6) were either immunized with MOG peptide 35-55 or MP4 in CFA as above to develop EAE. Mice were sacrificed on day 40 after immunization, spinal cord sections obtained and stained with anti-mouse IgG to detect antibody depositions in the tissue. SMI-99 anti-MBP antibody was used to visualize myelin.

FIGS. 13A-13D depict photomicrographs of spinal cords from WT B6 mice immunized with MOG peptide 35-55 (FIGS. 13A and 13B) or MP4 (FIGS. 13C and 13D) showing antibody staining colocalized with demyelinated plaques. WT B6 mice were immunized with MOG:35-55/CFA or MP4/CFA, and PTX was given on days 0 and 2. On day 40 after immunization myelin was stained with anti-MBP antibody (FIGS. 13A and 13C), and the presence of antibody binding was detected by anti-IgG staining (FIGS. 13B and 13D). Results are shown for MOG:35-55-induced EAE (FIGS. 13A and 13B) and MP4-immunized WT B6 mice (FIG. 13C; MBP staining and 13D: IgG staining) MP4-immunized mice showed demyelinated plaques (FIG. 13C) that were colocalized with IgG depositions (FIG. 13D). All images are at 200× magnification and representative for a total of six MOG:35-55- and MP4-immunized mice, respectively. The images refer to MOG:35-55- and MP4-immunized mice having an average clinical EAE score of 2.5.

Example 16: Serum from MP4-Immunized WT Mice Renders MP4-Immunized B-Cell-Deficient Mice Susceptible to EAE In a first set of experiments naive µMT (FIG. 14A) and $J_HT$ (FIG. 14B) mice were injected with 4×150 µl of MP4-reactive serum i.p. (positivity had been confirmed by ELISA and myelin-reactivity by immunohistochemistry) on days 0, 4, 8 and 12. Clinically and histologically, the mice not immunized with MP4 showed no signs of EAE (FIGS. 14A-14C and 14F). To determine whether the blood-brain-barrier needed to be permeabilized for MP4-specific serum to induce pathology, naive µMT and $J_HT$ mice received PTX in addition to MP4-reactive serum as above. Again, EAE did not develop in mice not immunized with MP4 (FIGS. 14A, 14B, 14D and 14G). To establish whether antibodies were only able to induce EAE when MP4-specific T-cells were present, µMT and $J_HT$ mice were immunized with MP4 in CFA. PTX was given on days 0 and 2 and mice received 150 µl of MP4-reactive serum on days 0, 4, 8 and 12 after immunization as above.

We herein demonstrated transfer of MP4-reactive serum restores disease susceptibility in B cell-deficient MP4-immunized mice. B-cell-deficient µMT (FIG. 14A) or $J_HT$ (FIG. 14B) mice received 150 µl MP4-specific serum four times over 12 days. Mice either received serum alone (FIGS. 14A-14C, 14F, 14I) or combined with two injections of PTX on the first day of transfer and 48 h later (FIGS. 14A, 14B, 14D, 14G, 14J). A third group of mice was immunized with MP4 in CFA and received both PTX on days 0 and 2 and MP4-specific serum as indicated (FIGS. 14A, 14B, 14E, 14H, and 14K). Clinical scores were assessed daily (FIGS. 14A and 14B). Means+SD are shown. Spinal cord histopathology was assessed on day 30 after transfer. Representative methylene blue-stained sections (200× magnification) (FIGS. 14C-14E) and corresponding electron micrographs (3000× magnification) (FIGS. 14F-14H) are shown. In addition, spinal cord sections were stained for the presence of IgG depositions (FIGS. 14I-14K).

As shown in FIGS. 14A, 14B, 14E and 14H, mice immunized with MP4/CFA developed severe EAE and CNS histopathology was characterized by widespread demyelination and axonal damage, indistinguishable from the changes seen in WT B6 mice immunized with MP4 (see FIGS. 10B and 10C). Disease onset was on day 14.5±1.5 after immunization in the µMT and on day 11.8±0.4 in the $J_HT$ mice. The mean disease severity was 2.7±0.8 in µMT and 2.3±0.4 in $J_HT$ mice. The mean maximal severity was 2.8±0.3 in µMT and 2.8±0.2 in $J_HT$ mice (Table 2). Transfer of serum obtained from naive, control- or OVA-immunized WT B6 mice did not induce EAE (Table 2). In addition, in B-cell-deficient mice immunized with MP4 and receiving both PTX and MP4-reactive serum, antibody depositions were evident in the spinal cord. These depositions were absent in mice receiving serum alone or serum+PTX (FIGS. 14I-14K).

Example 17: Measurements of MP4-, MOG:35-55- and OVA-Specific Antibodies

ELISA plates (Nunc Immunoplate MaxiSorp; Fisher Scientific) were coated with 3 µg/ml MP4, 10 µg/ml MOG:35-55 or 3 µg/ml ovalbumin (OVA) in bicarbonate buffer overnight at 4° C. The plates were blocked for 2 hours with phosphate-buffered saline (PBS), containing 0.05 Tween 20 (PBST) and 1% BSA at room temperature. Subsequently, serum samples diluted in PBST/BSA, were added to the plate for overnight incubation at 4° C. Secondary antibodies used were biotinylated rat anti-mouse IgG (eBioscience, San Diego, Calif.), IgG1 and IgG2a (BD-Pharmingen, San Jose, Calif.). Streptavidin-AP or Streptavidin-HRP served as tertiary reagents (DakoCytomation, Glostrup, Denmark), both diluted at 1:1000 in PBST/BSA. Plates were developed with 100 µl/well of freshly prepared p-nitrophenylphosphate (p-NPP) solution (Sigma-Aldrich) or tetramethylbenzidine (TMB) (eBioscience).

Example 18: Immunohistochemistry

To analyze the myelin-reactivity of the serum samples 7 µm thick longitudinal spinal cord sections from naive untreated B6 mice that had been perfused with 4% PFA were cut on a Reichert-Jung Cryocut CM1850 cryostat (Leica, Wetzlar, Germany). For the evaluation of antibody depositions MOG:35-55-immunized WT B6 or MP4-immunized B-cell-deficient and WT B6 mice were perfused with 4% PFA on day 40 after immunization and 7 µm thick longitudinal spinal cord sections were obtained. All sections were air-dried for 2 hours at room temperature and fixed in methanol at −20° C. for 10 min. Staining was performed with the M.O.M. basic kit (Vector Laboratories, Burlingame, Calif.), following the vendor's instructions. For the analysis of myelin-reactivity serum was diluted at 1:50. For the detection of antibody depositions biotinylated anti-mouse IgG (M.O.M. kit reagent) was left on the sections for overnight incubation at 4° C. SMI-99 anti-MBP antibody (Covance, Princeton, N.J.) was used for the detection of myelin at 1:1000 dilution. All sections were incubated with Neutravidin Dylight549 fluorescent dye (Thermo Fisher Scientific, Rockford, Ill.) and Hoechst as nuclear counterstain (Sigma-Aldrich). Sections were observed with a Zeiss Axioskop™ 50 epifluorescence microscope. For fluorescence detection the "rhodamine" filter (Nr. 15 of Carl Zeiss, excitation BP 546/12, beamsplitter FT 580, emission LP 590) and the "ultraviolet" filter (Nr. 1 of Carl Zeiss, excitation BP 365/12, emission LP 397) were used. Digital images were acquired using a slow scan CCD camera (Leica) and software. The acquisition software ImagePro Plus™ (Media Cybernetics, Silver Spring) was used for consecutive image analysis.

Statistics

Differences between groups were assessed by Student's t-test. In case the Normality Test or the Equal Variance Test failed, the Mann-Whitney U rank sum test was used (calculated by SigmaPlot™, version 11.0). Statistical significance was set at $p \leq 0.05$. A summary of these studies is shown in Table 2 below.

TABLE 2

MP4-Specific Serum Restores Disease Susceptibility In EAE

| Mouse strain | Treatment | Disease incidence | Mean day of onset | Mean disease severity | Mean maximal disease severity | CNS pathology |
|---|---|---|---|---|---|---|
| C57BL/6 | none | 11/11 | 9.4 ± 1.9 | 1.7 ± 0.4 | 2.6 ± 0.9 | severe inflammation, demyelination and axonal loss |
| µMT | none | 0/8 | N/A | N/A | N/A | none |
| $J_HT$ | | 0/5 | | | | |
| µMT | MP4 serum | 0/2 | N/A | N/A | N/A | none |
| $J_HT$ | | 0/2 | | | | |
| µMT | MP4 serum + PTX | 0/4 | N/A | N/A | N/A | none |
| $J_HT$ | | 0/2 | | | | |
| µMT | MP4 immunized + | 3/3 | 11.8 ± 0.4 | 2.7 ± 0.8 | 2.8 ± 0.3 | severe |
| $J_HT$ | MP4 serum + PTX | 5/5 | 14.5 ± 1.5 | 2.3 ± 0.4 | 2.8 ± 0.2 | inflammation, demyelination and axonal loss |
| µMT | MP4 immunized + OVA serum + PTX | 0/6 | N/A | N/A | N/A | none |
| µMT | MP4 immunized + serum from control-immunized mice + PTX | 0/6 | N/A | N/A | N/A | none |
| µMT | MP4-immunized + serum from naive mice + PTX | 0/5 | N/A | N/A | N/A | none |

Example 19: Myelin-Specific Direct B-Cell Antibody Responses in a Patient with Multiple Sclerosis Using methods outlined herein, we obtained measurements of myelin-specific T cell responses and B-cell/antibody responses in MS and CIS patients. In a preliminary study, we measured the production of IgG and IgM antibodies from PMBCs from a patient with MS and compared the results with those from a normal human subject without MS. We used a Direct B-Cell assay of this invention, described herein above.

FIG. 15A depicts photographs of cell culture wells with cells from a patient with MS. Myelin-specific B-cells in MS patients with active disease using a Direct B-Cell assay. PBMCs isolated from the blood showed myelin-specific antibody secretion in response to application of MP4 ex vivo. Myelin-specific B-cell responses were observed for both IgG (FIG. 15A lower left photograph) and for IgM (FIG. 15A lower right photograph). The reaction was antigen-specific, because no responses were observed in response to medium alone (FIG. 15A top left and top right photographs).

In contrast, no MP4 responses were observed in PBMCs from healthy controls, either in the medium controls (FIG. 15B top left and top right photographs) or for IgG (FIG. 15B bottom left photograph) or IgM (FIG. 15B bottom right photograph). This reaction is antigen-specific and does not occur in the absence of antigen (medium controls).

Example 20: Myelin-Specific Indirect B-Cell Antibody Responses in a Patient with Multiple Sclerosis Symptoms in multiple sclerosis are episodic in nature. At certain times, a patient with MS may be in remission (reduced or no symptoms), and at other times, symptoms may recur. The reasons for the episodic nature of symptoms in MS are poorly understood. One hypothesis is that memory B-cells may play a role. According to an hypothesis, during recurrent MS, CNS B-cells respond by producing antibodies directed at CNS antigens (e.g., myelin proteins), which trigger symptoms. When symptoms resolve, the patient is in remission. Prior to this invention the mechanism of recurrence was poorly understood. We have found that B-cells capable of producing antibodies against CNS antigens may reside for relatively long periods of time in lymphoid or other tissues outside the CNS, in a relatively quiescent state. Recurrence of symptoms may be associated with reactivation of such quiescent B cells, termed "Memory B-Cells."

To evaluate this hypothesis, we devised an ELISPOT test for memory B-cells (the "Indirect B-Cell assay" or "Memory B-Cell assay") described below in Examples 21 and 22. We herein report a new assay to detect memory B-cells that may be responsible for recurrence of symptoms in MS.

To do this, we retrieved PBMCs from MS patients in remission. After isolating the PBMCs, we cultured them in cell culture wells as described herein above. We then exposed the PBMCs to medium or a stimulating agent (polyclonal stimulation), and determined the presence of antibodies against human MOG (hMOG).

FIG. 16 depicts photographs of cell culture wells with cells therein to show myelin (hMOG)-specific B-cells in MS patients (top two images) and control subjects (bottom images) using an Indirect B-Cell assay of this invention. Polyclonal activation of PBMCs isolated from the blood induced hMOG-specific antibody secretion in the polyclonally stimulated B-cells contained in the PBMC sample. We determined the presence of anti-hMOG antibodies using methods described herein below in Examples 21 and 22. We found that hMOG-specific B-cells were present in MS patients (FIG. 16 top right photograph), but not in healthy controls (FIG. 16 bottom right photograph). In wells treated with medium alone (FIG. 16 top and bottom left photographs), no activated B-cells were observed. This reaction is antigen-specific and does not occur in the absence of antigen (FIG. 16 left images).

In another study, we used human brain lysate to stimulate B-cell responses. Results of this study are shown in FIG. 17.

FIG. 17 depicts photographs of cell culture wells having cells from either a patient with MS (FIG. 17 top photographs) or a subject not having MS (FIG. 17, bottom photographs). In each well, responses of whole human brain lysate-specific B-cells was observed. Polyclonal activation (by R848, IL-2 and β-mercaptoethanol) of PBMCs isolated from the blood induced CNS-specific antibody secretion in the polyclonally stimulated B-cells contained in the PBMC. CNS lysate-specific B-cells were present in a patient having MS (FIG. 17 top right photograph), but not in a healthy control subject (FIG. 17 bottom right photograph). This reaction is antigen-specific and does not occur in the absence of antigen (medium controls (FIG. 17 left top and left bottom photographs).

We conclude from these studies that in MS patients with no symptoms, that memory B-cells are present in MS patients and can be activated by stimulation.

Example 21: Antigen-Specific B-Cell Test

In some embodiments of this invention, an antigen-specific B-cell test can be used. FIG. 18A depicts a diagram 1800 of such an assay. A cell culture well has membrane 1804 on which antigens 1808 are attached. Antigen-specific immunoglobulins 1812 produced by B-cells are depicted as binding to antigens 1808. Then a secondary biotinylated, anti-human immunoglobulin antibody 1816 directed against antigen-specific immunoglobulin 1812 and is shown binding thereto. An enzyme, horseradish peroxidase 1820 is attached to the anti-human immunoglobulin antibody 1816. A substrate specific for the enzyme 1820 is then added to the cell culture well, and action of enzyme 1820 produces a colored reaction product, which can be detected visually.

FIG. 18B depicts an alternative embodiment 1802 of this invention for B-cell tests of undefined specificity. Membrane 1804 and antigen 1808 are shown as in FIG. 18A. Immunoglobulins with undefined specificity produced by B-Cells 1828 are depicted not being attached to antigen 1808. Non-specific antibodies do not bind to the coating antigen and are washed off.

Example 22: Direct B-Cell Assay

In certain embodiments of this invention, a "Direct B-Cell assay" can be used to detect the presence of B-cells capable of producing antibodies against CNS-specific antigens.

FIGS. 19A and 19B depict summaries of Direct B-Cell (FIG. 19A) assays and Indirect B-Cell assays (FIG. 19B) of this invention. FIG. 19A depicts a "Direct B-Cell assay" 1900 of this invention showing a CNS Plasma Cell 1904 that produces CNS-antigen specific antibodies 1906. CNS Plasma Cell 1904 moves into the bloodstream (at arrow 1907), and is labeled as Plasma Cell 1908, which is depicted producing CNS-antigen specific antibodies 1906. Plasma Cell 1908 is then obtained from a sample of peripheral blood mononuclear cells (PBMCs) and placed in a culture well (at arrow 1910). CNS-antigen specific antibodies 1906 are then detected using ELISPOT or similar methods, and show image 1912 having spots indicative of cells that produce CNS-antigen specific antibodies.

FIG. 19B depicts an "Indirect B-Cell assay" or "Memory B-Cell assay" 1902 of this invention. Memory B-Cell 1916 is depicted within stroma 1918, and is depicted not producing antibodies. Memory B-Cell 1916 was once in the CNS, where it was responsive to a CNS-specific antigen (not shown; see FIG. 19A). However, Memory B-Cell 1916 migrated into the bloodstream, and became lodged in a B-cell repository in the spleen, lymph node or other site in the body. Memory B-Cell 1916 is then released into the bloodstream at arrow 1922. Memory B-Cell 1916 is then drawn along with a sample of PBMCs, which are placed in a culture well. Then, polyclonal stimulation of Memory B-Cell 1916 is accomplished by exposure of the cells to IL-2, R-848, and 2-mercaptoethanol (2-ME or β-ME). Memory B-Cell 1916 is thus stimulated and becomes Plasma Cell 1924, which produces antibodies 1928. CNS-antigen specific antibodies 1928 are then detected using ELISPOT or similar methods, and show image 1936 having spots indicative of cells that produce CNS-antigen specific antibodies 1928.

Example 23: Myelin-Specific B-Cell Responses in Patients with MS, CIS, and Healthy Subjects I To study the prevalence of myelin-specific B-cell responses in human beings, we carried out a preliminary study of 21 healthy subjects without MS, 10 patients with MS, and 3 patients having Clinically Isolated Syndrome (CIS). Results of this preliminary study are shown below in Table 3.

TABLE 3

Prevalence of Myelin-Specific B Cells

| Subject Category | Number of Patients Exhibiting a Myelin-Specific B-Cell Response |
|---|---|
| Healthy | 0/21 |
| Multiple Sclerosis (MS) | 10/10 |
| Clinically Isolated Syndrome (CIS) | 1/3 |
| Unresponsive to Immune Modulatory Treatment | 0/1 |

We conclude from this preliminary study that myelin-specific B-cell responses are completely absent in the control subjects, are prevalent in all 10 patients with MS, and occur (1 out of 3) in the patients with CIS.

Example 24: Direct B-Cell Test and Indirect B-Cell Test in Healthy Subjects without MS II To be able to determine the usefulness of the Direct B-Cell test and the Indirect B-Cell test of this invention, we first studied a series of healthy human subjects without MS. We assessed: (1) disease stage, (2) disease activity, (3) serum antibodies, (4) Th-1 cells ($T_H1$), Th-17 cells ($T_H17$), (5) Direct B-Cell test data, and (6) Indirect B-Cell test data. Results are shown below in FIGS. 20A and 20B.

The cut-off values for the myelin-specific serum antibody titers and the $T_H1$ and $T_H17$ response have been calculated by testing a total of 71 healthy controls. These cut-off values are highlighted in grey and have been calculated according to the formula [mean value±2*standard deviation]. None of the healthy controls tested showed a positive response in either the Direct or Indirect B cell test. Any positive responses in the Direct or Indirect B-Cell tests observed in the MS patients or in patients at risk of developing MS are therefore indicative of the disease.

The inclusion criteria for healthy controls were an age over 18, female or male gender, informed consent, and no previous history of neuroimmunological or autoimmune disorders. The exclusion criteria were the intake of cytokine or anti-cytokine drugs, intravenous immunoglobulins, plasmapheresis or the intake of non-approved drugs 12 months prior to inclusion in the study. In addition, severe systemic or psychiatric disorders were considered as exclusion criteria.

As can be seen from FIGS. 20A and 20B, the serum antibodies were not statistically significantly different from zero (0.42±0.26), with a cut-off of 0.94. Similarly, $T_H1$ cells were not significantly different from zero (3.33±4.22) with a cut-off of 11.77. $T_H17$ cells also were not significantly different from zero (0.91±1.35) with a cut-off of 3.60. Finally, the Direct B-Cell test and the indirect B-Cell test were either negative (1) or not determined (n.d.) for this group of subjects without MS. Thus, the thresholds for concluding the presence of MS for (1) serum antibodies, (2) $T_H1$ cells, (3) $T_H17$ cells, (4) Direct B-Cell test and (5) indirect B-Cell test are: (1) greater than 0.96, (2) >11.77, (3) >3.60, (4) >0.0, and (5) >0.0, respectively. Thus, patients having values greater than these thresholds are concluded to have MS, even if asymptomatic.

Example 25: Clinically-Isolated Syndrome (CIS)

We then studied a series of 12 patients with CIS and measured: (1) disease stage, (2) disease activity, (3) serum antibodies, (4) $T_H1$ cells, (5) $T_H17$ cells, (6) Direct B-Cell test, and (7) Indirect B-Cell test. Results are shown below in FIG. 21.

The cut-off values for a positive response were calculated as mean values±2 SD of a total of 71 healthy controls tested. Positive test results are highlighted in grey. As can be seen in FIG. 21, of 12 patients with CIS, 10 were positive in at least one of the criteria above. In particular, 5 patients had elevated serum CNS-specific antibodies and 3 had elevated $T_H17$ cells. One patient had both elevated serum antibodies and elevated $T_H17$ cells. One other patient had a positive Direct B-Cell test and active MS, and three additional patients had a positive Indirect B-Cell test (with non-active MS). Two of the patients with elevated $T_H17$ cells also had positive Indirect B-Cell test results.

Summary of Results and Conclusions 10 of 12 patients tested showed at least one positive test response. For one of the non-responders it has been shown that this donor suffers from cervical myelitis rather than MS (BII121111). Donor SII250212 presented with NMO only, the MRI revealed rather unspecific lesions, not typical of MS. Thus, 10 of 10 patients with CIS exhibited at least one of a positive serum antibody test, a positive TH17 test or a positive Indirect B-Cell test.

Repeated testing proved to be important. Some of the CIS patients were negative upon initial testing, but converted with time (repeated testing after 3 months). This corresponds to the idea that at this early stage of the disease the initial wave of autoimmune responses that caused the clinical symptoms had ceased and only with time the second and full-blown response develops.

The initial immune response showed inter-individual heterogeneity being characterized by T-cell or B-cell immunity or a combination of both. We conclude that diagnosis of CIS is highly accurate, with no false negative results.

Example 26: Patients with Remitting Relapsing MS

In a series of 11 patients with clinically definite MS, we determined: (1) disease stage, (2) disease activity, (3) serum antibodies, (4) $T_H1$ cells, (5) $T_H17$ cells, (6) direct B-Cell test, and (7) Indirect B-Cell test. Results are shown in FIG. 22.

FIG. 22 is a table showing that for all 11 patients with remitting/relapsing MS (RRMS), every one had at least one positive criterion for MS. Although two of the patients had elevated levels of serum CNS-specific antibodies, and one patient had elevated levels of $T_H1$ and $T_H17$ cells, 10 of the patients with RRMS had a positive Indirect B-Cell test and the other had an elevated Direct B-Cell test. Interestingly for the one patient in this group that had active MS at the time, the only abnormal finding was an elevated Direct B-Cell test. All of the other patients in this group (n=10) were in remission (non-active disease), yet had positive Indirect B-Cell test results, demonstrating the presence of Memory B-cells. This striking finding was completely unexpected based on current knowledge of MS patients in remission.

Results and Conclusions

The cut-off values for a positive response were calculated as mean values±2 SD of a total of 71 healthy controls tested. Positive test results are highlighted in grey.

All eleven patients show positive test results Definite MS is characterized by the presence of a memory B-cell response. We conclude that diagnosis of RRMS using methods of this invention is highly accurate, showing no false negative results. Thus, these patients can benefit from immune modulatory therapy to decrease B-cells.

Example 27: Patients with Clinically Definite MS with Secondary Progressive or Chronic Disease In 12 patients with MS and secondary progressive or chronic disease, we determined: (1) disease stage, (2) disease activity, (3) serum antibodies, (4) $T_H1$ cells, (5) $T_H17$ cells, (6) Direct B-Cell test, and (7) Indirect B-Cell test. Results are shown below in FIG. 23.

In 12 patients with chronic non-active MS, one had elevated serum CNS-specific antibodies, and one had elevated $T_H1$ cells. All 12 patients had negative Direct B-Cell test results, and 5 of 12 patients had positive Indirect B-Cell test results.

The cut-off values for a positive response were calculated as mean values±2 SD of a total of 71 healthy subjects. Positive test results are highlighted in grey.

Primary Progressive MS (PPMS) is characterized by a gradual progression of the disease from its onset with no superimposed relapses and remissions. There may be periods of a leveling off of disease activity. PPMS differs from RRMS and SPMS in that the onset is typically in the late thirties or early forties, men are as likely women to develop it and initial disease activity is often in the spinal cord and not in the brain. Primary Progressive MS often migrates into the brain, but is less likely to damage brain areas compared to RRMS and SPMS. For example, people with PPMS are less likely to develop cognitive deficits. PPMS is the subtype of MS that is least likely to show inflammatory (gadolinium enhancing) lesions on MRI scans. The primary progressive form of the disease affects between 10 and 15% of all people with multiple sclerosis.

Results and Conclusions

Clinical progression into chronic MS is characterized by an attenuation of the autoimmune component of the disease in favor of primary neurodegeneration. The tests of this invention correctly identified 7 of 12 patients with CDMS, and 5 patients showed false negative results.

The test identifies those patients with SP-MS/chronic MS that will still benefit from immune modulatory treatment in the chronic stage of the disease. In particular, those patients with positive Indirect B-Cell test results or elevated serum CNS-specific antibodies can be beneficially treated with immune modulatory treatments. For patients with a negative Indirect B-Cell test, a negative serum antibody test, and a negative $T_H1/T_H17$ test, immune modulatory therapy may not be indicated, whereas use of anti-neurodegenerative therapies are indicated.

Example 28: The Triple Test for Diagnosis and Prediction of MS

Introduction

This Example describes an embodiment of this invention in which three immunological tests are made that provides improved ability to diagnose and predict prognosis in patients with MS. The three tests measure: (1) CNS-specific antibodies (e.g., against MP4 or whole human brain lysate), (2) CNS-specific $T_H1$ and $T_H17$ cells using ELISPOT methods (e.g., antigens MP4, hMOG, whole human brain lysate), and (3) CNS-specific B-cells using ELISPOT (e.g., antigens MP4, hMOG, whole human brain lysate).

ELISA Methods

1. Cell culture wells are coated with antigen (MP4 or whole human CNS lysate).
2. Plates are blocked with 10 fetal bovine serum to prevent non-specific binding.
3. Serum dilutions 1:40 in 10% fetal bovine serum.
4. Plates are developed with TMB, stopped after 2 minutes with $H_2SO_4$ and optical density (OD) is read at 450 nm.
5. Cut-off value for a positive ELISA response is considered to be OD>MW+2 SD of the healthy controls tested.

ELISPOT Methods for Measurement of $T_H1$ and $T_H17$ Cells

1. ELISPOT methods are carried out using standard methods.
2. The protocol is modified to provide an incubation time of 72 hours.
3. $3\times10^5$ PBMCs are plated per well (e.g., of a 96 well plate).
4. The number of spots is counted per well.
5. Cut-off value for a positive $T_H1$ response is the spot number>MW+2 SD of the healthy control subjects tested.
6. Cut-off value for a positive $T_H17$ response is the spot number>MW+2 SD of the healthy controls tested.

ELISPOT Methods for Measurement of B-Cells

1. Cell culture wells are coated with antigen (e.g., MP4, hMOG or whole human brain lysate).
2. $10^6$ PBMCs are plated per well.
3. Direct measurements of IgG and IgM before and after:
4. Polyclonal stimulation with R-848, IL-2 and β-mercaptoethanol for 72 hours.
5. Positive response is considered by presence of plasma cells or B-cells secreting MP4 and/or hMOG and/or whole human CNS lysate-specific antibodies.
6. Cut-off value for a positive B cell response is the spot number>MW+2 SD of the healthy controls tested.

Study Populations 1. 71 healthy subjects without MS were studied for determination of baseline data;
2. 12 patients with clinically isolated syndrome (CIS);
3. 11 patients with relapsing remitting MS (RRMS); and
4. 12 patients with SP-MS secondary progressive MS (SP-MS)/incomplete remissions/chronic MS.

Advantages

Based on the Examples above, the Triple Test provides a highly sensitive and specific method for diagnosing MS combining detection of autoimmune T-cells, B-cells, and serum antibodies against CNS antigens. Further, the Triple Test facilitates identification of subpopulations of patients depending on the T-cell, B-cell and antibody response patterns. The Triple Test facilitates development of therapeutic strategies differentially targeting T-cells and B-cells. The Test also can identify patients in whom a B-cell- or T-cell-specific strategy will not be successful, thereby eliminating the costs and hazards associated with ineffective therapeutic interventions. The Triple Test reveals disease-specific kinetics of autoimmune responses and demonstrates that myelin-specific autoimmune responses increasingly develop as patients progress from a CIS/RIS state to definite, fully blown MS while decreasing when patients enter the SP-MS/chronic MS stage. The Tests of this invention permit the identification of optimal therapeutic windows for immune modulatory treatment. Finally, the Triple Test has demonstrated the diagnostic value of B-cell measurements, in addition to T-cell measurements.

Example 29: CNS Antigen-Specific T-Cell and B-Cell/Antibody Responses as Predictors for the Treatment of Multiple Sclerosis Multiple sclerosis is a chronic autoimmune disease of the central nervous system. The etiology and pathogenesis of the disease remain unclear, but based on the disclosures herein, myelin-reactive T-cells and B-cells/antibodies play a crucial role. In addition, environmental factors, including infectious agents, are suggested to facilitate the invasion of auto-reactive immune cells into the CNS by crossing the blood-brain barrier (BBB). The transmigration of cells and soluble molecules such as antibodies through the BBB requires several steps including the breakdown of the barrier by proteases and the activation of the endothelial cells that form the barrier. Having entered the CNS, auto-reactive T-cells recognize self-antigen and start producing cytokines. The nature of the cytokines secreted (pro- or anti-inflammatory) depends on the interaction between the T-cells and antigen-presenting cells and other interacting molecules. In addition, B-cells get activated, differentiate into plasma cells and start secreting autoantibodies. Finally, also cells from the innate immune system are drawn into the inflammatory reaction. Acute inflammatory, demyelinating plaques occur due to the binding of autoantibodies to myelin, activation of the complement system and phagocytosis of myelin by macrophages. Also, cytotoxic T-cells and pro-inflammatory cytokines can directly damage CNS tissue.

The treatment options for MS aim at targeting this autoimmune component of the disease. Acute relapses are commonly treated with a short duration of high-dose oral or intravenous corticosteroids. Typically, treatment with high-dose corticosteroids is only initiated when a patient presents with an acute clinical event, a relapse. The problem with each new clinical event is that there is the possibility that irreversible CNS damage and with that irreversible functional deficits/symptoms will occur in a patient. However, thus far there is no diagnostic-prognostic test that can reliably predict whether and when a relapse is likely to occur. Measurements of the CNS antigen-/myelin-specific T-cell and/or B-cell/antibody response are suitable to predict an upcoming relapse before clinical symptoms have developed in a given patient. This has important therapeutic implications for the patient. According to our claim, the detection of an increased CNS antigen-/myelin-T-cell and/or B-cell/antibody response precedes the development of a disease relapse. The early initiation of treatment before the onset of (new) clinical symptoms is likely to prevent the development of the upcoming relapse, thus also preventing the development of irreversible CNS damage. Early treatment, according to the currently accepted regimen, can include corticosteroids, but also other treatment options, such as disease-modifying drugs, that prove to be effective in the prevention of relapses.

Besides acute treatment with corticosteroids, disease-modifying/immune modulatory drugs are available, that are designed to prevent relapses and progression of disability rather than treat specific symptoms or exacerbations of the disease. These agents modify the immune response through various immunomodulatory or immunosuppressive effects. The currently approved disease-modifying drugs include glatiramer acetate, interferon beta-1a, mitoxantrone, tysabri and fingolimod. The indication and mechanisms of action of each drug are summarized in Table 4.

TABLE 4

Current MS Therapies

| Drug | Indication | Patients targeted |
| --- | --- | --- |
| Glatiramer Acetate Copaxone ® | Reduce frequency of relapses in patients with RRMS including patients who experienced a first clinical episode and have MRI features consistent with MS. | CIS, RRMS |
| Interferon beta-1a Avonex ®, Avonex PS | Treatment of patients with relapsing forms of MS to slow accumulation of physical disability and decrease the frequency of clinical exacerbations. Effective in patients who experienced a first clinical episode and have MRI features consistent with MS. | CIS, RRMS, SPMS |
| Interferon beta-1a Rebif ® | Treatment of relapsing forms of MS to decrease the frequency of clinical exacerbations and delay the accumulation of physical disability. | See above |
| Inteferon beta-1b Betaseron ® | Treatment of relapsing forms of MS to reduce the frequency of clinical exacerbations. Effective in patients who experienced a first clinical episode and have MRI features consistent with MS. | See above |
| Interferon beta-1b Extavia ® | Treatment of relapsing forms of MS to reduce the frequency of clinical exacerbations. Effective in patients who experienced a first clinical episode and have MRI features consistent with MS. | See above |
| Mitoxantrone (Novantrone ® Ralenova ®) cyclophosphamide (Endoxan ®), azathioprine (Imurek ®) | Reduce neurologic disability and/or the frequency of clinical relapses in SPMS, PPMS or worsening RRMS. | RRMS, SPMS, PPMS |

TABLE 4-continued

Current MS Therapies

| Drug | Indication | Patients targeted |
| --- | --- | --- |
| Natalizumab Tysabri ® | Treatment of relapsing forms of MS to delay the accumulation of physical disability and reduce the frequency of clinical exacerabations. | CIS, RRMS |
| FTY720 Fingolimod Gilenya ® and BAF312 | Treatment of relapsing forms of MS in order to reduce the frequency of clinical exacerbations and to delay the progression of disability. | CIS, RRMS |
| Immunoglobulins (IVIGs) Gamunex ® Octagam ® | IVIG is used in MS to slow progression of disease, reduce the number of and limit disability and MS symptoms | CIS, RMA, SPMS, PPMS |
| B Cell-specific therapies: Rituximab, ocrelizumab, ofatimumab, belimumab atacicept, epratuzumab | Treatment of B cell dependent MS; reduce frequency of clinical exacerbations and delay progression of disability. Depletes CD20 or CD22' lymphocytes or block interaction of cell survival and growth factors with their receptors on B cells. | CIS, RRMS, SPMS, potentially PPMS |
| MLN1202 | Treatment of relapsing forms of MS to delay accumulation of physical disability and reduce frequency of clinical exacerbations. Inhibits nerve fiber degeneration (demyelination, axonal degeneration and neuronal damage by inhibiting apoptosis, glutamate toxicity and increase in trophic factors. | CIS, RRMS, SPM < potentiall PPMS |
| GABAA receptor antagonists Trophic factors including CNTF, IGF-1, VEGF, GDNF, FGF, Anti-protein aggregation agents, Calcium antagonists Minocycline, Acamprosate Creatine, nimodipine | Reduce neurological disability and/or frequency of clinical relapses in SPMS, PPMS and RRMS. | CIS, RRMS, SPMS PPMS |
| CGP77116 | Treatment of relapsing form of MS to delay accumulation of physical disability and reduce frequency of clinical exacerbations. Altered peptide ligand/mimetope for a dominant antigenic determinant of MBP (83-99). Decreases MBP-specific response by competing with native MBP. | CIS, RRMS, SPMS, potentially PPMS |
| Vitamin D3 | Treatment of B cell dependent MS, reduces frequency of clinical exacerbations and delay progression of disability. Vitamin D reduces B cell proliferative responses, reduces antibody secretion and class switching, inhibits maturation into memory and plasma phenotypes and induces apoptosis, but does not modulate expression of HLA-DR or co-receptors. | CIS, RRMS, SPMS, PPMS |
| Neuroprotective agents (anti-apoptotic) caspase inhibitors antioxidants, glutamate toxicity blocking agents, glutamate receptor antagonists, NMDA receptor antagonists | Reduce neurological disability and/or frequency of clinical relapses in SPM, PPMS and RMS. Inhibits nerve fiber degeneration (demyelination, axonal damage) and neuronal damage. | CIS, RRMS, SPMS, PPMS |

The majority of patients with MS are typically on immune modulatory treatment. However, it should be noted that not every patient responds to immune modulatory treatment and response rates can differ significantly and also decline over time in different patient populations. Also, serious side effects can occur.

Embodiments of this invention for diagnostic and/or prognostic tests for MS can facilitate the development of more efficient treatment strategies that also lead to higher patient compliance. In fact, in some cases, it can be an effective strategy to initiate immune modulatory treatment only when an increased CNS antigen-specific T-cell and/or B-cell antibody response is evident, Our invention enables this approach. Previous to this disclosure, there has been no means of measuring or predicting the responsiveness of individual patients to immune modulatory treatment. By measuring the magnitude of the CNS antigen- or myelin-specific T-cell and/or B-cell antibody responses, such a prediction can be clinically useful. In simple terms, immune modulatory treatment means that the auto-reactive immune response in a patient is modulated in a way that makes it less likely that self-tissue is targeted and destroyed. The autoimmune component of the disease may be more or less relevant to the actual disease pathogenesis in individual patients and patients have been described to show CNS histopathology that is more dominated by primary oligodendrocyte loss, for example. In such patients, immune modulatory treatment due to its very nature is less likely to be effective compared to patients with a prevalent T-cell responses or B-cell antibody responses contributing to the disease. Our methods can therefore distinguish different patient populations based on their predicted responsiveness to treatment. By detecting patients, in whom a CNS-/myelin-reactive pathology is not prevalent, as shown by a decreased/absent responsiveness to immune modulatory treatment, our approach enables better treatment of "low- or non-responder" patients.

Finally, opinions about the treatment strategy for patients with clinically isolated syndrome (CIS) or radiologically isolated syndrome (RIS) differ. While patients are treated with corticosteroids during the acute disease, it is unclear whether these patients will show long-term benefit from an early initiation of immune modulatory treatment. A significant problem here is that currently there is no diagnostic and/or prognostic test that defines whether a patient with CIS or RIS will eventually develop MS. Therefore, most patients do not see any reason why they should start treatment without even knowing whether they will finally develop MS. Even if the initial brain MRI is abnormal (with a demyelinating lesion), the likelihood of developing MS is only 60 percent. If the initial brain MRI is normal (no demyelinating lesion), there is still a likelihood of 20 percent of developing MS. By measuring whether a CNS antigen- or myelin-specific T-cells and/or B-cell antibody responses are present in a patient with CIS or RIS, embodiments of this invention allow one to distinguish patients that will develop MS from those patients that are not likely to develop MS. Thus, methods of this invention can have important therapeutic implications because CIS or RIS patients with a positive response in our test can greatly benefit from early initiation of immune modulatory treatment, including use of anti-CD20, CD21, CD22, and other B-cell modulatory agents, while patients with a negative response are not likely to benefit from such therapies.

Example 30: Preparation of Purified Detection Particles Labeled with Streptavidin and Biotinylated Detection Antibodies In some embodiments, this a bead array method includes use of detection particles having detection reagents thereon. An embodiment of this method is illustrated in FIG. 24. A nanoparticle 2404 labeled with streptavidin 2405 is mixed with biotinylated detection reagent 2408 comprising biotin 2409 coupled to a detection reagent 2410. These are incubated together for sufficient time to permit biotin 2409 of biotinylated detection reagent 2408 to bind streptavidin 2405 on the nanoparticle 2404 thereby forming biotinylated streptavidin detection particle complex 2411. Some free biotinylated detection reagent 2408 is depicted free in solution. Then, an agarose particle 2414 having streptavidin 2405 thereon is added to the mixture and incubated for a further period of time. The resulting solution contains complexes 2411 and agarose/biotinylated detection reagent complexes 2418. Little or no free biotinylated detection reagent 2408 is present in the solution. Next, centrifugation step 2420 results in sedimentation of agarose/biotinylated detection reagent complexes at 2424, leaving biotinylated streptavidin detection particle complexes 2411 free in solution. Subsequently, complexes 2411 can be used in detection particle, bead array-based assays.

Example 31: Two Color Assay for Human IL2 and Human Interferon γ

On day 1 plates (MIP45, Millipore) were coated simultaneously with two primary capture monoclonal antibodies (mAbs), one raised against (1) h-IFN-γ Endogen MA700A) at a concentration of 4 µg/ml and another raised against h-IL-2 (R&D Systems 5334.21) at a concentration of 3 µg/ml. 200 µl of coating mAbs mixture was added per well. Plates were coated overnight at 4° C.

On day 2 the plates were washed 3 times with PBS (200 µl/well), and blocked with 1% BSA in PBS for 2 h at RT (200 µl/well). PPD antigen was added to the well at concentration 100 µg/ml (100 µl/well). 300.000 human unseparated PBMCs were added to the same wells (100 µl/well). Plates were incubated for 24 h at 37° C., humidified, in the presence of 7% $CO_2$.

On day 3 cells and unbound materials were removed from the wells by washing 3 times with PBS and 3 times with PBS-Tween (0.05%). Then plate was incubated overnight at 4° C. with 100 µl per well of detection particles directly labeled with secondary detection reagents being antibodies. Red dots (655 nm) were labeled with anti h-IFN-γ Endogen M701) and used at a concentration $5.0 \times 10^{-9}$ M. Green dots (525 nm) were labeled with h-IL-2 mAbs (Endogen BG5) and used at a concentration of $1.0 \times 10^{-8}$ M.

On day 4 unbound detection particles were washed out 4 times with PBS-Tween (0.05%) and 3 times with PBS. Digital images were taken using a Fluorescent microscope (Optem) with a longpath emission filter (Chroma 32013).

A photomicrograph FIG. 25 of a well treated as above shows red dots (R) that indicate the presence of secreted h-IFN-γ. Green dots (G) indicate the presence of secreted h-IL-2.

REFERENCES

Each of the patents, patent applications and non-patent documents disclosed herein are incorporated in their entirety, as if separately so incorporated.

J. Goverman, T. Brabb, Rodent models of experimental allergic encephalomyelitis applied to the study of multiple sclerosis, Lab. Anim Sci. 46 (1996) 482-492.

M. Sospedra, R. Martin, Immunology of multiple sclerosis, Annu. Rev. Immunol. 23 (2005) 683-747.

L. Steinman, S. S Zamvil, How to successfully apply animal studies in experimental allergic encephalomyelitis to research on multiple sclerosis, Ann. Neurol. 60 (2006) 12-21.

R. Gold, C. Linington, H. Lassmann, Understanding pathogenesis and therapy of multiple sclerosis via animal models: 70 years of merits and culprits in experimental autoimmune encephalomyelitis research, Brain 129 (2006) 1953-1971.

V. K. Tuohy, Z. Lu, R. A. Sobel, R. A. Laursen, M. B. Lees, Identification of an encephalitogenic determinant of myelin proteolipid protein for SJL mice, J. Immunol. 142 (1989) 1523-1527.

R. A. Sobel, V. K. Tuohy, Z. J. Lu, R. A. Laursen, M. B. Lees, Acute experimental allergic encephalomyelitis in SJL/J mice induced by a synthetic peptide of myelin proteolipid protein, J. Neuropathol. Exp. Neurol. 49 (1990) 468-479.

I. Mendel, N. K. de Rosbo, A. Ben Nun, A myelin oligodendrocyte glycoprotein peptide induces typical chronic experimental autoimmune encephalomyelitis in H-2b mice: fine specificity and T cell receptor V beta expression of encephalitogenic T cells, Eur. J. Immunol. 25 (1995) 1951-1959.

I. Mendel, N. K. de Rosbo, A. Ben Nun, Delineation of the minimal encephalitogenic epitope within the immunodominant region of myelin oligodendrocyte glycoprotein: diverse V beta usage by T cells recognizing the core epitope encephalitogenic for T cell receptor V beta b and T cell receptor V beta in H-2b mice, Eur. J. Immunol. 26 (1996) 2470-2479.

N. T. Potter, T. S. Stephens, Humoral immune recognition of proteolipid protein (PLP)-specific epitopes in the SJL/J mouse, J. Neurosci. Res. 37 (1994) 15-22.

B. L. McRae, S. D. Miller, Fine specificity of CD4+ T cell responses to the dominant encephalitogenic PLP 139-151 peptide in SJL/J mice, Neurochem. Res. 19 (1994) 997-1004.

P. Hjelmstrom, A. E. Juedes, J. Fjell, N. H. Ruddle, B-cell deficient mice develop experimental autoimmune encephalomyelitis with demyelination after myelin oligodendrocyte glycoprotein sensitization, J. Immunol.161 (1998) 4480-4483.

A. R. Oliver, G. M. Lyon, N. H. Ruddle, Rat and human myelin oligodendrocyte glycoproteins induce experimental autoimmune encephalomyelitis by different mechanisms in C57BL/6 mice, J. Immunol. 171 (2003) 462-468.

J. E. Merrill, D. H. Kono, J. Clayton, D. G. Ando, D. R. Hinton, F. M. Hofman, Inflammatory leukocytes and cytokines in the peptide-induced disease of experimental allergic encephalomyelitis in SJL and B10.PL mice, Proc. Natl. Acad. Sci. USA 89 (1992) 574-578.

V. Navikas, H. Link, Review: Cytokines and the pathogenesis of multiple sclerosis, J. Neurosci. Res. 45 (1996) 322-333.

H. H. Hofstetter, A. Y. Karulin, T. G. Forsthuber, P. A. Ott, M. Tary-Lehmann, P. V. Lehmann, The cytokine signature of MOG-specific CD4 cells in the EAE of C57BL/6 mice, J. Neuroimmunol. 170 (2005) 105-114.

H. H. Hofstetter, T. G. Forsthuber, Kinetics of IL-17- and interferon-gamma producing PLPp-specific CD4 T cells in EAE induced by coinjection of PLP/IFA with pertussis toxin in SJL mice, Neurosci. Lett. 476 (2010) 150-155.

H. H. Hofstetter, S. M. Ibrahim, D. Koczan, N. Kruse, A. Weishaupt, K. V. Toyka, R. Gold, Therapeutic efficacy of IL-17 neutralization in murine experimental autoimmune encephalomyelitis, Cell. Immunol. 237 (2005) 123-130.

I. I. Ivanov, B. S. McKenzie, L. Zhou, C. E. Tadokoro, A. Lepelley, J. J. Lafaille, D. J. Cua, D. R. Littman, The orphan nuclear receptor RORgammat directs the differentiation program of proinflammatory IL-17+ T helper cells, Cell 126 (2006) 1121-33.

Y. Komiyama, S. Nakae, T. Matsuki, A. Nambu, H. Ishigame, S. Kakuta, K. Sudo, Y. Iwakura, IL-17 plays an important role in the development of experimental autoimmune encephalomyelitis. J. Immunol. 177 (2006) 566-73.

H. H. Hofstetter, O. S. Targoni, A. Y. Karulin, T. G. Forsthuber, M. Tary-Lehmann, P. V. Lehmann, Does the frequency and the avidity spectrum of the neuroantigen-specific T cells in the blood mirror the autoimmune process in the central nervous system of mice undergoing experimental allergic encephalomyelitis?, J. Immunol. 174 (2005) 4598-4605.

S. Kuerten, D. A. Kostova-Bales, L. P. Frenzel, J. T. Tigno, M. Tary-Lehmann, D. N. Angelov, P. V. Lehmann, MP4- and MOG:35-55-induced EAE in C57BL/6 mice differentially targets brain, spinal cord and cerebellum, J. Neuroimmunol. 189 (2007) 31-40.

D. J. Mahad, J. Lawry, S. J. L. Howell, M. N. Woodroofe, Longitudinal study of chemokine receptor expression on peripheral lymphocytes in multiple sclerosis: CXCR3 upregulation is associated with relapse, Mult. Scler. 9 (2003) 189-198.

B. Bielekova, R. Martin, Development of biomarkers in multiple sclerosis. Brain 127 (2004) 1463-1478.

L. Rinaldi, P. Gallo, Immunological markers in multiple sclerosis: tackling the missing elements, Neurol. Sci. 26 (2005) S215-S217.

M. Reindl, M. Khalil, T. Berger, Antibodies as biological markers for pathophysiological processes in multiple sclerosis, J. Neuroimmunol. 180 (2006) 50-62.

A. Lutterotti, T. Berger, M. Reindl, Biological markers for multiple sclerosis. Curr. Med. Chem. 14 (2007) 1956-1965.

R. J. Fox, P. Kivisakk, E. Fisher, B. Tucky, J. C. Lee, R. A. Rudick, R. M. Ransohoff, Multiple sclerosis: chemokine receptor expression on circulating lymphocytes in correlation with radiographic measures of tissue injury. Mult. Scler. 14 (2008) 1036-1043.

J. Drulovic, E. Savic, T. Pekmezovic, S. Mesaros, N. Stosjavljevic, I. Dujmovic-Basuroski, I., J. Kostic, V. Vasic, M. Mostarica Stojkovic, D. Popadic, Expression of $T_H1$ and $T_H17$ cytokines and transcription factors in multiple sclerosis patients: Does baseline T-Bet mRNA predict the response to interferon-beta treatment?, J. Neuroimmunol. 215 (2009) 90-95.

S. Sawai, H. Umemura, M. Mori, M. Satoh, S. Hayakawa, Y. Kodera, T. Tomonaga, S. Kuwabara, F. Nomura, Serum levels of complement C4 fragments correlate with disease activity in multiple sclerosis: Proteomic analysis, J. Neuroimmunol. 218 (2010) 112-115.

C. M. Pelfrey, R. A. Rudick, A. C. Cotleur, J. C. Lee, M. Tary-Lehmann, P. V. Lehmann, Quantification of self-recognition in multiple sclerosis by single-cell analysis of cytokine production, J. Immunol. 165 (2000) 1641-1651.

R. Hohlfeld, H. Wekerle, Autoimmune concepts of multiple sclerosis as a basis for selective immunotherapy: from pipe dreams to (therapeutic) pipelines, Proc. Natl. Acad. Sci. USA 101 (2004) 14599-14606.

P. V. Lehmann, T. Forsthuber, A. Miller, E. E. Sercarz, Spreading of T-cell autoimmunity to cryptic determinants of an autoantigen. Nature 358 (1992) 155-157.

B. L. McRae, C. L. Vanderlugt, M. C. Dal Canto, S. D. Miller, Functional evidence for epitope spreading in the relapsing pathology of experimental autoimmune encephalomyelitis, J. Exp. Med. 182 (1995) 75-85.

C. L. Vanderlugt, W. S. Begolka, K. L. Neville, Y. Katz-Lewy, L. M. Howard, T. N. Eagar, J. A. Bluestone, S. D. Miller, The functional significance of epitope spreading and its regulation by co-stimulatory molecules, Immunol. Rev. 164 (1998) 63-72.

C. L. Vanderlugt, K. L. Neville, K. M. Nikcevich, T. N. Eagar, J. A. Bluestone, S. D. Miller, Pathologic role and temporal appearance of newly emerging autoepitopes in relapsing remitting experimental autoimmune encephalomyelitis, J. Immunol. 164 (2000) 670-678.

V. K. Tuohy, M. Yu, L. Yin, J. A. Kawczak, J. M. Johnson, P. M. Mathisen, B. Weinstock-Guttman, R. P. Kinkel, The epitope spreading cascade during progression of experimental autoimmune encephalomyelitis and multiple sclerosis, Immunol. Rev. 164 (1998) 93-100.

W. S. Begolka, C. L. Vanderlugt, S. M. Rahbe, S. D. Miller, Differential expression of inflammatory cytokines parallels progression of central nervous system pathology in two clinically distinct models of multiple sclerosis, J. Immunol. 161 (1998) 4437-4446.

T. M. Pribyl, C. W. Campagnoni, K. Kampf, T. Kashima, V. W. Handley, J. McMahon, A. T. Campagnoni, The human myelin basic protein gene is included within a 179-kilobase transcription unit: expression in the immune and central nervous systems, Proc. Natl. Acad. Sci. USA 90 (1993) 10695-10699.

T. M. Pribyl, C. Campagnoni, K. Kampf, V. W. Handley, A. T. Campagnoni, The major myelin protein genes are expressed in the human thymus, J. Neurosci. Res. 45 (1996) 812-819.

R. B. Fritz, I. Kalvakolanu, Thymic expression of the golli-myelin basic protein gene in the SJL/J mouse, J. Neuroimmunol. 57 (1995) 93-99.

N. Kawakami, S. Lassmann, Z. Li, F. Odoardi, T. Ritter, T. Ziemssen, W. E. Klinkert, J. W. Ellwart, M. Bradt, K. Krivacic, H. Lassmann, R. M. Ransohoff, H. D. Volk, H. Wekerle, C. Linington, A. Flügel, The activation status of neuroantigen-specific T cells in the target organ determines the clinical outcome of autoimmune encephalomyelitis, J. Exp. Med. 1999 (2004) 185-197.

A. L. Astier, G. Meiffren, S. Freeman, D. A. Hafler, Alterations in CD46-mediated Tr1 regulatory T cells in patients with multiple sclerosis, J. Clin. Invest. 116 (2006) 3252-3257.

A. L. Zozulya, H. Wiendl, The role of regulatory T cells in multiple sclerosis, Nat. Clin. Pract. Neurol. 4 (2008) 384-398.

A. Ma, Z. Xiong, Y. Hu, S. Qi, L. Song, H. Dun, L. Zhang, D. Lou, P. Yang, Z. Zhao, X. Wang, D. Zhang, P. Daloze, H. Chen, Dysfunction of IL-10—producing type 1 regulatory T cells and CD4(+)CD25(+) regulatory T cells in a mimic model of human multiple sclerosis in Cynomolgus monkey, Int. Immunopharmacol. 9 (2009) 599-608.

I. M. Stromnes, J. M. Goverman, Passive induction of experimental allergic encephalomyelitis, Nat. Prot. 1 (2006) 1952-1960.

G. Shi, C. A. Cox, B. P. Vistica, E. F. Wawrousek, I. Gery, Phenotype switching by inflammation-inducing polarized Th17 cells, but not by Th1 cells. J. Immunol. 181 (2008) 7205-7213.

E. A. Kabat, A. Wolf, A. E. Bezer, Experimental studies on acute disseminated encephalomyelitis in rhesus monkeys, Res. Publ. Assoc. Res. Ner. Ment. Dis. 28 (1950) 113-132.

J. Freund, M. M. Lipton, L. R. Morrison, Demyelination in the guinea pig in chronic allergic encephalomyelitis produced by injecting guinea pig brain in oil emulsion containing a variant of *Mycobacterium butyricum*, Arch. Pathol. (Chic.) 50 (1950) 108-121.

S. Levine, R. Sowinski, Experimental allergic encephalomyelitis in inbred and outbred mice, J. Immunol. 110 (1973) 139-143.

S. H. Appel, M. B. Bornstein, The application of tissue culture to the study of experimental allergic encephalomyelitis. II. Serum factors responsible for demyelination, J. Exp. Med. 119 (1964) 303-312.

D. O. Willenborg, Transfer of lesions of allergic encephalomyelitis in sheep with cell-free lymph from animals sensitized with homologous spinal cord plus adjuvant, Scand. J. Immunol. 16 (1982) 437-441.

C. B. Marta, A. R. Oliver, R. A. Sweet, S. E. Pfeiffer, N. H. Ruddle, Pathogenic myelin oligodendrocyte glycoprotein antibodies recognize glycosylated epitopes and perturb oligodendrocyte physiology, Proc. Natl. Acad. Sci. USA 102 (2005) 13992-13997.

J. A. Lyons, M. J. Ramsbottom, A. H. Cross, Critical role of antigen-specific antibody in experimental autoimmune encephalomyelitis induced by recombinant myelin oligodendrocyte glycoprotein, Eur. J. Immunol.32 (2002) 1905-1913.

C. Bourquin, A. Schubart, S. Tobollik, I. Mather, S. Ogg, R. Liblau, C. Linington, Selective unresponsiveness to conformational B cell epitopes of the myelin oligodendrocyte glycoprotein in H2-b mice, J. Immunol. 171 (2003) 455-461.

P. Dharmasaroja, Specificity of autoantibodies to epitopes of myelin proteins in multiple sclerosis, J. Neurol. Sci. 206 (2003) 7-16.

Y. Qin, P. Duquette, B-cell immunity in MS, Int. MS J. 10 (2003) 110-120.

T. Ziemssen, F. Ziemssen, The role of the humoral immune system in multiple sclerosis (MS) and its animal model experimental autoimmune encephalomyelitis, Autoimmun. Rev. 4 (2005) 460-467.

P. Martin Mdel, N. L. Monson, Potential role of humoral immunity in the pathogenesis of multiple sclerosis (MS) and experimental autoimmune encephalomyelitis (EAE), Front. Biosci. 12 (2007) 2735-2749.

K. A. McLaughlin, K. W. Wucherpfennig, B cells and autoantibodies in the pathogenesis of multiple sclerosis and related inflammatory demyelinating diseases, Adv. Immunol. 98 (2008) 121-149.

S. Kuerten, R. Pauly, S. Blaschke, A. Rottlaender, C. C. Kaiser, M. Schroeter, G. R. Fink, K. Addicks, The significance of a B cell-dependent immunopathology in multiple sclerosis, Fortschr. Neurol. Psychiatr. 79 (2011) 83-91.

S. Jarius, F. Paul, D. Franciotta, P. Waters, F. Zipp, R. Hohlfeld, A. Vincent, B. Wildemann, Mechanisms of disease: aquaporin-4 antibodies in neuromyelitis optica, Nat. Clin. Pract. Neurol.4 (2008) 202-214.

M. Morris-Downes, P. A. Smith, J. L. Rundle, S. J. Piddlesden, D. Baker, D. Pham-Dinh, N. Hejmans, S. Amor, Pathological and regulatory effects of anti-myelin antibodies in experimental allergic encephalomyelitis in mice, J. Neuroimmunol. 125 (2002) 114-124.

Z. Jingwu, A. A. Vandenbark, M. P. Jacobs, H. Offner, J. C. M. Raus, Murine monoclonal anti-myelin basic protein (MBP) antibodies inhibit proliferation and cytotoxicity of MBP-specific human T cell clones, J. Neuroimmunol. 24 (1989) 87-94.

V. K. Tuohy, Peptide determinants of myelin proteolipid protein (PLP) in autoimmune demyelinating disease: a review, Neurochem. Res. 19 (1993) 935-944.

E. A. Elliott, H. I. McFarland, S. H. Nye, R. Cofiell, T. M. Wilson, J. A. Wilkins, S. P. Squinto, L. A. Matis, J. P. Mueller, Treatment of experimental encephalomyelitis with a novel chimeric fusion protein of myelin basic protein and proteolipid protein, J. Clin. Invest. 98 (1996) 1602-1612.

S. Kuerten, F. S. Lichtenegger, S. Faas, D. N. Angelov, M. Tary-Lehmann, P. V. Lehmann, MBP-PLP fusion protein-induced EAE in C57BL/6 mice, J. Neuroimmunol. 177 (2006) 99-111.

C. C. Bernard, Experimental autoimmune encephalomyelitis in mice: genetic control of susceptibility, J. Immunogenet. 3 (1976) 263-274.

S. S. Zamvil, D. J. Mitchell, A. C. Moore, K. Kitamura, L. Steinman, J. B. Rothbard, T-cell epitope of the autoantigen myelin basic protein that induces encephalomyelitis, Nature 324 (1986) 258-260.

R. B. Fritz, M. L. Zhao, Active and passive experimental autoimmune encephalomyelitis in strain 129/J (H2b) mice, J. Neurosci. Res. 5 (1996) 471-474.

C. P. Genain, M. H. Nguyen, N. L. Letvin, R. Pearl, R. L. Davis, M. Adelman, M. B. Lees, C. Linington, S. L. Hauser, Antibody facilitation of multiple sclerosis-like lesions in a nonhuman primate. J. Clin. Invest. 96 (1995) 2966-2974.

K. G. Warren, I. Catz, Relative frequency of autoantibodies to myelin basic protein and proteolipid protein in optic neuritis and multiple sclerosis cerebrospinal fluid, J. Neurol. Sci. 121 (1994) 66-73.

M. K. Storch, S. Piddlesden, M. Haltia, M. Iivanainen, P. Morgan, H. Lassmann, Multiple sclerosis: in situ evidence for antibody- and complement-mediated demyelination, Ann. Neurol. 43 (1998) 465-471.

C. Lucchinetti, W. Bruck, J. Parisi, B. Scheithauer, M. Rodriguez, H. Lassmann, Heterogeneity of multiple sclerosis lesions: implications for the pathogenesis of demyelination, Ann. Neurol. 47 (2000) 707-717.

B. G. Weinshenker, P. C. O'Brien, T. M. Petterson, J. H. Noseworthy, C. F. Lucchinetti, D. W. Dodick, A. A. Pineda, L. N. Stevens, M. Rodriguez, A randomized trial of plasma exchange in acute central nervous system inflammatory demyelinating disease, Ann. Neurol. 46 (1999) 878-886.

M. Munemoto, Y. Otaki, S. Kasama, M. Nanami, M. Tokuyama, M. Yahiro, Y. Hasuike, T. Kuragano, H. Yoshikawa, H. Nonoguchi, T. Nakanishi, Therapeutic efficacy of double filtration plasmapheresis in patients with anti-aquaporin-4 antibody-positive multiple sclerosis. J. Clin. Neurosci. (2011), epub.

R. B. Fritz, C. H. Chou, D. E. McFarlin, Induction of experimental allergic encephalomyelitis in PL/J and (SJL/J x PL/J)F1 mice by myelin basic protein and its peptides: localization of a second encephalitogenic determinant, J. Immunol. 130 (1983) 191-194.

P. Whiting, R. Harbord, C. Main C, et al. Accuracy of MRI for the diagnosis of multiple sclerosis: systematic review. BMJ 2006; 15:875-884.

---

We claim:

1. A method for detecting an antibody directed against whole brain lysate antigens in a patient having relapsing remitting multiple sclerosis (RRMS) in clinical remission, or in a patient having clinically isolated syndrome (CIS), or in a patient suspected to have multiple sclerosis (MS), comprising:
   a) providing a sample of peripheral blood from said human being containing peripheral blood mononuclear cells (PBMCs);
      i) exposing said sample to a B-cell polyclonal activator in vitro to stimulate memory B cells in said PBMCs to become activated and start producing antibodies;
      ii) placing said sample in step i) onto a filter plate coated with whole brain lysate; and
   b) detecting the presence of a whole brain lysate specific antibody obtained in step a) bound to said whole brain lysate antigen.

2. The method of claim 1, where the time for polyclonal activation is from 3 to 8 days in vitro.

3. The method of claim 1, said step of detecting includes using a secondary antibody binding to said whole brain lysate antigen-specific antibody.

4. The method of claim 1, where said step of detecting being carried out using one or more of enzyme-linked immunosorbent assay (ELISA), fluorometric spot assay, enzyme-linked immune spot assay (ELISPOT), immunoblotting, radioimmunoassay, and immunoprecipitation assay.

5. The method of claim 1, said step of detection being carried out using a method selected from the group consisting of enzyme linked immune spot assay (ELISPOT), use of a bead array and/or use of a protein array.

6. The method of claim 1 said B cell polyclonal activator selected from the group consisting of IL-2, R848, and 2-mercaptoethanol.

\* \* \* \* \*

SEQUENCE LISTING

```
<160> NUMBER OF SEQ ID NOS: 7

<210> SEQ ID NO 1
<211> LENGTH: 247
<212> TYPE: PRT
<213> ORGANISM: Homo/sapiens
<220> FEATURE:
<221> NAME/KEY: CHAIN
<222> LOCATION:
<223> OTHER INFORMATION: Myelin Oligodendrocyte Glycoprotein (hMOG)

<400> SEQUENCE: 1

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Val Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
```

```
              195                 200                 205
Ile Thr Leu Phe Val Ile Val Pro Val Leu Gly Pro Leu Val Ala Leu
    210                 215                 220
Ile Ile Cys Tyr Asn Trp Leu His Arg Arg Leu Ala Gly Gln Phe Leu
225                 230                 235                 240
Glu Glu Leu Arg Asn Pro Phe
                245

<210> SEQ ID NO 2
<211> LENGTH: 20
<212> TYPE: PRT
<213> ORGANISM: Homo/sapiens
<220> FEATURE:
<221> NAME/KEY: PEPTIDE
<222> LOCATION:
<223> OTHER INFORMATION: Myelin Oligodendrocyte Glycoprotein residues 35
      through 55

<400> SEQUENCE: 2

Ser Ser Tyr Ala Gly Gln Phe Arg Val Ile Gly Pro Arg His Pro Ile
1               5                   10                  15
Arg Ala Leu Val
            20

<210> SEQ ID NO 3
<211> LENGTH: 197
<212> TYPE: PRT
<213> ORGANISM: Homo/sapiens
<220> FEATURE:
<221> NAME/KEY: CHAIN
<222> LOCATION:
<223> OTHER INFORMATION: Myelin Basic Protein, Isoform 3, 21.5 kDa

<400> SEQUENCE: 3

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Arg Gly Leu Ser Leu Ser Arg Phe Ser Trp Gly
    130                 135                 140
Ala Glu Gly Gln Arg Pro Gly Phe Gly Tyr Gly Gly Arg Ala Ser Asp
145                 150                 155                 160
Tyr Lys Ser Ala His Lys Gly Phe Lys Gly Val Asp Ala Gln Gly Thr
                165                 170                 175
Leu Ser Lys Ile Phe Lys Leu Gly Gly Arg Asp Ser Arg Ser Gly Ser
            180                 185                 190
Pro Met Ala Arg Arg
```

-continued

```
            195

<210> SEQ ID NO 4
<211> LENGTH: 247
<212> TYPE: PRT
<213> ORGANISM: Homo/sapiens
<220> FEATURE:
<221> NAME/KEY: CHAIN
<222> LOCATION:
<223> OTHER INFORMATION: Human Proteolipid Protein (MP4)

<400> SEQUENCE: 4

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
    50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Glu Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Thr Phe Asn Thr Pro Trp Asn Ala Phe Pro Gly Lys Val Cys Gly Ser
            180                 185                 190

Asn Leu Leu Ser Ile Cys Lys Thr Ala Glu Phe Gln Met Thr Phe His
        195                 200                 205

Leu Phe Ile Ala Ala Phe Val Gly Ala Ala Thr Leu Val Ser Leu
    210                 215                 220

Leu Thr Phe Met Ile Ala Ala Thr Tyr Asn Phe Ala Val Leu Lys Leu
225                 230                 235                 240

Met Gly Arg Gly Thr Lys Phe
                245

<210> SEQ ID NO 5
<211> LENGTH: 13
<212> TYPE: PRT
<213> ORGANISM: Homo/sapiens
<220> FEATURE:
<221> NAME/KEY: PEPTIDE
<222> LOCATION:
<223> OTHER INFORMATION: Proteolipid Protein Peptide, residues 139
      through 151

<400> SEQUENCE: 5

His Cys Leu Gly Lys Trp Leu Gly His Pro Asp Lys Phe
1               5                   10
```

-continued

```
<210> SEQ ID NO 6
<211> LENGTH: 8
<212> TYPE: PRT
<213> ORGANISM: Artificial Sequence
<220> FEATURE:
<221> NAME/KEY: PEPTIDE
<222> LOCATION:
<223> OTHER INFORMATION: Linker for Myelin Basic Protein and Proteolipid
      Protein (MP4); designed peptide based on size and polarity to act
      as a linker between human myelin basic protein and human
      proteolipiid protein

<400> SEQUENCE: 6

Leu Leu Gly Gly Leu Glu Asp Pro
1               5

<210> SEQ ID NO 7
<211> LENGTH: 452
<212> TYPE: PRT
<213> ORGANISM: Artificial Sequence
<220> FEATURE:
<221> NAME/KEY: CHAIN
<222> LOCATION:
<223> OTHER INFORMATION: Human Myelin Basic Protein Linked to Human
      Proteolipid Protein MP4 Using the Linker of Sequence ID. No. 6.

<400> SEQUENCE: 7

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
        50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg Leu Leu Gly Gly Leu Glu Asp Pro Met Gly Leu
        195                 200                 205

Leu Glu Cys Cys Ala Arg Cys Leu Val Gly Ala Pro Phe Ala Ser Leu
210                 215                 220

Val Ala Thr Gly Leu Cys Phe Phe Gly Val Ala Leu Phe Cys Gly Cys
225                 230                 235                 240

Gly His Glu Ala Leu Thr Gly Thr Glu Lys Leu Ile Glu Thr Tyr Phe
                245                 250                 255

Ser Lys Asn Tyr Gln Asp Tyr Glu Tyr Leu Ile Asn Val Ile His Ala
```

```
                    260                 265                 270
Phe Gln Tyr Val Ile Tyr Gly Thr Ala Ser Phe Phe Phe Leu Tyr Gly
        275                 280                 285

Ala Leu Leu Leu Ala Glu Gly Phe Tyr Thr Thr Gly Ala Val Glu Gln
        290                 295                 300

Ile Phe Gly Asp Tyr Lys Thr Thr Ile Cys Gly Lys Gly Leu Ser Ala
305                 310                 315                 320

Thr Val Thr Gly Gly Gln Lys Gly Arg Gly Ser Arg Gly Gln His Gln
                325                 330                 335

Ala His Ser Leu Glu Arg Val Cys His Cys Leu Gly Lys Trp Leu Gly
            340                 345                 350

His Pro Asp Lys Phe Val Gly Ile Thr Tyr Ala Leu Thr Val Val Trp
        355                 360                 365

Leu Leu Val Phe Ala Cys Ser Ala Val Pro Val Tyr Ile Thr Phe Asn
        370                 375                 380

Thr Pro Trp Asn Ala Phe Pro Gly Lys Val Cys Gly Ser Asn Leu Leu
385                 390                 395                 400

Ser Ile Cys Lys Thr Ala Glu Phe Gln Met Thr Phe His Leu Phe Ile
                405                 410                 415

Ala Ala Phe Val Gly Ala Ala Ala Thr Leu Val Ser Leu Leu Thr Phe
                420                 425                 430

Met Ile Ala Ala Thr Tyr Asn Phe Ala Val Leu Lys Leu Met Gly Arg
            435                 440                 445

Gly Thr Lys Phe
        450
```